(12) United States Patent
Goodman et al.

(10) Patent No.: US 8,562,986 B2
(45) Date of Patent: Oct. 22, 2013

(54) ENGINEERED ANTI-ALPHA V-INTEGRIN HYBRID ANTIBODIES

(75) Inventors: Simon Goodman, Griesheim (DE);
Diane Hahn, Seeheim-Jugenheim (DE);
Francesc Mitjans, Igualada (ES);
Jaume Adan, Mataro (ES); Kin-Ming Lo, Lexington, MA (US)

(73) Assignee: Merck Patent GmbH, Darmstadt (DE)

( * ) Notice: Subject to any disclaimer, the term of this patent is extended or adjusted under 35 U.S.C. 154(b) by 532 days.

(21) Appl. No.: 12/669,408

(22) PCT Filed: Jul. 17, 2008

(86) PCT No.: PCT/EP2008/005852
§ 371 (c)(1),
(2), (4) Date: Jun. 16, 2010

(87) PCT Pub. No.: WO2009/010290
PCT Pub. Date: Jan. 22, 2009

(65) Prior Publication Data
US 2010/0254977 A1 Oct. 7, 2010

(30) Foreign Application Priority Data
Jul. 17, 2007 (EP) .................................... 07013964

(51) Int. Cl.
*A61K 39/395* (2006.01)

(52) U.S. Cl.
USPC .................................... 424/133.1; 530/387.1

(58) Field of Classification Search
None
See application file for complete search history.

(56) References Cited

U.S. PATENT DOCUMENTS 5,985,278 A * 11/1999 Mitjans et al. ............. 424/143.1

FOREIGN PATENT DOCUMENTS

| EP | 0770622 B1 | 2/2000 |
|---|---|---|
| EP | 0719859 B1 | 7/2003 |
| EP | 1362868 A2 | 11/2003 |
| WO | WO-98/52976 A1 | 11/1998 |
| WO | WO-00/15244 A2 | 6/2000 |
| WO | WO-00/34317 A2 | 8/2000 |
| WO | WO-02/069232 A2 | 9/2002 |
| WO | WO-2004/056308 A2 | 7/2004 |
| WO | WO-2005/016969 A2 | 2/2005 |
| WO | WO-2007/076950 A1 | 7/2007 |
| WO | WO-2007/084620 A2 | 7/2007 |

OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Lacal et al. (2003) "Targeted Search for Anticancer Drugs—CNIO Cancer Conference," *IDrugs* 6(5):437-441.
Rader et al. (1998) "A phage display approach for rapid antibody humanization: Designed combinatorial V gene libraries," *Proc. Natl. Acad. Sci. USA* 95:8910-8915.
International Search Report for PCT/EP2008/005852, mailed on Feb. 9, 2009, 5 pages.
Boshart et al. (1985) "A Very Strong Enhancer is Located Upstream of an Immediate Early Gene of Human Cytomegalovirus," *Cell*, vol. 41, 521-530.
Eskens et al. (2003) "Phase I and pharmacokinetic study of continuous twice weekly intravenous administration of Cilengitide (EMD 121974), a novel inhibitor of the integrins $\alpha v\beta 3$ and $\alpha v\beta 5$ in patients with advanced solid tumours," *European Journal of Cancer* 39, 917-926.
Forsman et al. (2004) "Phylogenetic Analysis of Polyomavirus Simian Virus 40 from Monkeys and Humans Reveals Genetic Variation," *Journal of Virology*, 9306-9316.
Gillies et al. (1998) "Antibody-IL-12 Fusion Proteins are Effective in SCID Mouse Models of Prostate and Colon Carcinoma Metastases," *The Journal of Immunology*, 160: 6195-6203.
Ilyinskii et al. (1992) "Genetic Analysis of Simian Virus 40 from Brains and Kidneys of Macaque Monkeys," *Journal of Virology*, vol. 66, No. 11, 6353-6360.
Kawasaka et al. (2001) "Evolutionary dynamics of the human immunoglobulin κ locus and the germline repertoire of the Vκ genes," *Eur. J. Immunol.*, 31: 1017-1028.
Krawinkel et al. (1982) "Comparison of the hinge-coding segments in human immunoglobulin gamma heavy chain genes and the linkage of the gamma 2 and gamma 4 subclass genes," *The EMMBO Journal*, vol. 1, No. 4, 403-407.
Lo et al. (2005) "Engineering a pharmacologically superior form of leptin for the treatment of obesity," *Protein Engineering, Design & Selection*, vol. 18, No. 1, 1-10.
Lo et al. (1998) "High level expression and secretion of Fc-X fusion proteins in mammalian cells," *Protein Engineering*, vol. 11, No. 6, 495-500.
Mitjans et al. (1995) "An anti-αv-integrin antibody that blocks integrin function inhibits the development of a human melanoma in nude mice," *Journal of Cell Science* 108, 2825-2838.

(Continued)

*Primary Examiner* — Laura B Gooddard
*Assistant Examiner* — Meera Natarajan
(74) *Attorney, Agent, or Firm* — Goodwin Procter LLP

(57) ABSTRACT

The invention relates to engineered antibodies which specifically bind to integrin receptors, especially the alpha V integrin receptor subunit. The antibodies comprise the antigen binding sites (CDRs) of a known mouse anti-integrin antibody, as well as hybrid light chain variable sequences, mutated heavy chain variable sequences (Frs) and modified heavy chain constant sequences. The novel antibodies have improved immunogenic and expression properties and elicit excellent anti-angiogenic as well as anti-tumor activities in humans in monotherapy but also and above all in combination with other angiogenesis and tumor inhibiting agents.

36 Claims, 15 Drawing Sheets

(56) References Cited

OTHER PUBLICATIONS

Figure 2:
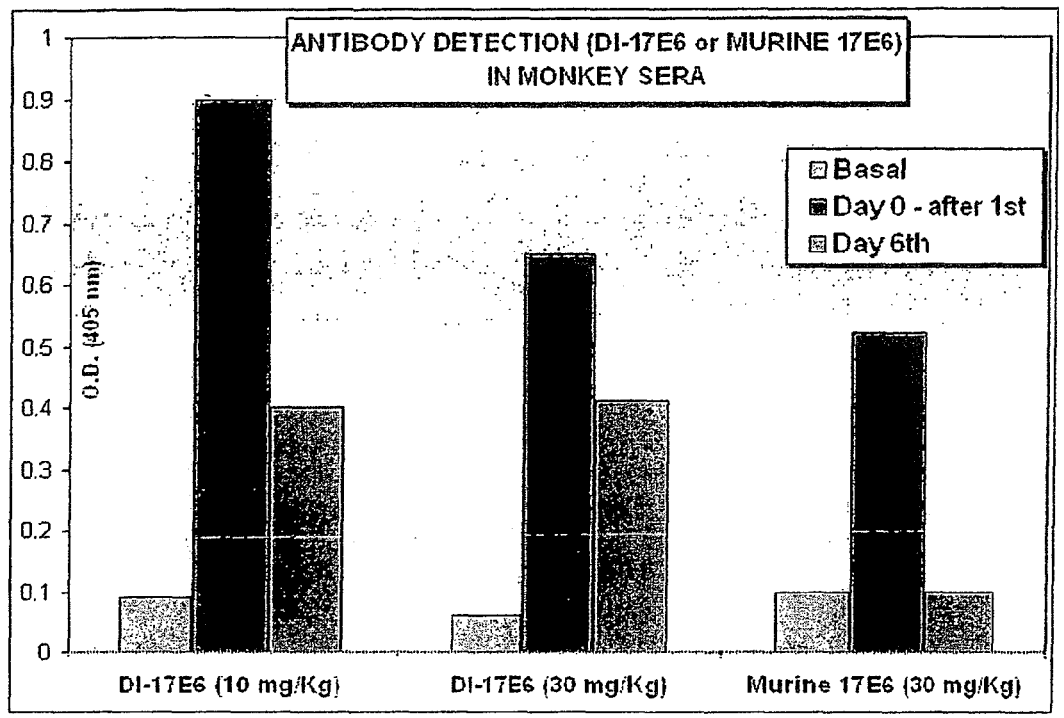

Schäble et al. (1999) "Characteristics of the immunoglobulin V∝ genes, pseudogenes, relics and orphons in the mouse genome," *Eur. J. Immunol.*, 29: 2082-2086.

Simonsen et al. (1983) "Isolation and expression of an altered mouse dihydrofolate reductase cDNA," *PNAS USA*, vol. 80, 2495-2499.

Strausberg et al. (2002) "Generation and initial analysis of more than 15,000 full-length human and mouse cDNA sequences," *PNAS*, vol. 99, No. 26, 16899-16903.

Sutcliffe (1978) "Nucleotide sequence of the ampicillin resistance gene of *Escherichia coli* plasmid pBR322," *PNAS USA*, vol. 75, No. 8, 3737-3741.

* cited by examiner

Figure 1A

```
D  I  Q  M  T  Q  S  P  S  S  L  S  A  S  V  G  D  R  V  T  I  T  C  R  A  S
GACATCCAGATGACCCAGAGCCCAAGCAGCCTGAGCCCCAGCGTGGGTGACAGAGTGACCATCACCTGTAGGGCAAGT

Q  D  I  S  N  Y  L  A  W  Y  Q  Q  K  P  G  K  A  P  K  L  L  I  Y  Y  T  S
CAGGACATTAGCAATTATTTAGCCTGGTACCAGCAGAAGCCAGGTAAGGCTCCAAAGCTGCTGATCTACTACACATCA

K  I  H  S  G  V  P  S  R  F  S  G  S  G  S  G  T  D  Y  T  F  T  I  S  S  L
AAAATCCACTCAGGTGTGCCAAGCAGATTCAGCGGTAGCGGTAGCGGTACCGACTACACCTTCACCATCAGCAGCCTC

Q  P  E  D  I  A  T  Y  Y  C  Q  Q  G  N  T  F  P  Y  T  F  G  Q  G  T  K  V
CAGCCAGAGGACATCGCCACCTACTACTGCCAACAGGGTAATACGTTTCCGTACACGTTCGGCCAAGGGACCAAGGTG

E  I  K                         (SEQ ID No. 1)
GAAATCAAA
```

Figure 1B

```
Q  V  Q  L  Q  Q  S  G  G  E  L  A  K  P  G  A  S  V  K  V  S  C  K  A  S  G
CAGGTCCAGCTTCAGCAGTCTGGGGGCGAACTGGCCAAGCCTGGGGCCTCAGTGAAGGTGTCCTGCAAGGCTTCTGGC

Y  T  F  S  S  F  W  M  H  W  V  R  Q  A  P  G  Q  G  L  E  W  I  G  Y  I  N
TACACCTTTAGTAGTTTCTGGATGCACTGGGTAAGACAGGCCCCTGGACAGGGTCTGGAATGGATTGGATACATTAAT

P  R  S  G  Y  T  E  Y  N  E  I  F  R  D  K  A  T  M  T  T  D  T  S  T  S  T
CCTAGATCTGGTTATACTGAGTaTAATGAGATATTCAGGGACAAGGCCACAATGACTACCGACACCTCCACCAGCACA

A  Y  M  E  L  S  S  L  R  S  E  D  T  A  V  Y  Y  C  A  S  F  L  G  R  G  A
GCCTACATGGAGCTGAGTAGCCTGAGATCTGAGGACACCGCAGTCTATTACTGTGCAAGTTTTCTGGGACGAGGGGCT

M  D  Y  W  G  Q  G  T  T  V  T  V  S  S        (SEQ ID No. 3)
ATGGACTACTGGGGTCAAGGAACCACCGTCACCGTCTCCTCA
```

Figure 1C

DIQMTQSPSSLSASVGDRVTITCRASQDISNYLAWYQQKPGKAPKLLIYYTSKIHSGVPS
RFSGSGSGTDYTFTISSLQPEDIATYYCQQGNTFPYTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC        (SEQ ID No. 5)

Figure 1D

QVQLQQSGGELAKPGASVKVSCKASGYTFSSFWMHWVRQAPGQGLEWIG**YINP
RSGYTEYNEIFRDKATMTTDTSTSTAYMELSSLRSEDTAVYYCASFLGRGAMDY
WGQGTTVTVSSASTKGPSVFPLAPCSRSTSESTAALGCLVKDYFPEPVTVSWNSG
ALTSGVHTFPAVLQSSGLYSLSSVVTVPSSNFGTQTYTCNVDHKPSNTKVDKTV
EPKSSDKTHTCPPCPAPPVAGPSVFLFPPKPKDTLMISRTPEVTCVVVDVSHEDPE
VQFNWYVDGVEVHNAKTKPREEQAQSTFRVVSVLTVVHQDWLNGKEYKCKVS
NKGLPAPIEKTISKTKGQPREPQVYTLPPSREEMTKNQVSLTCLVKGFYPSDIAVE
WESNGQPENNYKTTPPMLDSDGSFFLYSKLTVDKSRWQQGNVFSCSVMHEALH
NHYTQKSLSLSPGK              (SEQ ID No. 6)

M21 cells

CAKI-2 cells

Figure 17A

ATGGAGTTGCCTGTTAGGCTGTTGGTGCTGATGTTCTGGATTCCTGgtgaggagagagggaagtg
agggaggagaatggacagggagcaggagcactgaatcccattgctcattccatgtattctggcat
gggtgagaagatgggtcttatcctccagcatggggcctctggggtgaatacttgttagagggagg
ttccagatgggaacatgtgctataatgaagattatgaatggatgcctggatggtctaagtaat
gcctagaagtgactagacacttgcaattcactttttttggtaagaagagattttttaggctataaa
aaaatgttatgtaaaaataaacatcacagttgaaataaaaaaaaatataaggatgttcatgaatt
ttgtgtataactatgtatttctctctcattgtttcagCTTCCTTAAGCGACATCCAGATGACCCA
GAGCCCAAGCAGCCTGAGCGCCAGCGTGGGTGACAGAGTGACCATCACCTGTAGGGCAAGTCAGG
ACATTAGCAATTATTTAGCCTGGTACCAGCAGAAGCCAGGTAAGGCTCCAAAGCTGCTGATCTAC
TACACATCAAAAATCCACTCAGGTGTGCCAAGCAGATTCAGCGGTAGCGGTAGCGGTACCGACTA
CACCTTCACCATCAGCAGCCTCCAGCCAGAGGACATCGCCACCTACTACTGCCAACAGGGTAATA
CGTTTCCGTACACGTTCGGCCAAGGGACCAAGGTGGAAATCAAACgtaagtggatcccgcaattc
taaactctgaggggggtcggatgacgtggccattctttgcctaaagcattgagtttactgcaaggt
cagaaaagcatgcaaagccctcagaatggctgcaaagagctccaacaaaacaatttagaacttta
ttaaggaatagggggaagctaggaagaaactcaaaacatcaagatttttaaatacgcttcttggtc
tccttgctataattatctgggataagcatgctgtttctgtctgtccctaacatgcctgtgatt
atccgcaaacaacacacccaaggcagaactttgttacttaaacaccatcctgtttgcttctttc
ctcagGAACTGTGGCTGCACCATCTGTCTTCATCTTCCCGCCATCTGATGAGCAGTTGAAATCTG
GAACTGCCTCTGTTGTGTGCCTGCTGAATAACTTCTATCCCAGAGAGGCCAAAGTACAGTGCAAG
GTGGATAACGCCCTCCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAACACAAAGTCTACG
CCTGCGAAGTCACCCATCAGGGCCTGAGCTCGCCCGTCACAAAGAGCTTCAACAGGGGAGAGTGT
TAG        SEQ ID No. 29

Figure 17B

GACATCCAGATGACCCAGAGCCCAAGCAGCCTGAGCGCCAGCGTGGGTGACAGAGTGACCATCAC
CTGTAGGGCAAGTCAGGACATTAGCAATTATTTAGCCTGGTACCAGCAGAAGCCAGGTAAGGCTC
CAAAGCTGCTGATCTACTACACATCAAAAATCCACTCAGGTGTGCCAAGCAGATTCAGCGGTAGC
GGTAGCGGTACCGACTACACCTTCACCATCAGCAGCCTCCAGCCAGAGGACATCGCCACCTACTA
CTGCCAACAGGGTAATACGTTTCCGTACACGTTCGGCCAAGGGACCAAGGTGGAAATCAAA
SEQ ID No. 30

Figure 17C

CGAACTGTGGCTGCACCATCTGTCTTCATCTTCCCGCCATCTGATGAGCAGTTGAAATCTGGAAC
TGCCTCTGTTGTGTGCCTGCTGAATAACTTCTATCCCAGAGAGGCCAAAGTACAGTGGAAGGTGG
ATAACGCCCTCCAATCGGGTAACTCCCAGGAGAGTGTCACAGAGCAGGACAGCAAGGACAGCACC
TACAGCCTCAGCAGCACCCTGACGCTGAGCAAAGCAGACTACGAGAAACACAAAGTCTACGCCTG
CGAAGTCACCCATCAGGGCCTGAGCTCGCCCGTCACAAAGAGCTTCAACAGGGGAGAGTGT
SEQ ID No. 32

Figure 18A

ATGGAGTTGCCTGTTAGGCTGTTGGTGCTGATGTTCTGGATTCCTGgtgaggagagagggaagtg
agggaggagaatggacaggagcaggagcactgaatcccattgctcattccatgtattctggcat
gggtgagaagatgggtcttatcctccagcatggggcctctggggtgaatacttgttagagggagg
ttccagatgggaacatgtgctataatgaagattatgaaatggatgcctggatggtctaagtaat
gcctagaagtgactagacacttgcaattcactttttttggtaagaagagattttttaggctataaa
aaaatgttatgtaaaaataaacatcacagttgaaataaaaaaaatataaggatgttcatgaatt
ttgtgtataactatgtatttctctctcattgtttcagCTTCCTTAAGC<mark>AAGGTCCAGCTTCAGCA
GTCTGGGGCGAACTGGCCAAGCCTGGGGCCTCACTGAAGCTGTCCTGCAAGGCTTCTGGCTACA
CCTTTAGTAGTTTCTGGATGCACTGGGTAAGACAGGCCCCTGGACAGGGTCTGGAATGGATTGGA
TACATTAATCCTAGATCTGGTTATACTGAGTATAATGAGATATTCAGGCACAAGGCCACAATGAC
TACGGACACCTCCACCAGCACAGCCTACATGGAGCTGAGTAGCCTGAGATCTGAGGACACCGCAG
TCTATTACTGTGCAAGTTTTCTGGGACAGCGGCTATGGACTACTGGGGTCAAGGAACCACCGTC
ACCGTCTCCTCAG</mark>gtgagtaagctttctggggcgagccggcctgactttggctttgggcaggg
agtgggctaaggtgaggcaggtggcgccagccaggtgcacacccaatgcccgtgagcccagacac
tggaccctgctggaccctcgtggatagacaagaaccgaggggcctctgcgcctgggcccagctc
tgtcccacaccgcggtcacatggcaccacctctcttgcag<mark>CCTCCACCAAGGGCCCATCGGTCTT
CCCCCTGGCGCCCTGCTCCAGGAGCACCTCCGAGAGCACAGCGGCCCTGGGCTGCCTGGTCAAGG
ACTACTTCCCCGAACCGGTGACGGTGTCGTGGAACTCAGGCGCCCTGACCAGCGGCGTGCACACC
TTCCCAGCTGTCCTACAGTCCTCAGGACTCTACTCCCTCAGCAGCGTGGTGACCGTGCCCTCCAG
CAACTTCGGCACCCAGACCTACACCTGCAACGTAGATCACAAGCCCAGCAACACCAAGGTGGACA
AGACAGTTG</mark>gtgagaggccagctcagggagggagggtgtctgctggaagccaggctcagccctcc
tgcctggacgcaccccggctgtgcagccccagcccagggcagcaaggcaggccccatctgtctcc
tcacccggaggcctctgccccgccccactcatgctcagggagagggtcttctggcttttttccacca
ggctccaggcaggcacaggctgggtgcccctaccccaggcccttcacacacaggggcaggtgctt
ggctcagacctgccaaaagccatatccgggaggaccctgcccctgacctaagccgacccaaagg
ccaaactgtccactccctcagctcggacaccttctctcctcccagatccgagtaactcccaatct
tctctctgcag<mark>AGCCCAAATCTTCTGACAAAACTCACACATGCCCACCGTGCCCA</mark>gtaagccag
cccaggcctcgccctccagctcaaggcgggacaggtgccctagagtagcctgcatccagggacag
gccccagctgggtgctgacacgtccacctccatctcttcctcag<mark>CACCACCTCTGGCAGGACCCT
CAGTCTTCCTCTTCCCCCCAAAACCCAAGGACACCCTCATGATCTCCCGGACCCCTGAGGTCACC
TGCGTGGTGGTGGACGTGAGCCACGAAGACCCCGAGGTCCAGTTCAACTGGTACGTGGACGGCGT
GGAGGTGCATAATGCCAAGACAAAGCCACGGGAGGAGCAGGCCCAGAGCACGTTCCGTGTGGTCA
GCGTCCTCACCGTTGTCCACCAGGACTGGCTGAACGGCAAGGAGTACAAGTGCAAGGTCTCCAAC
AAAGGCCTCCCAGCCCCCATCGAGAAAACCATCTCCAAAACCAAA</mark>gtgggacccgcggggtatg
agggccacatggacagaggccggctcggcccacccctctgccctgagagtgaccgctgtaccaacc
tctgtccctacag<mark>GGCAGCCCCGAGAACCACAGGTGTACACCCTGCCCCCATCACGGGAGGAGAT
GACCAAGAACCAGGTCAGCCTGACCTGCCTGGTCAAAGGCTTCTACCCCAGCGACATCGCCGTGG
AGTGGGAGAGCAATGGGCAGCCGGAGAACAACTACAAGACCACACCTCCCATGCTGGACTCCGAC
GGCTCCTTCTTCCTCTACAGCAAGCTCACCGTGGACAAGAGCAGGTGGCAGCAGGGGAACGTCTT
CTCATGCTCCGTGATGCATGAGGCTCTGCACAACCACTACACACAGAAGAGCCTCTCCCTGTCCC
CGGGTAAA</mark>TGA
SEQ ID No. 34

Figure 18B

CAGGTCCAGCTTCAGCAGTCTGGGGGCGAACTGGCCAAGCCTGGGGCCTCAGTGAAGGTGTCCTG
CAAGGCTTCTGGCTACACCTTTAGTAGTTTCTGGATGCACTGGGTAAGACAGGCCCCTGGACAGG
GTCTGGAATGGATTGGATACATTAATCCTAGATCTGGTTATACTGAGTATAATGAGATATTCAGG
GACAAGGCCACAATGACTACCGACACCTCCACCAGCACAGCCTACATGGAGCTGAGTAGCCTGAG
ATCTGAGGACACCGCAGTCTATTACTGTGCAAGTTTTCTGGGACGAGGGGCTATGGACTACTGGG
GTCAAGGAACCACCGTCACCGTCTCCTCA    SEQ ID No. 35

Figure 18C

GCCTCCACCAAGGGCCCATCGGTCTTCCCCCTGGCGCCCTGCTCCAGGAGCACCTCCGAGAGCAC
AGCGGCCCTGGGCTGCCTGGTCAAGGACTACTTCCCCGAACCGGTGACGGTGTCGTGGAACTCAG
GCGCTCTGACCAGCGGCGTGCACACCTTCCCAGCTGTCCTACAGTCCTCAGGACTCTACTCCCTC
AGCAGCGTGGTGACCGTGCCCTCCAGCAACTTCGGCACCCAGACCTACACCTGCAACGTAGATCA
CAAGCCCAGCAACACCAAGGTGGACAAGACAGTT**GAGCCCAAATCTTCTGACAAAACTCACACAT
GCCCACCGTGCCCA**GCACCACCTGTGGCAGGACCGTCAGTCTTCCTCTTCCCCCCAAAACCCAAG
GACACCCTCATGATCTCCCGGACCCCTGAGGTCACGTGCGTGGTGGTGGACGTGAGCCACGAAGA
CCCCGAGGTCCAGTTCAACTGGTACGTGGACGGCGTGGAGGTGCATAATGCCAAGACAAAGCCAC
GGGAGGAGCAGGCCCAGAGCACGTTCCGTGTGGTCAGCGTCCTCACCGTTGTGCACCAGGACTGG
CTGAACGGCAAGGAGTACAAGTGCAAGGTCTCCAACAAAGGCCTCCCAGCCCCCATCGAGAAAAC
CATCTCCAAAACCAAAGGGCAGCCCCGAGAACCACAGGTGTACACCCTGCCCCCATCACGGGAGG
AGATGACCAAGAACCAGGTCAGCCTGACCTGCCTGGTCAAAGGCTTCTACCCCAGCGACATCGCC
GTGGAGTGGGAGAGCAATGGGCAGCCGGAGAACAACTACAAGACCACACCTCCCATGCTGGACTC
CGACGGCTCCTTCTTCCTCTACAGCAAGCTCACCGTGGACAAGAGCAGGTGGCAGCAGGGGAACG
TCTTCTCATGCTCCGTGATGCATGAGGCTCTGCACAACCACTACACACAGAAGAGCCTCTCCCTG
TCCCCGGGTAAA    SEQ ID No. 37

Figure 18D

GAGCCCAAATCTTCTGACAAAACTCACACATGCCCACCGTGCCCA    SEQ ID No. 39

Figure 19A

CAGGTCCAGCTTCAGCAGTCTGGGGGCGAACTGGCCAAGCCTGGGGCCTCAGTGAAGGTGTCCTG
CAAGGCTTCTGGCTACACCTTTAGTAGTTTCTGGATGCACTGGGTAAGACAGGCCCCTGGACAGG
GTCTGGAATGGATTGGATACATTAATCCTAGATCTGGTTATACTGAGTATAATGAGATATTCAGG
GACAAGGCCACAATGACTACCGACACCTCCACCAGCACAGCCTACATGGAGCTGAGTAGCCTGAG
ATCTGAGGACACCGCAGTCTATTACTGTGCAAGTTTTCTGGGACGAGGGGCTATGGACTACTGGG
GTCAAGGAACCACCGTCACCGTCTCCTCAGCCTCCACCAAGGGCCCATCGGTCTTCCCCCTGGCG
CCCTGCTCCAGGAGCACCTCCGAGAGCACAGCGGCCCTGGGCTGCCTGGTCAAGGACTACTTCCC
CGAACCGGTGACGGTGTCGTGGAACTCAGGCGCTCTGACCAGCGGCGTGCACACCTTCCCAGCTG
TCCTACAGTCCTCAGGACTCTACTCCCTCAGCAGCGTGGTGACCGTGCCCTCCAGCAACTTCGGC
ACCCAGACCTACACCTGCAACGTAGATCACAAGCCCAGCAACACCAAGGTGGACAAGACAGTT**GA
GCCCAAATCTTCTGACAAAACTCACACATGCCCACCGTGCCCA**GCACCACCTGTGGCAGGACCGT
CAGTCTTCCTCTTCCCCCCAAAACCCAAGGACACCCTCATGATCTCCCGGACCCCTGAGGTCACG
TGCGTGGTGGTGGACGTGAGCCACGAAGACCCCGAGGTCCAGTTCAACTGGTACGTGGACGGCGT
GGAGGTGCATAATGCCAAGACAAAGCCACGGGAGGAGCAGGCCCAGAGCACGTTCCGTGTGGTCA
GCGTCCTCACCGTTGTGCACCAGGACTGGCTGAACGGCAAGGAGTACAAGTGCAAGGTCTCCAAC
AAAGGCCTCCCAGCCCCCATCGAGAAAACCATCTCCAAAACCAAAGGGCAGCCCCGAGAACCACA
GGTGTACACCCTGCCCCCATCACGGGAGGAGATGACCAAGAACCAGGTCAGCCTGACCTGCCTGG
TCAAAGGCTTCTACCCCAGCGACATCGCCGTGGAGTGGGAGAGCAATGGGCAGCCGGAGAACAAC
TACAAGACCACACCTCCCATGCTGGACTCCGACGGCTCCTTCTTCCTCTACAGCAAGCTCACCGT
GGACAAGAGCAGGTGGCAGCAGGGGAACGTCTTCTCATGCTCCGTGATGCATGAGGCTCTGCACA
ACCACTACACACAGAAGAGCCTCTCCCTGTCCCCGGGTAAA    SEQ ID No. 42

Figure 19B

GACATCCAGATGACCCAGAGCCCAAGCAGCCTGAGCGCCAGCGTGGGTGACAGAGTGACCATCAC
CTGTAGGGCAAGTCAGGACATTAGCAATTATTTAGCCTGGTACCAGCAGAAGCCAGGTAAGGCTC
CAAAGCTGCTGATCTACTACACATCAAAAATCCACTCAGGTGTGCCAAGCAGATTCAGCGGTAGC
GGTAGCGGTACCGACTACACCTTCACCATCAGCAGCCTCCAGCCAGAGGACATCGCCACCTACTA
CTGCCAACAGGGTAATACGTTTCCGTACACGTTCGGCCAAGGGACCAAGGTGGAAATCAAACGAA
CTGTGGCTGCACCATCTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACAGTGGAAGGTGGATAA
CGCCCTCCAATCGGGTAACTCCCAGGAGAGTGTCACAGAGCAGGACAGCAAGGACAGCACCTACA
GCCTCAGCAGCACCCTGACGCTGAGCAAAGCAGACTACGAGAAACACAAAGTCTACGCCTGCGAA
GTCACCCATCAGGGCCTGAGCTCGCCCGTCACAAAGAGCTTCAACAGGGGAGAGTGT
SEQ ID No. 44

Figure 20A

DIQMTQTTSSLSASLGDRVIISCRASQDISNYLSWYQQKPDGTVKLLIF**YTSKLH
SGVPSRFSGSGSGTDYSLTISNLDQEDIATYFCQQGNTFPYT**FGGGTKVEMR
(SEQ ID No. 27)

Figure 20B

QVQLQQSGAELAEPGASVKMSCKASGYTFSSFWMHWVKQRPGQGLEWIG**YINPRS
GYTECNEIFRDKATMTADTSSSTAYMQLSGLTSEDSAVYYCASFLGRGAMD**YWGQ
GTSVTVSS    (SEQ ID No. 28)

SEQUENCE LISTING

```
<160> NUMBER OF SEQ ID NOS: 120

<210> SEQ ID NO 1
<211> LENGTH: 321
<212> TYPE: DNA
<213> ORGANISM: Artificial
<220> FEATURE:
<223> OTHER INFORMATION: mutated murine immunoglobulin chain
<220> FEATURE:
<221> NAME/KEY: CDS
<222> LOCATION: (1)..(321)
<223> OTHER INFORMATION: "SEQ.ID.No.1".  DI17E6 variable light chain
      (Fig. 1A)

<400> SEQUENCE: 1 gac atc cag atg acc cag agc cca agc agc ctg agc gcc agc gtg ggt        48
Asp Ile Gln Met Thr Gln Ser Pro Ser Ser Leu Ser Ala Ser Val Gly
1               5                   10                  15 gac aga gtg acc atc acc tgt agg gca agt cag gac att agc aat tat        96
Asp Arg Val Thr Ile Thr Cys Arg Ala Ser Gln Asp Ile Ser Asn Tyr
                20                  25                  30 tta gcc tgg tac cag cag aag cca ggt aag gct cca aag ctg ctg atc       144
Leu Ala Trp Tyr Gln Gln Lys Pro Gly Lys Ala Pro Lys Leu Leu Ile
            35                  40                  45 tac tac aca tca aaa atc cac tca ggt gtg cca agc aga ttc agc ggt       192
Tyr Tyr Thr Ser Lys Ile His Ser Gly Val Pro Ser Arg Phe Ser Gly
        50                  55                  60 agc ggt agc ggt acc gac tac acc ttc acc atc agc agc ctc cag cca       240
Ser Gly Ser Gly Thr Asp Tyr Thr Phe Thr Ile Ser Ser Leu Gln Pro
65                  70                  75                  80 gag gac atc gcc acc tac tac tgc caa cag ggt aat acg ttt ccg tac       288
Glu Asp Ile Ala Thr Tyr Tyr Cys Gln Gln Gly Asn Thr Phe Pro Tyr
                85                  90                  95 acg ttc ggc caa ggg acc aag gtg gaa atc aaa                           321
Thr Phe Gly Gln Gly Thr Lys Val Glu Ile Lys
                100                 105

<210> SEQ ID NO 2
<211> LENGTH: 107
<212> TYPE: PRT
<213> ORGANISM: Artificial
```

```
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Thr Ser Lys Ile His Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Phe Pro Tyr
                85                  90                  95

Thr Phe Gly Gln Gly Thr Lys Val Glu Ile Lys
            100                 105

<210> SEQ ID NO 3
<211> LENGTH: 354
<212> TYPE: DNA
<213> ORGANISM: Artificial
<220> FEATURE:
<223> OTHER INFORMATION: mutated murine immunoglobulin chain
<220> FEATURE:
<221> NAME/KEY: CDS
<222> LOCATION: (1)..(354)
<223> OTHER INFORMATION: "SEQ.ID.No.2".   DI17E6 variable heavy chain
      (Fig 1B)

<400> SEQUENCE: 3 cag gtc cag ctt cag cag tct ggg ggc gaa ctg gcc aag cct ggg gcc      48
Gln Val Gln Leu Gln Gln Ser Gly Gly Glu Leu Ala Lys Pro Gly Ala
1               5                   10                  15 tca gtg aag gtg tcc tgc aag gct tct ggc tac acc ttt agt agt ttc      96
Ser Val Lys Val Ser Cys Lys Ala Ser Gly Tyr Thr Phe Ser Ser Phe
            20                  25                  30 tgg atg cac tgg gta aga cag gcc cct gga cag ggt ctg gaa tgg att     144
Trp Met His Trp Val Arg Gln Ala Pro Gly Gln Gly Leu Glu Trp Ile
        35                  40                  45 gga tac att aat cct aga tct ggt tat act gag tat aat gag ata ttc     192
Gly Tyr Ile Asn Pro Arg Ser Gly Tyr Thr Glu Tyr Asn Glu Ile Phe
50                  55                  60 agg gac aag gcc aca atg act acc gac acc tcc acc agc aca gcc tac     240
Arg Asp Lys Ala Thr Met Thr Thr Asp Thr Ser Thr Ser Thr Ala Tyr
65                  70                  75                  80 atg gag ctg agt agc ctg aga tct gag gac acc gca gtc tat tac tgt     288
Met Glu Leu Ser Ser Leu Arg Ser Glu Asp Thr Ala Val Tyr Tyr Cys
                85                  90                  95 gca agt ttt ctg gga cga ggg gct atg gac tac tgg ggt caa gga acc     336
Ala Ser Phe Leu Gly Arg Gly Ala Met Asp Tyr Trp Gly Gln Gly Thr
            100                 105                 110 acc gtc acc gtc tcc tca                                              354
Thr Val Thr Val Ser Ser
        115

<210> SEQ ID NO 4
<211> LENGTH: 118
<212> TYPE: PRT
<213> ORGANISM: Artificial
<220> FEATURE:
<223> OTHER INFORMATION: Synthetic Construct
```

<400> SEQUENCE: 4

```
Gln Val Gln Leu Gln Gln Ser Gly Gly Glu Leu Ala Lys Pro Gly Ala
1               5                   10                  15
Ser Val Lys Val Ser Cys Lys Ala Ser Gly Tyr Thr Phe Ser Ser Phe
            20                  25                  30
Trp Met His Trp Val Arg Gln Ala Pro Gly Gln Gly Leu Glu Trp Ile
        35                  40                  45
Gly Tyr Ile Asn Pro Arg Ser Gly Tyr Thr Glu Tyr Asn Glu Ile Phe
    50                  55                  60
Arg Asp Lys Ala Thr Met Thr Thr Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ser Phe Leu Gly Arg Gly Ala Met Asp Tyr Trp Gly Gln Gly Thr
            100                 105                 110
Thr Val Thr Val Ser Ser
            115
```

<210> SEQ ID NO 5
<211> LENGTH: 214
<212> TYPE: PRT
<213> ORGANISM: Artificial
<220> FEATURE:
<223> OTHER INFORMATION: mutated murine immunoglobulin chain
<220> FEATURE:
<221> NAME/KEY: CHAIN
<222> LOCATION: (1)..(214)
<223> OTHER INFORMATION: SEQ.ID.No.3. DI17E6 variable and constant
      light chain. (Fig. 1C)
<220> FEATURE:
<221> NAME/KEY: CHAIN
<222> LOCATION: (1)..(107)
<223> OTHER INFORMATION: variable light chain
<220> FEATURE:
<221> NAME/KEY: BINDING
<222> LOCATION: (24)..(34)
<223> OTHER INFORMATION: CDR1=Seq.ID.No.5
<220> FEATURE:
<221> NAME/KEY: BINDING
<222> LOCATION: (50)..(56)
<223> OTHER INFORMATION: CDR2=Seq.ID.No.6
<220> FEATURE:
<221> NAME/KEY: BINDING
<222> LOCATION: (89)..(97)
<223> OTHER INFORMATION: CDR3=Seq.ID.No.7
<220> FEATURE:
<221> NAME/KEY: CHAIN
<222> LOCATION: (108)..(214)
<223> OTHER INFORMATION: constant light chain

<400> SEQUENCE: 5

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Asn Tyr
            20                  25                  30
Leu Ala Trp Tyr Gln Gln Lys Pro Gly Lys Ala Pro Lys Leu Leu Ile
        35                  40                  45
Tyr Tyr Thr Ser Lys Ile His Ser Gly Val Pro Ser Arg Phe Ser Gly
    50                  55                  60
Ser Gly Ser Gly Thr Asp Tyr Thr Phe Thr Ile Ser Ser Leu Gln Pro
65                  70                  75                  80
Glu Asp Ile Ala Thr Tyr Tyr Cys Gln Gln Gly Asn Thr Phe Pro Tyr
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 447
<212> TYPE: PRT
<213> ORGANISM: Artificial
<220> FEATURE:
<223> OTHER INFORMATION: mutated murine immunoglobulin chain
<220> FEATURE:
<221> NAME/KEY: CHAIN
<222> LOCATION: (1)..(447)
<223> OTHER INFORMATION: "SEQ.ID.No.4".  DI17E6 variable and constant
      light chain (Fig. 1D)
<220> FEATURE:
<221> NAME/KEY: CHAIN
<222> LOCATION: (1)..(118)
<223> OTHER INFORMATION: variable heavy chain
<220> FEATURE:
<221> NAME/KEY: BINDING
<222> LOCATION: (30)..(35)
<223> OTHER INFORMATION: CDR1=Seq.ID.No.8
<220> FEATURE:
<221> NAME/KEY: BINDING
<222> LOCATION: (50)..(66)
<223> OTHER INFORMATION: CDR2=Seq.ID.No.9
<220> FEATURE:
<221> NAME/KEY: BINDING
<222> LOCATION: (99)..(107)
<223> OTHER INFORMATION: CDR3=Seq.ID.No.10
<220> FEATURE:
<221> NAME/KEY: CHAIN
<222> LOCATION: (119)..(447)
<223> OTHER INFORMATION: constant heavy chain

<400> SEQUENCE: 6

Gln Val Gln Leu Gln Gln Ser Gly Gly Glu Leu Ala Lys Pro Gly Ala
1               5                   10                  15

Ser Val Lys Val Ser Cys Lys Ala Ser Gly Tyr Thr Phe Ser Ser Phe
            20                  25                  30

Trp Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Glu Ile Phe
    50                  55                  60

Arg Asp Lys Ala Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Phe Leu Gly Arg Gly Ala Met Asp Tyr Trp Gly Gln Gly Thr
            100                 105                 110
```

```
Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Asn Phe Gly Thr Gln Thr Tyr Thr Cys Asn Val Asp His Lys Pro Ser
            195                 200                 205

Asn Thr Lys Val Asp Lys Thr Val Glu Pro Lys Ser Ser Asp Lys Thr
        210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Ala Gln Ser Thr Phe Arg Val Val Ser
        290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 7
<211> LENGTH: 11
<212> TYPE: PRT
<213> ORGANISM: Murine
<220> FEATURE:
<221> NAME/KEY: BINDING
<222> LOCATION: (1)..(11)
<223> OTHER INFORMATION: "SEQ.ID.No.5".  CDR1 light chain DI17E6

<400> SEQUENCE: 7

Arg Ala Ser Gln Asp Ile Ser Asn Tyr Leu Ala
1               5                   10

<210> SEQ ID NO 8
```

```
<211> LENGTH: 7
<212> TYPE: PRT
<213> ORGANISM: Murine
<220> FEATURE:
<221> NAME/KEY: BINDING
<222> LOCATION: (1)..(7)
<223> OTHER INFORMATION: "SEQ.ID.No.6".   CDR2 light chain DI17E6

<400> SEQUENCE: 8

Tyr Thr Ser Lys Ile His Ser
1               5

<210> SEQ ID NO 9
<211> LENGTH: 9
<212> TYPE: PRT
<213> ORGANISM: Murine
<220> FEATURE:
<221> NAME/KEY: BINDING
<222> LOCATION: (1)..(9)
<223> OTHER INFORMATION: "SEQ.ID.No.7."   CDR3 light chain DI17E6

<400> SEQUENCE: 9

Gln Gln Gly Asn Thr Phe Pro Tyr Thr
1               5

<210> SEQ ID NO 10
<211> LENGTH: 5
<212> TYPE: PRT
<213> ORGANISM: Murine
<220> FEATURE:
<221> NAME/KEY: BINDING
<222> LOCATION: (1)..(5)
<223> OTHER INFORMATION: "SEQ.ID.No.8."   CDR1 heavy chain DI17E6

<400> SEQUENCE: 10

Ser Phe Trp Met His
1               5

<210> SEQ ID NO 11
<211> LENGTH: 17
<212> TYPE: PRT
<213> ORGANISM: Murine
<220> FEATURE:
<221> NAME/KEY: BINDING
<222> LOCATION: (1)..(17)
<223> OTHER INFORMATION: "SEQ.ID.No.10". CDR2 heavy chain DI17E6

<400> SEQUENCE: 11

Tyr Ile Asn Pro Arg Ser Gly Tyr Thr Glu Tyr Asn Glu Ile Phe Arg
1               5                   10                  15

Asp

<210> SEQ ID NO 12
<211> LENGTH: 9
<212> TYPE: PRT
<213> ORGANISM: Murine
<220> FEATURE:
<221> NAME/KEY: BINDING
<222> LOCATION: (1)..(9)
<223> OTHER INFORMATION: "SEQ.ID.No.10".   CDR3 heavy chain DI17E6

<400> SEQUENCE: 12

Phe Leu Gly Arg Gly Ala Met Asp Tyr
1               5

<210> SEQ ID NO 13
<211> LENGTH: 17
<212> TYPE: PRT
<213> ORGANISM: Artificial
```

-continued

```
<220> FEATURE:
<223> OTHER INFORMATION: mutated CDR region of murine Mab
<220> FEATURE:
<221> NAME/KEY: BINDING
<222> LOCATION: (1)..(17)
<223> OTHER INFORMATION: "SEQ ID No. 11":  CDR2 heavy chain mutated of
      DI17E6
<220> FEATURE:
<221> NAME/KEY: BINDING
<222> LOCATION: (1)..(17)
<223> OTHER INFORMATION: "SEQ ID No. 11":  mutated CDR2 heavy chain of
      DI17E6
<220> FEATURE:
<221> NAME/KEY: BINDING
<222> LOCATION: (1)..(17)
<223> OTHER INFORMATION: "SEQ ID No. 11":  CDR2 heavy chain of DI17E6
<220> FEATURE:
<221> NAME/KEY: MISC_FEATURE
<222> LOCATION: (11)..(11)
<223> OTHER INFORMATION: Xaa =C or  Y

<400> SEQUENCE: 13

Tyr Ile Asn Pro Arg Ser Gly Tyr Thr Glu Xaa Asn Glu Ile Phe Arg
1               5                   10                  15

Asp

<210> SEQ ID NO 14
<211> LENGTH: 23
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(23)
<223> OTHER INFORMATION: "SEQ.ID.No.12"  FR-1 light chain DI17E6

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 15
<211> LENGTH: 15
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(15)
<223> OTHER INFORMATION: "SEQ.ID.No.13"  FR-2 light chain DI17E6

<400> SEQUENCE: 15

Trp Tyr Gln Gln Lys Pro Gly Lys Ala Pro Lys Leu Leu Ile Tyr
1               5                   10                  15

<210> SEQ ID NO 16
<211> LENGTH: 32
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(32)
<223> OTHER INFORMATION: "SEQ.ID.No.14".  FR-3 light chain DI17E6

<400> SEQUENCE: 16

Gly Val Pro Ser Arg Phe Ser Gly Ser Gly Ser Gly Thr Asp Tyr Thr
```

```
                1               5                   10                  15
Phe Thr Ile Ser Ser Leu Gln Pro Glu Asp Ile Ala Thr Tyr Tyr Cys
                20                  25                  30

<210> SEQ ID NO 17
<211> LENGTH: 10
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(10)
<223> OTHER INFORMATION: "SEQ.ID.No.15"   FR-4 light chain DI17E6

<400> SEQUENCE: 17

Phe Gly Gln Gly Thr Lys Val Glu Ile Lys
1               5                   10

<210> SEQ ID NO 18
<211> LENGTH: 30
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(30)
<223> OTHER INFORMATION: "SEQ.ID.No.16".   mutated FR-1 heavy chain
      DI17E6
<220> FEATURE:
<221> NAME/KEY: MISC_FEATURE
<222> LOCATION: (9)..(9)
<223> OTHER INFORMATION: Xaa = A or any other amino acid which causes
      reduction of T-cell epitopes
<220> FEATURE:
<221> NAME/KEY: MISC_FEATURE
<222> LOCATION: (13)..(13)
<223> OTHER INFORMATION: Xaa = E or any other amino acid which causes
      reduction of T-cell epitopes
<220> FEATURE:
<221> NAME/KEY: MISC_FEATURE
<222> LOCATION: (20)..(20)
<223> OTHER INFORMATION: Xaa = M or any other amino acid which causes
      reduction of T-cell epitopes

<400> SEQUENCE: 18

Gln Val Gln Leu Gln Gln Ser Gly Xaa Glu Leu Ala Xaa Pro Gly Ala
1               5                   10                  15

Ser Val Lys Xaa Ser Cys Lys Ala Ser Gly Tyr Thr Phe Ser
                20                  25                  30

<210> SEQ ID NO 19
<211> LENGTH: 14
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(14)
<223> OTHER INFORMATION: "SEQ.ID.No.17"   mutated FR-2 heavy chain
      DI17E6
<220> FEATURE:
<221> NAME/KEY: MISC_FEATURE
<222> LOCATION: (3)..(3)
<223> OTHER INFORMATION: Xaa = K or any other amino acid that reduces
      number of T-cell epitopes
<220> FEATURE:
<221> NAME/KEY: MISC_FEATURE
<222> LOCATION: (5)..(5)
<223> OTHER INFORMATION: Xaa = R or any other amino acid that reduces
      number of T-cell epitopes
```

```
<400> SEQUENCE: 19

Trp Val Xaa Gln Xaa Pro Gly Gln Gly Leu Glu Trp Ile Gly
1               5                   10

<210> SEQ ID NO 20
<211> LENGTH: 32
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(32)
<223> OTHER INFORMATION: "SEQ.ID.No.18". mutated FR-3 heavy chain
      DI17E6
<220> FEATURE:
<221> NAME/KEY: MISC_FEATURE
<222> LOCATION: (6)..(6)
<223> OTHER INFORMATION: Xaa = A or any other amino acid that reduces
      number of T-cell epitopes
<220> FEATURE:
<221> NAME/KEY: MISC_FEATURE
<222> LOCATION: (10)..(10)
<223> OTHER INFORMATION: Xaa = S or any other amino acid that reduces
      number of T-cell epitopes
<220> FEATURE:
<221> NAME/KEY: MISC_FEATURE
<222> LOCATION: (16)..(16)
<223> OTHER INFORMATION: Xaa = Q or any other amino acid that reduces
      number of T-cell epitopes
<220> FEATURE:
<221> NAME/KEY: MISC_FEATURE
<222> LOCATION: (19)..(19)
<223> OTHER INFORMATION: Xaa = G or any other amino acid that reduces
      number of T-cell epitopes
<220> FEATURE:
<221> NAME/KEY: MISC_FEATURE
<222> LOCATION: (21)..(21)
<223> OTHER INFORMATION: Xaa = T or any other amino acid that reduces
      number of T-cell epitopes
<220> FEATURE:
<221> NAME/KEY: MISC_FEATURE
<222> LOCATION: (25)..(25)
<223> OTHER INFORMATION: Xaa = S or any other amino acid that reduces
      number of T-cell epitopes

<400> SEQUENCE: 20

Lys Ala Thr Met Thr Xaa Asp Thr Ser Xaa Ser Thr Ala Tyr Met Xaa
1               5                   10                  15

Leu Ser Xaa Leu Xaa Ser Glu Asp Xaa Ala Val Tyr Tyr Cys Ala Ser
            20                  25                  30

<210> SEQ ID NO 21
<211> LENGTH: 11
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(11)
<223> OTHER INFORMATION: "SEQ.ID.No.19". mutated FR-4 heavy chain
      DI17E6
<220> FEATURE:
<221> NAME/KEY: MISC_FEATURE
<222> LOCATION: (6)..(6)
<223> OTHER INFORMATION: Xaa = S or any other amino acid that reduces
      number of T-cell epitopes

<400> SEQUENCE: 21

Trp Gly Gln Gly Thr Xaa Val Thr Val Ser Ser
1               5                   10
```

```
<210> SEQ ID NO 22
<211> LENGTH: 30
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(30)
<223> OTHER INFORMATION: "SEQ.ID.No.20".   FR-1 heavy chain DI17E6

<400> SEQUENCE: 22

Gln Val Gln Leu Gln Gln Ser Gly Gly Glu Leu Ala Lys Pro Gly Ala
1               5                   10                  15

Ser Val Lys Val Ser Cys Lys Ala Ser Gly Tyr Thr Phe Ser
            20                  25                  30

<210> SEQ ID NO 23
<211> LENGTH: 14
<212> TYPE: PRT
<213> ORGANISM: Artificial
<220> FEATURE:
<223> OTHER INFORMATION: Artificial Sequence
<220> FEATURE:
<221> NAME/KEY: BINDING
<222> LOCATION: (1)..(14)
<223> OTHER INFORMATION: "SEQ.ID.No.21".   FR-2 heavy chain DI17E6

<400> SEQUENCE: 23

Trp Val Arg Gln Ala Pro Gly Gln Gly Leu Glu Trp Ile Gly
1               5                   10

<210> SEQ ID NO 24
<211> LENGTH: 32
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(32)
<223> OTHER INFORMATION: "SEQ.ID.No.22."   FR-3 heavy chain DI17E6

<400> SEQUENCE: 24

Lys Ala Thr Met Thr Thr Asp Thr Ser Thr Ser Thr Ala Tyr Met Glu
1               5                   10                  15

Leu Ser Ser Leu Arg Ser Glu Asp Thr Ala Val Tyr Tyr Cys Ala Ser
            20                  25                  30

<210> SEQ ID NO 25
<211> LENGTH: 11
<212> TYPE: PRT
<213> ORGANISM: Artificial
<220> FEATURE:
<223> OTHER INFORMATION: mutated murine immunoglobulin chain
<220> FEATURE:
<221> NAME/KEY: BINDING
<222> LOCATION: (1)..(11)
<223> OTHER INFORMATION: "SEQ.ID.No.23".   FR-4 heavy chain DI17E6

<400> SEQUENCE: 25

Trp Gly Gln Gly Thr Thr Val Thr Val Ser Ser
1               5                   10

<210> SEQ ID NO 26
<211> LENGTH: 15
<212> TYPE: PRT
<213> ORGANISM: Artificial
<220> FEATURE:
```

```
<223> OTHER INFORMATION: mutated murine immunoglobulin chain (portion)
<220> FEATURE:
<221> NAME/KEY: CHAIN
<222> LOCATION: (1)..(15)
<223> OTHER INFORMATION: "SEQ.ID.No.24".   modified IgG1 hinge region
      DI17E6

<400> SEQUENCE: 26

Glu Pro Lys Ser Ser Asp Lys Thr His Thr Cys Pro Pro Cys Pro
1               5                   10                  15

<210> SEQ ID NO 27
<211> LENGTH: 107
<212> TYPE: PRT
<213> ORGANISM: Murine
<220> FEATURE:
<221> NAME/KEY: CHAIN
<222> LOCATION: (1)..(107)
<223> OTHER INFORMATION: "SEQ.ID.No.25".   variable light chain 17E6
      (mouse)
<220> FEATURE:
<221> NAME/KEY: MISC_FEATURE
<222> LOCATION: (24)..(34)
<223> OTHER INFORMATION: "SEQ ID No. 25": CDR1 of light chain of mAb
      17E6 (mouse)
<220> FEATURE:
<221> NAME/KEY: MISC_FEATURE
<222> LOCATION: (50)..(56)
<223> OTHER INFORMATION: "SEQ ID No. 25": CDR2 of light chain of mAb
      17E6 (mouse)
<220> FEATURE:
<221> NAME/KEY: MISC_FEATURE
<222> LOCATION: (89)..(97)
<223> OTHER INFORMATION: "SEQ ID No. 25": CDR3 of light chain of mAb
      17E6 (mouse)

<400> SEQUENCE: 27

Asp Ile Gln Met Thr Gln Thr Thr Ser Ser Leu Ser Ala Ser Leu Gly
1               5                   10                  15

Asp Arg Val Ile Ile Ser Cys Arg Ala Ser Gln Asp Ile Ser Asn Tyr
                20                  25                  30

Leu Ser Trp Tyr Gln Gln Lys Pro Asp Gly Thr Val Lys Leu Leu Ile
            35                  40                  45

Phe Tyr Thr Ser Lys Leu His Ser Gly Val Pro Ser Arg Phe Ser Gly
50                  55                  60

Ser Gly Ser Gly Thr Asp Tyr Ser Leu Thr Ile Ser Asn Leu Asp Gln
65                  70                  75                  80

Glu Asp Ile Ala Thr Tyr Phe Cys Gln Gln Gly Asn Thr Phe Pro Tyr
                85                  90                  95

Thr Phe Gly Gly Gly Thr Lys Val Glu Met Arg
                100                 105

<210> SEQ ID NO 28
<211> LENGTH: 118
<212> TYPE: PRT
<213> ORGANISM: Mus musculus
<220> FEATURE:
<221> NAME/KEY: CHAIN
<222> LOCATION: (1)..(118)
<223> OTHER INFORMATION: "SEQ.ID.No.26".   variable heavy chain 17E6
<220> FEATURE:
<221> NAME/KEY: MISC_FEATURE
<222> LOCATION: (31)..(35)
<223> OTHER INFORMATION: "SEQ ID No. 26": CDR1 of heavy chain of mAb
      17E6 (mouse)
<220> FEATURE:
<221> NAME/KEY: MISC_FEATURE
<222> LOCATION: (50)..(66)
<223> OTHER INFORMATION: "SEQ ID No. 26": CDR2 of heavy chain of mAb
      17E6 (mouse)
```

```
<220> FEATURE:
<221> NAME/KEY: MISC_FEATURE
<222> LOCATION: (99)..(107)
<223> OTHER INFORMATION: "SEQ ID No. 26": CDR3 of heavy chain of mAb
      17E6 (mouse)

<400> SEQUENCE: 28

Gln Val Gln Leu Gln Gln Ser Gly Ala Glu Leu Ala Glu Pro Gly Ala
1               5                   10                  15

Ser Val Lys Met Ser Cys Lys Ala Ser Gly Tyr Thr Phe Ser Ser Phe
            20                  25                  30

Trp Met His Trp Val Lys Gln Arg Pro Gly Gln Gly Leu Glu Trp Ile
        35                  40                  45

Gly Tyr Ile Asn Pro Arg Ser Gly Tyr Thr Glu Cys Asn Glu Ile Phe
    50                  55                  60

Arg Asp Lys Ala Thr Met Thr Ala Asp Thr Ser Ser Thr Ala Tyr
65                  70                  75                  80

Met Gln Leu Ser Gly Leu Thr Ser Glu Asp Ser Ala Val Tyr Tyr Cys
                85                  90                  95

Ala Ser Phe Leu Gly Arg Gly Ala Met Asp Tyr Trp Gly Gln Gly Thr
            100                 105                 110

Ser Val Thr Val Ser Ser
        115

<210> SEQ ID NO 29
<211> LENGTH: 1433
<212> TYPE: DNA
<213> ORGANISM: Artificial
<220> FEATURE:
<223> OTHER INFORMATION: mutated murine immunoglobulin chain
<220> FEATURE:
<221> NAME/KEY: misc_feature
<222> LOCATION: (1)..(1433)
<223> OTHER INFORMATION: "SEQ.ID.No.27".  Complete light chain DNA
      sequence of DI17E6 in pdHL10-DI-17E6y2h(N297Q); (Fig. 17A)

<400> SEQUENCE: 29
atggagttgc ctgttaggct gttggtgctg atgttctgga ttcctggtga ggagagaggg      60
aagtgaggga ggagaatgga cagggagcag gagcactgaa tcccattgct cattccatgt    120
attctggcat gggtgagaag atgggtctta tcctccagca tggggcctct ggggtgaata    180
cttgttagag ggaggttcca gatgggaaca tgtgctataa tgaagattat gaaatggatg    240
cctgggatgg tctaagtaat gcctagaagt gactagacac ttgcaattca cttttttttgg    300 taagaagaga ttttaggct ataaaaaaat gttatgtaaa aataaacatc acagttgaaa    360
taaaaaaaaa tataaggatg ttcatgaatt ttgtgtataa ctatgtattt ctctctcatt    420
gtttcagctt ccttaagcga catccagatg acccagagcc caagcagcct gagcgccagc    480
gtgggtgaca gagtgaccat cacctgtagg gcaagtcagg acattagcaa ttatttagcc    540
tggtaccagc agaagccagg taaggctcca aagctgctga tctactacac atcaaaaatc    600
cactcaggtg tgccaagcag attcagcggt agcggtagcg gtaccgacta caccttcacc    660
atcagcagcc tccagccaga ggacatcgcc acctactact gcaacagggg taatacgttt    720
ccgtacacgt tcggccaagg gaccaaggtg gaaatcaaac gtaagtggat cccgcaattc    780
taaactctga gggggtcgga tgacgtggcc attctttgcc taaagcattg agtttactgc    840
aaggtcagaa aagcatgcaa agccctcaga atggctgcaa agagctccaa caaaacaatt    900
tagaacttta ttaaggaata gggggaagct aggaagaaac tcaaaacatc aagattttaa    960
atacgcttct tggtctccct tgctataatta tctgggataa gcatgctgtt ttctgtctgt   1020
```

```
cectaacatg ccctgtgatt atccgcaaac aacacaccca agggcagaac tttgttactt      1080
aaacaccatc ctgtttgctt ctttcctcag gaactgtggc tgcaccatct gtcttcatct      1140
tcccgccatc tgatgagcag ttgaaatctg gaactgcctc tgttgtgtgc ctgctgaata      1200
acttctatcc cagagaggcc aaagtacagt ggaaggtgga taacgccctc caatcgggta      1260
actcccagga gagtgtcaca gagcaggaca gcaaggacag cacctacagc ctcagcagca      1320
ccctgacgct gagcaaagca gactacgaga aacacaaagt ctacgcctgc gaagtcaccc      1380
atcagggcct gagctcgccc gtcacaaaga gcttcaacag gggagagtgt tag            1433
```

<210> SEQ ID NO 30
<211> LENGTH: 321
<212> TYPE: DNA
<213> ORGANISM: Artificial
<220> FEATURE:
<223> OTHER INFORMATION: mutated murine immunoglobulin chain
<220> FEATURE:
<221> NAME/KEY: CDS
<222> LOCATION: (1)..(321)
<223> OTHER INFORMATION: "SEQ.ID.No.29". Variable light chain DNA
      sequence of DI17E6 (Fig. 17B)

<400> SEQUENCE: 30

```
gac atc cag atg acc cag agc cca agc agc ctg agc gcc agc gtg ggt      48
Asp Ile Gln Met Thr Gln Ser Pro Ser Ser Leu Ser Ala Ser Val Gly
1               5                   10                  15 gac aga gtg acc atc acc tgt agg gca agt cag gac att agc aat tat      96
Asp Arg Val Thr Ile Thr Cys Arg Ala Ser Gln Asp Ile Ser Asn Tyr
            20                  25                  30 tta gcc tgg tac cag cag aag cca ggt aag gct cca aag ctg ctg atc     144
Leu Ala Trp Tyr Gln Gln Lys Pro Gly Lys Ala Pro Lys Leu Leu Ile
        35                  40                  45 tac tac aca tca aaa atc cac tca ggt gtg cca agc aga ttc agc ggt     192
Tyr Tyr Thr Ser Lys Ile His Ser Gly Val Pro Ser Arg Phe Ser Gly
    50                  55                  60 agc ggt agc ggt acc gac tac acc ttc acc atc agc agc ctc cag cca     240
Ser Gly Ser Gly Thr Asp Tyr Thr Phe Thr Ile Ser Ser Leu Gln Pro
65                  70                  75                  80 gag gac atc gcc acc tac tac tgc caa cag ggt aat acg ttt ccg tac     288
Glu Asp Ile Ala Thr Tyr Tyr Cys Gln Gln Gly Asn Thr Phe Pro Tyr
                85                  90                  95 acg ttc ggc caa ggg acc aag gtg gaa atc aaa                         321
Thr Phe Gly Gln Gly Thr Lys Val Glu Ile Lys
                100                 105
```

<210> SEQ ID NO 31
<211> LENGTH: 107
<212> TYPE: PRT
<213> ORGANISM: Artificial
<220> FEATURE:
<223> OTHER INFORMATION: Synthetic Construct

<400> SEQUENCE: 31

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Thr Ser Lys Ile His Ser Gly Val Pro Ser Arg Phe Ser Gly
    50                  55                  60
```

```
Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Gly Asn Thr Phe Pro Tyr
                 85                  90                  95

Thr Phe Gly Gln Gly Thr Lys Val Glu Ile Lys
            100                 105
```

<210> SEQ ID NO 32
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: "SEQ.ID.No.31".  human constant light chain
      DNA sequence of DI17E6 (Fig. 17C)

<400> SEQUENCE: 32

```
cga act gtg gct gca cca tct gtc ttc atc ttc ccg cca tct gat gag      48
Arg Thr Val Ala Ala Pro Ser Val Phe Ile Phe Pro Pro Ser Asp Glu
 1               5                  10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
             20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
         35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
     50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
 65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                 85                  90                  95 ccc gtc aca aag agc ttc aac agg gga gag tgt                         321
Pro Val Thr Lys Ser Phe Asn Arg Gly Glu Cys
            100                 105
```

<210> SEQ ID NO 33
<211> LENGTH: 107
<212> TYPE: PRT
<213> ORGANISM: Homo sapiens

<400> SEQUENCE: 33

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

| | |
|---|---|
| <210> SEQ ID NO 34 | |
| <211> LENGTH: 2611 | |
| <212> TYPE: DNA | |
| <213> ORGANISM: Artificial | |
| <220> FEATURE: | |
| <223> OTHER INFORMATION: mutated murine immunoglobulin chain | |
| <220> FEATURE: | |
| <221> NAME/KEY: misc_feature | |
| <222> LOCATION: (1)..(2611) | |
| <223> OTHER INFORMATION: "SEQ.ID.No.33." Complete heavy chain DNA sequence of DI17E6 in pdHL10-DI-17E6γ2h(N297Q), (Fig. 18A) | |

<400> SEQUENCE: 34

```
atggagttgc ctgttaggct gttggtgctg atgttctgga ttcctggtga ggagagaggg      60
aagtgaggga ggagaatgga cagggagcag gagcactgaa tcccattgct cattccatgt     120
attctggcat gggtgagaag atgggtctta tcctccagca tggggcctct ggggtgaata     180
cttgttagag ggaggttcca gatgggaaca tgtgctataa tgaagattat gaaatggatg     240
cctgggatgg tctaagtaat gcctagaagt gactagacac ttgcaattca cttttttgg      300
taagaagaga ttttaggct ataaaaaaat gttatgtaaa aataaacatc acagttgaaa      360
taaaaaaaa tataaggatg ttcatgaatt ttgtgtataa ctatgtattt ctctctcatt      420
gtttcagctt ccttaagcca ggtccagctt cagcagtctg ggggcgaact ggccaagcct     480
ggggcctcag tgaaggtgtc ctgcaaggct tctggctaca cctttagtag tttctggatg     540
cactgggtaa acaggcccc tggacagggt ctggaatgga ttggatacat taatcctaga     600
tctggtttata ctgagtataa tgagatattc agggacaagg ccacaatgac taccgacacc     660
tccaccagca cagcctacat ggagctgagt agcctgagat ctgaggacac cgcagtctat     720
tactgtgcaa gttttctggg acgaggggct atggactact ggggtcaagg aaccaccgtc     780
accgtctcct caggtgagta agcttctgg ggcgagccgg gcctgacttt ggctttgggg     840
cagggagtgg gctaaggtga ggcaggtggc ccagccagg tgcacaccca atgcccgtga     900
gcccagacac tggaccctgc ctggaccctc gtggatagac aagaaccgag gggcctctgc     960
gcctgggccc agctctgtcc acaccgcgg tcacatggca ccacctctct tgcagcctcc    1020
accaagggcc catcggtctt cccctggcg ccctgctcca ggagcacctc cgagagcaca    1080
gcggccctgg gctgcctggt caaggactac ttccccgaac cggtgacggt gtcgtggaac    1140
tcaggcgctc tgaccagcgg cgtgcacacc ttcccagctg tcctacagtc ctcaggactc    1200
tactccctca gcagcgtggt gaccgtgccc tccagcaact tcggcaccca gacctacacc    1260
tgcaacgtag atcacaagcc cagcaacacc aaggtggaca gacagttgg tgagaggcca    1320
gctcagggag ggagggtgtc tgctggaagc caggctcagc cctcctgcct ggacgcaccc    1380
cggctgtgca gccccagccc agggcagcaa ggcaggcccc atctgtctcc tcacccggag    1440
gcctctgccc gccccactca tgctcaggga gagggtcttc tggcttttc caccaggctc    1500
caggcaggca caggctgggt gcccctaccc caggcccttc acacacaggg gcaggtgctt    1560
ggctcagacc tgccaaaagc catatccggg aggaccctgc ccctgaccta gccgaccccc    1620
aaaggccaaa ctgtccactc cctcagctcg gacaccttct ctcctcccag atccgagtaa    1680
ctcccaatct tctctctgca gagcccaaat cttctgacaa aactcacaca tgcccaccgt    1740
gcccaggtaa gccagcccag gcctcgccct ccagctcaag cgggacagg tgccctagag    1800
tagcctgcat ccagggacag gccccagctg gtgctgaca cgtccacctc catctcttcc    1860
tcagcaccac ctgtggcagg accgtcagtc ttcctcttcc cccaaaaacc caaggacacc    1920
ctcatgatct cccggacccc tgaggtcacg tgcgtggtgg tggacgtgag ccacgaagac    1980
```

```
cccgaggtcc agttcaactg gtacgtggac ggcgtggagg tgcataatgc caagacaaag    2040
ccacgggagg agcaggccca gagcacgttc cgtgtggtca gcgtcctcac cgttgtgcac    2100
caggactggc tgaacggcaa ggagtacaag tgcaaggtct ccaacaaagg cctcccagcc    2160
cccatcgaga aaccatctc caaaaccaaa ggtgggaccc cgcggggtat gagggccaca    2220
ggacagaggc cggctcggcc caccctctgc cctgagagtg accgctgtac caacctctgt    2280
ccctacaggg cagccccgag aaccacaggt gtacaccctg cccccatcac gggaggagat    2340
gaccaagaac caggtcagcc tgacctgcct ggtcaaaggc ttctacccca gcgacatcgc    2400
cgtggagtgg gagagcaatg ggcagccgga gaacaactac aagaccacac ctcccatgct    2460
ggactccgac ggctccttct cctctacag caagctcacc gtggacaaga gcaggtggca    2520
gcagggaaac gtcttctcat gctccgtgat gcatgaggct ctgcacaacc actacacaca    2580
gaagagcctc tccctgtccc cgggtaaatg a                                   2611

<210> SEQ ID NO 35
<211> LENGTH: 354
<212> TYPE: DNA
<213> ORGANISM: Artificial
<220> FEATURE:
<223> OTHER INFORMATION: mutated murine immunoglobulin chain
<220> FEATURE:
<221> NAME/KEY: CDS
<222> LOCATION: (1)..(354)
<223> OTHER INFORMATION: "SEQ.ID.No.35". Variable heavy chain DNA
      sequence of DI17E6, (Fig. 18B)

<400> SEQUENCE: 35 cag gtc cag ctt cag cag tct ggg ggc gaa ctg gcc aag cct ggg gcc      48
Gln Val Gln Leu Gln Gln Ser Gly Gly Glu Leu Ala Lys Pro Gly Ala
1               5                   10                  15 tca gtg aag gtg tcc tgc aag gct tct ggc tac acc ttt agt agt ttc      96
Ser Val Lys Val Ser Cys Lys Ala Ser Gly Tyr Thr Phe Ser Ser Phe
            20                  25                  30 tgg atg cac tgg gta aga cag gcc cct gga cag ggt ctg gaa tgg att     144
Trp Met His Trp Val Arg Gln Ala Pro Gly Gln Gly Leu Glu Trp Ile
        35                  40                  45 gga tac att aat cct aga tct ggt tat act gag tat aat gag ata ttc     192
Gly Tyr Ile Asn Pro Arg Ser Gly Tyr Thr Glu Tyr Asn Glu Ile Phe
    50                  55                  60 agg gac aag gcc aca atg act acc gac acc tcc acc agc aca gcc tac     240
Arg Asp Lys Ala Thr Met Thr Thr Asp Thr Ser Thr Ser Thr Ala Tyr
65                  70                  75                  80 atg gag ctg agt agc ctg aga tct gag gac acc gca gtc tat tac tgt     288
Met Glu Leu Ser Ser Leu Arg Ser Glu Asp Thr Ala Val Tyr Tyr Cys
                85                  90                  95 gca agt ttt ctg gga cga ggg gct atg gac tac tgg ggt caa gga acc     336
Ala Ser Phe Leu Gly Arg Gly Ala Met Asp Tyr Trp Gly Gln Gly Thr
            100                 105                 110 acc gtc acc gtc tcc tca                                              354
Thr Val Thr Val Ser Ser
        115

<210> SEQ ID NO 36
<211> LENGTH: 118
<212> TYPE: PRT
<213> ORGANISM: Artificial
<220> FEATURE:
<223> OTHER INFORMATION: Synthetic Construct

<400> SEQUENCE: 36

Gln Val Gln Leu Gln Gln Ser Gly Gly Glu Leu Ala Lys Pro Gly Ala
```

```
                1               5                   10                  15
              Ser Val Lys Val Ser Cys Lys Ala Ser Gly Tyr Thr Phe Ser Ser Phe
                            20                  25                  30

Trp Met His Trp Val Arg Gln Ala Pro Gly Gln Gly Leu Glu Trp Ile
                            35                  40                  45

Gly Tyr Ile Asn Pro Arg Ser Gly Tyr Thr Glu Tyr Asn Glu Ile Phe
                            50                  55                  60

Arg Asp Lys Ala Thr Met Thr Thr Asp Thr Ser Thr Ser Thr Ala Tyr
               65                  70                  75                  80

Met Glu Leu Ser Ser Leu Arg Ser Glu Asp Thr Ala Val Tyr Tyr Cys
                            85                  90                  95

Ala Ser Phe Leu Gly Arg Gly Ala Met Asp Tyr Trp Gly Gln Gly Thr
                            100                 105                 110

Thr Val Thr Val Ser Ser
                            115

<210> SEQ ID NO 37
<211> LENGTH: 987
<212> TYPE: DNA
<213> ORGANISM: Homo sapiens
<220> FEATURE:
<221> NAME/KEY: CDS
<222> LOCATION: (1)..(987)
<223> OTHER INFORMATION: "SEQ.ID.No. 37".   human constant heavy chain
      DNA sequence of DI17E6 (Fig. 18C)

<400> SEQUENCE: 37 gcc tcc acc aag ggc cca tcg gtc ttc ccc ctg gcg ccc tgc tcc agg         48
Ala Ser Thr Lys Gly Pro Ser Val Phe Pro Leu Ala Pro Cys Ser Arg
 1               5                   10                  15 agc acc tcc gag agc aca gcg gcc ctg ggc tgc ctg gtc aag gac tac         96
Ser Thr Ser Glu Ser Thr Ala Ala Leu Gly Cys Leu Val Lys Asp Tyr
              20                  25                  30 ttc ccc gaa ccg gtg acg gtg tcg tgg aac tca ggc gct ctg acc agc        144
Phe Pro Glu Pro Val Thr Val Ser Trp Asn Ser Gly Ala Leu Thr Ser
         35                  40                  45 ggc gtg cac acc ttc cca gct gtc cta cag tcc tca gga ctc tac tcc        192
Gly Val His Thr Phe Pro Ala Val Leu Gln Ser Ser Gly Leu Tyr Ser
     50                  55                  60 ctc agc agc gtg gtg acc gtg ccc tcc agc aac ttc ggc acc cag acc        240
Leu Ser Ser Val Val Thr Val Pro Ser Ser Asn Phe Gly Thr Gln Thr
 65                  70                  75                  80 tac acc tgc aac gta gat cac aag ccc agc aac acc aag gtg gac aag        288
Tyr Thr Cys Asn Val Asp His Lys Pro Ser Asn Thr Lys Val Asp Lys
                 85                  90                  95 aca gtt gag ccc aaa tct tct gac aaa act cac aca tgc cca ccg tgc        336
Thr Val Glu Pro Lys Ser Ser Asp Lys Thr His Thr Cys Pro Pro Cys
             100                 105                 110 cca gca cca cct gtg gca gga ccg tca gtc ttc ctc ttc ccc cca aaa        384
Pro Ala Pro Pro Val Ala Gly Pro Ser Val Phe Leu Phe Pro Pro Lys
         115                 120                 125 ccc aag gac acc ctc atg atc tcc cgg acc cct gag gtc acg tgc gtg        432
Pro Lys Asp Thr Leu Met Ile Ser Arg Thr Pro Glu Val Thr Cys Val
     130                 135                 140 gtg gtg gac gtg agc cac gaa gac ccc gag gtc cag ttc aac tgg tac        480
Val Val Asp Val Ser His Glu Asp Pro Glu Val Gln Phe Asn Trp Tyr
145                 150                 155                 160 gtg gac ggc gtg gag gtg cat aat gcc aag aca aag cca cgg gag gag        528
Val Asp Gly Val Glu Val His Asn Ala Lys Thr Lys Pro Arg Glu Glu
                 165                 170                 175
```

```
cag gcc cag agc acg ttc cgt gtg gtc agc gtc ctc acc gtt gtg cac      576
Gln Ala Gln Ser Thr Phe Arg Val Val Ser Val Leu Thr Val Val His
            180                 185                 190 cag gac tgg ctg aac ggc aag gag tac aag tgc aag gtc tcc aac aaa      624
Gln Asp Trp Leu Asn Gly Lys Glu Tyr Lys Cys Lys Val Ser Asn Lys
        195                 200                 205 ggc ctc cca gcc ccc atc gag aaa acc atc tcc aaa acc aaa ggg cag      672
Gly Leu Pro Ala Pro Ile Glu Lys Thr Ile Ser Lys Thr Lys Gly Gln
    210                 215                 220 ccc cga gaa cca cag gtg tac acc ctg ccc cca tca cgg gag gag atg      720
Pro Arg Glu Pro Gln Val Tyr Thr Leu Pro Pro Ser Arg Glu Glu Met
225                 230                 235                 240 acc aag aac cag gtc agc ctg acc tgc ctg gtc aaa ggc ttc tac ccc      768
Thr Lys Asn Gln Val Ser Leu Thr Cys Leu Val Lys Gly Phe Tyr Pro
                245                 250                 255 agc gac atc gcc gtg gag tgg gag agc aat ggg cag ccg gag aac aac      816
Ser Asp Ile Ala Val Glu Trp Glu Ser Asn Gly Gln Pro Glu Asn Asn
            260                 265                 270 tac aag acc aca cct ccc atg ctg gac tcc gac ggc tcc ttc ttc ctc      864
Tyr Lys Thr Thr Pro Pro Met Leu Asp Ser Asp Gly Ser Phe Phe Leu
        275                 280                 285 tac agc aag ctc acc gtg gac aag agc agg tgg cag cag ggg aac gtc      912
Tyr Ser Lys Leu Thr Val Asp Lys Ser Arg Trp Gln Gln Gly Asn Val
    290                 295                 300 ttc tca tgc tcc gtg atg cat gag gct ctg cac aac cac tac aca cag      960
Phe Ser Cys Ser Val Met His Glu Ala Leu His Asn His Tyr Thr Gln
305                 310                 315                 320 aag agc ctc tcc ctg tcc ccg ggt aaa                                  987
Lys Ser Leu Ser Leu Ser Pro Gly Lys
                325

<210> SEQ ID NO 38
<211> LENGTH: 329
<212> TYPE: PRT
<213> ORGANISM: Homo sapiens

<400> SEQUENCE: 38

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Ser Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175
```

```
Gln Ala Gln Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
            195                 200                 205

Gly Leu Pro Ala Pro Ile Glu Lys Thr Ile Ser Lys Thr Lys Gly Gln
        210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
            275                 280                 285

Tyr Ser Lys Leu Thr Val Asp Lys Ser Arg Trp Gln Gln Gly Asn Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325

<210> SEQ ID NO 39
<211> LENGTH: 45
<212> TYPE: DNA
<213> ORGANISM: Artificial
<220> FEATURE:
<223> OTHER INFORMATION: mutated murine immunoglobulin chain (portion)
<220> FEATURE:
<221> NAME/KEY: CDS
<222> LOCATION: (1)..(45)
<223> OTHER INFORMATION: "SEQ ID No. 39:".   DNA sequence of modified
      IgG1 hinge region DI17E6 (Fig. 18D)

<400> SEQUENCE: 39 gag ccc aaa tct tct gac aaa act cac aca tgc cca ccg tgc cca        45
Glu Pro Lys Ser Ser Asp Lys Thr His Thr Cys Pro Pro Cys Pro
1               5                   10                  15

<210> SEQ ID NO 40
<211> LENGTH: 15
<212> TYPE: PRT
<213> ORGANISM: Artificial
<220> FEATURE:
<223> OTHER INFORMATION: Synthetic Construct

<400> SEQUENCE: 40

Glu Pro Lys Ser Ser Asp Lys Thr His Thr Cys Pro Pro Cys Pro
1               5                   10                  15

<210> SEQ ID NO 41
<211> LENGTH: 15
<212> TYPE: PRT
<213> ORGANISM: Artificial
<220> FEATURE:
<223> OTHER INFORMATION: mutated murine immunoglobulin chain (portion)
<220> FEATURE:
<221> NAME/KEY: CHAIN
<222> LOCATION: (1)..(15)
<223> OTHER INFORMATION: "SEQ.ID.No.40".   modified IgG1 hinge region
      DI17E6

<400> SEQUENCE: 41

Glu Pro Lys Ser Ser Asp Lys Thr His Thr Cys Pro Pro Cys Pro
1               5                   10                  15
```

```
<210> SEQ ID NO 42
<211> LENGTH: 1341
<212> TYPE: DNA
<213> ORGANISM: Artificial
<220> FEATURE:
<223> OTHER INFORMATION: mutated murine immunoglobulin chain
<220> FEATURE:
<221> NAME/KEY: CDS
<222> LOCATION: (1)..(1341)
<223> OTHER INFORMATION: "SEQ.ID.No.41".  Complete heavy chain DNA
      sequence of DI17E6 (Fig. 19A)

<400> SEQUENCE: 42
```

| | | | | | | | | | | | | | | | | |
|---|---|---|---|---|---|---|---|---|---|---|---|---|---|---|---|---|
| cag | gtc | cag | ctt | cag | cag | tct | ggg | ggc | gaa | ctg | gcc | aag | cct | ggg | gcc | 48 |
| Gln | Val | Gln | Leu | Gln | Gln | Ser | Gly | Gly | Glu | Leu | Ala | Lys | Pro | Gly | Ala | |
| 1 | | | | 5 | | | | | 10 | | | | | 15 | | |
| tca | gtg | aag | gtg | tcc | tgc | aag | gct | tct | ggc | tac | acc | ttt | agt | agt | ttc | 96 |
| Ser | Val | Lys | Val | Ser | Cys | Lys | Ala | Ser | Gly | Tyr | Thr | Phe | Ser | Ser | Phe | |
| | | | 20 | | | | | 25 | | | | | 30 | | | |
| tgg | atg | cac | tgg | gta | aga | cag | gcc | cct | gga | cag | ggt | ctg | gaa | tgg | att | 144 |
| Trp | Met | His | Trp | Val | Arg | Gln | Ala | Pro | Gly | Gln | Gly | Leu | Glu | Trp | Ile | |
| | | 35 | | | | | 40 | | | | | 45 | | | | |
| gga | tac | att | aat | cct | aga | tct | ggt | tat | act | gag | tat | aat | gag | ata | ttc | 192 |
| Gly | Tyr | Ile | Asn | Pro | Arg | Ser | Gly | Tyr | Thr | Glu | Tyr | Asn | Glu | Ile | Phe | |
| | 50 | | | | | 55 | | | | | 60 | | | | | |
| agg | gac | aag | gcc | aca | atg | act | acc | gac | acc | tcc | acc | agc | aca | gcc | tac | 240 |
| Arg | Asp | Lys | Ala | Thr | Met | Thr | Thr | Asp | Thr | Ser | Thr | Ser | Thr | Ala | Tyr | |
| 65 | | | | | 70 | | | | | 75 | | | | | 80 | |
| atg | gag | ctg | agt | agc | ctg | aga | tct | gag | gac | acc | gca | gtc | tat | tac | tgt | 288 |
| Met | Glu | Leu | Ser | Ser | Leu | Arg | Ser | Glu | Asp | Thr | Ala | Val | Tyr | Tyr | Cys | |
| | | | | 85 | | | | | 90 | | | | | 95 | | |
| gca | agt | ttt | ctg | gga | cga | ggg | gct | atg | gac | tac | tgg | ggt | caa | gga | acc | 336 |
| Ala | Ser | Phe | Leu | Gly | Arg | Gly | Ala | Met | Asp | Tyr | Trp | Gly | Gln | Gly | Thr | |
| | | | 100 | | | | | 105 | | | | | 110 | | | |
| acc | gtc | acc | gtc | tcc | tca | gcc | tcc | acc | aag | ggc | cca | tcg | gtc | ttc | ccc | 384 |
| Thr | Val | Thr | Val | Ser | Ser | Ala | Ser | Thr | Lys | Gly | Pro | Ser | Val | Phe | Pro | |
| | | 115 | | | | | 120 | | | | | 125 | | | | |
| ctg | gcg | ccc | tgc | tcc | agg | agc | acc | tcc | gag | agc | aca | gcg | gcc | ctg | ggc | 432 |
| Leu | Ala | Pro | Cys | Ser | Arg | Ser | Thr | Ser | Glu | Ser | Thr | Ala | Ala | Leu | Gly | |
| | 130 | | | | | 135 | | | | | 140 | | | | | |
| tgc | ctg | gtc | aag | gac | tac | ttc | ccc | gaa | ccg | gtg | acg | gtg | tcg | tgg | aac | 480 |
| Cys | Leu | Val | Lys | Asp | Tyr | Phe | Pro | Glu | Pro | Val | Thr | Val | Ser | Trp | Asn | |
| 145 | | | | | 150 | | | | | 155 | | | | | 160 | |
| tca | ggc | gct | ctg | acc | agc | ggc | gtg | cac | acc | ttc | cca | gct | gtc | cta | cag | 528 |
| Ser | Gly | Ala | Leu | Thr | Ser | Gly | Val | His | Thr | Phe | Pro | Ala | Val | Leu | Gln | |
| | | | | 165 | | | | | 170 | | | | | 175 | | |
| tcc | tca | gga | ctc | tac | tcc | ctc | agc | agc | gtg | gtg | acc | gtg | ccc | tcc | agc | 576 |
| Ser | Ser | Gly | Leu | Tyr | Ser | Leu | Ser | Ser | Val | Val | Thr | Val | Pro | Ser | Ser | |
| | | | 180 | | | | | 185 | | | | | 190 | | | |
| aac | ttc | ggc | acc | cag | acc | tac | acc | tgc | aac | gta | gat | cac | aag | ccc | agc | 624 |
| Asn | Phe | Gly | Thr | Gln | Thr | Tyr | Thr | Cys | Asn | Val | Asp | His | Lys | Pro | Ser | |
| | | 195 | | | | | 200 | | | | | 205 | | | | |
| aac | acc | aag | gtg | gac | aag | aca | gtt | gag | ccc | aaa | tct | tct | gac | aaa | act | 672 |
| Asn | Thr | Lys | Val | Asp | Lys | Thr | Val | Glu | Pro | Lys | Ser | Ser | Asp | Lys | Thr | |
| | 210 | | | | | 215 | | | | | 220 | | | | | |
| cac | aca | tgc | cca | ccg | tgc | cca | gca | cca | cct | gtg | gca | gga | ccg | tca | gtc | 720 |
| His | Thr | Cys | Pro | Pro | Cys | Pro | Ala | Pro | Pro | Val | Ala | Gly | Pro | Ser | Val | |
| 225 | | | | | 230 | | | | | 235 | | | | | 240 | |
| ttc | ctc | ttc | ccc | cca | aaa | ccc | aag | gac | acc | ctc | atg | atc | tcc | cgg | acc | 768 |
| Phe | Leu | Phe | Pro | Pro | Lys | Pro | Lys | Asp | Thr | Leu | Met | Ile | Ser | Arg | Thr | |
| | | | | 245 | | | | | 250 | | | | | 255 | | |

```
cct gag gtc acg tgc gtg gtg gtg gac gtg agc cac gaa gac ccc gag    816
Pro Glu Val Thr Cys Val Val Val Asp Val Ser His Glu Asp Pro Glu
        260                 265                 270 gtc cag ttc aac tgg tac gtg gac ggc gtg gag gtg cat aat gcc aag    864
Val Gln Phe Asn Trp Tyr Val Asp Gly Val Glu Val His Asn Ala Lys
    275                 280                 285 aca aag cca cgg gag gag cag gcc cag agc acg ttc cgt gtg gtc agc    912
Thr Lys Pro Arg Glu Glu Gln Ala Gln Ser Thr Phe Arg Val Val Ser
290                 295                 300 gtc ctc acc gtt gtg cac cag gac tgg ctg aac ggc aag gag tac aag    960
Val Leu Thr Val Val His Gln Asp Trp Leu Asn Gly Lys Glu Tyr Lys
305                 310                 315                 320 tgc aag gtc tcc aac aaa ggc ctc cca gcc ccc atc gag aaa acc atc   1008
Cys Lys Val Ser Asn Lys Gly Leu Pro Ala Pro Ile Glu Lys Thr Ile
                325                 330                 335 tcc aaa acc aaa ggg cag ccc cga gaa cca cag gtg tac acc ctg ccc   1056
Ser Lys Thr Lys Gly Gln Pro Arg Glu Pro Gln Val Tyr Thr Leu Pro
            340                 345                 350 cca tca cgg gag gag atg acc aag aac cag gtc agc ctg acc tgc ctg   1104
Pro Ser Arg Glu Glu Met Thr Lys Asn Gln Val Ser Leu Thr Cys Leu
        355                 360                 365 gtc aaa ggc ttc tac ccc agc gac atc gcc gtg gag tgg gag agc aat   1152
Val Lys Gly Phe Tyr Pro Ser Asp Ile Ala Val Glu Trp Glu Ser Asn
370                 375                 380 ggg cag ccg gag aac aac tac aag acc aca cct ccc atg ctg gac tcc   1200
Gly Gln Pro Glu Asn Asn Tyr Lys Thr Thr Pro Pro Met Leu Asp Ser
385                 390                 395                 400 gac ggc tcc ttc ttc ctc tac agc aag ctc acc gtg gac aag agc agg   1248
Asp Gly Ser Phe Phe Leu Tyr Ser Lys Leu Thr Val Asp Lys Ser Arg
                405                 410                 415 tgg cag cag ggg aac gtc ttc tca tgc tcc gtg atg cat gag gct ctg   1296
Trp Gln Gln Gly Asn Val Phe Ser Cys Ser Val Met His Glu Ala Leu
            420                 425                 430 cac aac cac tac aca cag aag agc ctc tcc ctg tcc ccg ggt aaa       1341
His Asn His Tyr Thr Gln Lys Ser Leu Ser Leu Ser Pro Gly Lys
        435                 440                 445

<210> SEQ ID NO 43
<211> LENGTH: 447
<212> TYPE: PRT
<213> ORGANISM: Artificial
<220> FEATURE:
<223> OTHER INFORMATION: Synthetic Construct

<400> SEQUENCE: 43

Gln Val Gln Leu Gln Gln Ser Gly Gly Glu Leu Ala Lys Pro Gly Ala
1               5                   10                  15

Ser Val Lys Val Ser Cys Lys Ala Ser Gly Tyr Thr Phe Ser Ser Phe
            20                  25                  30

Trp Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Glu Ile Phe
    50                  55                  60

Arg Asp Lys Ala Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Phe Leu Gly Arg Gly Ala Met Asp Tyr Trp Gly Gln Gly Thr
            100                 105                 110

Thr Val Thr Val Ser Ser Ala Ser Thr Lys Gly Pro Ser Val Phe Pro
```

```
                115                 120                 125
Leu Ala Pro Cys Ser Arg Ser Thr Ser Glu Ser Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
        180                 185                 190
Asn Phe Gly Thr Gln Thr Tyr Thr Cys Asn Val Asp His Lys Pro Ser
                195                 200                 205
Asn Thr Lys Val Asp Lys Thr Val Glu Pro Lys Ser Ser Asp Lys Thr
210                 215                 220
His Thr Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
        260                 265                 270
Val Gln Phe Asn Trp Tyr Val Asp Gly Val Glu Val His Asn Ala Lys
                275                 280                 285
Thr Lys Pro Arg Glu Glu Gln Ala Gln Ser Thr Phe Arg Val Val Ser
        290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ala Pro Ile Glu Lys Thr Ile
                325                 330                 335
Ser Lys Thr Lys Gly Gln Pro Arg Glu Pro Gln Val Tyr Thr Leu Pro
        340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
        420                 425                 430
His Asn His Tyr Thr Gln Lys Ser Leu Ser Leu Ser Pro Gly Lys
        435                 440                 445

<210> SEQ ID NO 44
<211> LENGTH: 642
<212> TYPE: DNA
<213> ORGANISM: Artificial
<220> FEATURE:
<223> OTHER INFORMATION: mutated murine immunoglobulin chain
<220> FEATURE:
<221> NAME/KEY: CDS
<222> LOCATION: (1)..(642)
<223> OTHER INFORMATION: "SEQ.ID.No.43". Complete light chain DNA
      sequence of DI17E6 (Fig. 19B)

<400> SEQUENCE: 44 gac atc cag atg acc cag agc cca agc agc ctg agc gcc agc gtg ggt    48
Asp Ile Gln Met Thr Gln Ser Pro Ser Ser Leu Ser Ala Ser Val Gly
1               5                   10                  15
```

```
gac aga gtg acc atc acc tgt agg gca agt cag gac att agc aat tat    96
Asp Arg Val Thr Ile Thr Cys Arg Ala Ser Gln Asp Ile Ser Asn Tyr
         20                  25                  30 tta gcc tgg tac cag cag aag cca ggt aag gct cca aag ctg ctg atc   144
Leu Ala Trp Tyr Gln Gln Lys Pro Gly Lys Ala Pro Lys Leu Leu Ile
 35                  40                  45 tac tac aca tca aaa atc cac tca ggt gtg cca agc aga ttc agc ggt   192
Tyr Tyr Thr Ser Lys Ile His Ser Gly Val Pro Ser Arg Phe Ser Gly
 50                  55                  60 agc ggt agc ggt acc gac tac acc ttc acc atc agc agc ctc cag cca   240
Ser Gly Ser Gly Thr Asp Tyr Thr Phe Thr Ile Ser Ser Leu Gln Pro
65                   70                  75                  80 gag gac atc gcc acc tac tac tgc caa cag ggt aat acg ttt ccg tac   288
Glu Asp Ile Ala Thr Tyr Tyr Cys Gln Gln Gly Asn Thr Phe Pro Tyr
                 85                  90                  95 acg ttc ggc caa ggg acc aag gtg gaa atc aaa cga act gtg gct gca   336
Thr Phe Gly Gln Gly Thr Lys Val Glu Ile Lys Arg Thr Val Ala Ala
                100                 105                 110 cca tct gtc ttc atc ttc ccg cca tct gat gag cag ttg aaa tct gga   384
Pro Ser Val Phe Ile Phe Pro Pro Ser Asp Glu Gln Leu Lys Ser Gly
            115                 120                 125 act gcc tct gtt gtg tgc ctg ctg aat aac ttc tat ccc aga gag gcc   432
Thr Ala Ser Val Val Cys Leu Leu Asn Asn Phe Tyr Pro Arg Glu Ala
130                 135                 140 aaa gta cag tgg aag gtg gat aac gcc ctc caa tcg ggt aac tcc cag   480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc   528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac   576
Ser Thr Leu Thr Leu Ser Lys Ala Asp Tyr Glu Lys His Lys Val Tyr
                180                 185                 190 gcc tgc gaa gtc acc cat cag ggc ctg agc tcg ccc gtc aca aag agc   624
Ala Cys Glu Val Thr His Gln Gly Leu Ser Ser Pro Val Thr Lys Ser
            195                 200                 205 ttc aac agg gga gag tgt                                           642
Phe Asn Arg Gly Glu Cys
        210

<210> SEQ ID NO 45
<211> LENGTH: 214
<212> TYPE: PRT
<213> ORGANISM: Artificial
<220> FEATURE:
<223> OTHER INFORMATION: Synthetic Construct

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
         35                  40                  45

Tyr Tyr Thr Ser Lys Ile His Ser Gly Val Pro Ser Arg Phe Ser Gly
 50                  55                  60

Ser Gly Ser Gly Thr Asp Tyr Thr Phe Thr Ile Ser Ser Leu Gln Pro
65                   70                  75                  80

Glu Asp Ile Ala Thr Tyr Tyr Cys Gln Gln Gly Asn Thr Phe Pro Tyr
                 85                  90                  95
```

```
                Thr Phe Gly Gln Gly Thr Lys Val Glu Ile Lys Arg Thr Val Ala Ala
                            100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
                145                 150                 155                 160

Glu Ser Val Thr Glu Gln Asp Ser Lys Asp Ser Thr Tyr Ser Leu Ser
                                165                 170                 175

Ser Thr Leu Thr Leu Ser Lys Ala Asp Tyr Glu Lys His Lys Val Tyr
                            180                 185                 190

Ala Cys Glu Val Thr His Gln Gly Leu Ser Ser Pro Val Thr Lys Ser
                        195                 200                 205

Phe Asn Arg Gly Glu Cys
                    210

<210> SEQ ID NO 46
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 46

Leu Gly Asp Arg Val Ile Ile Ser Cys
1               5

<210> SEQ ID NO 47
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 47

Val Ile Ile Ser Cys Arg Ala Ser Gln
1               5

<210> SEQ ID NO 48
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 48

Ile Ile Ser Cys Arg Ala Ser Gln Asp
1               5

<210> SEQ ID NO 49
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 49

Ile Ser Cys Arg Ala Ser Gln Asp Ile
1               5
```

```
<210> SEQ ID NO 50
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 50

Ile Ser Asn Tyr Leu Ser Trp Tyr Gln
1               5

<210> SEQ ID NO 51
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 51

Leu Ser Trp Tyr Gln Gln Lys Pro Asp
1               5

<210> SEQ ID NO 52
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 52

Val Lys Leu Leu Ile Phe Tyr Thr Ser
1               5

<210> SEQ ID NO 53
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 53

Leu Leu Ile Phe Tyr Thr Ser Lys Leu
1               5

<210> SEQ ID NO 54
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 54

Leu Ile Phe Tyr Thr Ser Lys Leu His
1               5

<210> SEQ ID NO 55
<211> LENGTH: 9
<212> TYPE: PRT
<213> ORGANISM: Mus musculus
<220> FEATURE:
<221> NAME/KEY: PEPTIDE
<222> LOCATION: (1)..(9)
```

```
<400> SEQUENCE: 55

Ile Phe Tyr Thr Ser Lys Leu His Ser
1               5

<210> SEQ ID NO 56
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 56

Tyr Thr Ser Lys Leu His Ser Gly Val
1               5

<210> SEQ ID NO 57
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 57

Leu His Ser Gly Val Pro Ser Arg Phe
1               5

<210> SEQ ID NO 58
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 58

Tyr Ser Leu Thr Ile Ser Asn Leu Asp
1               5

<210> SEQ ID NO 59
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 59

Ile Ala Thr Tyr Phe Cys Gln Gln Gly
1               5

<210> SEQ ID NO 60
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 60

Tyr Phe Cys Gln Gln Gly Asn Thr Phe
1               5

<210> SEQ ID NO 61
<211> LENGTH: 9
<212> TYPE: PRT
<213> ORGANISM: Mus musculus
```

```
<220> FEATURE:
<221> NAME/KEY: PEPTIDE
<222> LOCATION: (1)..(9)

<400> SEQUENCE: 61

Phe Gly Gly Gly Thr Lys Val Glu Met
1               5

<210> SEQ ID NO 62
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 62

Val Gly Asp Arg Val Thr Ile Thr Cys
1               5

<210> SEQ ID NO 63
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 63

Val Thr Ile Thr Cys Arg Ala Ser Gln
1               5

<210> SEQ ID NO 64
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 64

Ile Thr Cys Arg Ala Ser Gln Asp Ile
1               5

<210> SEQ ID NO 65
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 65

Ile Ser Asn Tyr Leu Ala Trp Tyr Gln
1               5

<210> SEQ ID NO 66
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 66

Leu Leu Ile Tyr Tyr Thr Ser Lys Ile
1               5
```

```
<210> SEQ ID NO 67
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 67

Leu Ile Tyr Tyr Thr Ser Lys Ile His
1               5

<210> SEQ ID NO 68
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 68

Ile Tyr Tyr Thr Ser Lys Ile His Ser
1               5

<210> SEQ ID NO 69
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 69

Tyr Tyr Thr Ser Lys Ile His Ser Gly
1               5

<210> SEQ ID NO 70
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 70

Tyr Thr Ser Lys Ile His Ser Gly Val
1               5

<210> SEQ ID NO 71
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 71

Ile His Ser Gly Val Pro Ser Arg Phe
1               5

<210> SEQ ID NO 72
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 72
```

```
Tyr Thr Phe Thr Ile Ser Ser Leu Gln
1               5

<210> SEQ ID NO 73
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 73

Phe Thr Ile Ser Ser Leu Gln Pro Glu
1               5

<210> SEQ ID NO 74
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 74

Ile Ala Thr Tyr Tyr Cys Gln Gln Gly
1               5

<210> SEQ ID NO 75
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 75

Tyr Tyr Cys Gln Gln Gly Asn Thr Phe
1               5

<210> SEQ ID NO 76
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 76

Phe Pro Tyr Thr Phe Gly Gln Gly Thr
1               5

<210> SEQ ID NO 77
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 77

Phe Gly Gln Gly Thr Lys Val Glu Ile
1               5

<210> SEQ ID NO 78
<211> LENGTH: 9
<212> TYPE: PRT
<213> ORGANISM: Mus musculus
<220> FEATURE:
<221> NAME/KEY: PEPTIDE
```

```
<222> LOCATION: (1)..(9)

<400> SEQUENCE: 78

Val Gln Leu Gln Gln Ser Gly Ala Glu
1               5

<210> SEQ ID NO 79
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 79

Leu Gln Gln Ser Gly Ala Glu Leu Ala
1               5

<210> SEQ ID NO 80
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 80

Val Lys Met Ser Cys Lys Ala Ser Gly
1               5

<210> SEQ ID NO 81
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 81

Tyr Thr Phe Ser Ser Phe Trp Met His
1               5

<210> SEQ ID NO 82
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 82

Phe Ser Ser Phe Trp Met His Trp Val
1               5

<210> SEQ ID NO 83
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 83

Phe Trp Met His Trp Val Lys Gln Arg
1               5

<210> SEQ ID NO 84
<211> LENGTH: 9
```

```
<212> TYPE: PRT
<213> ORGANISM: Mus musculus
<220> FEATURE:
<221> NAME/KEY: PEPTIDE
<222> LOCATION: (1)..(9)

<400> SEQUENCE: 84

Trp Met His Trp Val Lys Gln Arg Pro
1               5

<210> SEQ ID NO 85
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 85

Trp Val Lys Gln Arg Pro Gly Gln Gly
1               5

<210> SEQ ID NO 86
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 86

Val Lys Gln Arg Pro Gly Gln Gly Leu
1               5

<210> SEQ ID NO 87
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 87

Trp Ile Gly Tyr Ile Asn Pro Arg Ser
1               5

<210> SEQ ID NO 88
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 88

Ile Gly Tyr Ile Asn Pro Arg Ser Gly
1               5

<210> SEQ ID NO 89
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 89

Ile Asn Pro Arg Ser Gly Tyr Thr Glu
1               5
```

```
<210> SEQ ID NO 90
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 90

Ile Phe Arg Asp Lys Ala Thr Met Thr
1               5

<210> SEQ ID NO 91
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 91

Phe Arg Asp Lys Ala Thr Met Thr Ala
1               5

<210> SEQ ID NO 92
<211> LENGTH: 9
<212> TYPE: PRT
<213> ORGANISM: Mus musculus

<400> SEQUENCE: 92

Tyr Met Gln Leu Ser Gly Leu Thr Ser
1               5

<210> SEQ ID NO 93
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 93

Met Gln Leu Ser Gly Leu Thr Ser Glu
1               5

<210> SEQ ID NO 94
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 94

Leu Ser Gly Leu Thr Ser Glu Asp Ser
1               5

<210> SEQ ID NO 95
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 95

Val Tyr Tyr Cys Ala Ser Phe Leu Gly
```

```
<210> SEQ ID NO 96
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 96

Tyr Tyr Cys Ala Ser Phe Leu Gly Arg
1               5

<210> SEQ ID NO 97
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 97

Phe Leu Gly Arg Gly Ala Met Asp Tyr
1               5

<210> SEQ ID NO 98
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 98

Tyr Trp Gly Gln Gly Thr Ser Val Thr
1               5

<210> SEQ ID NO 99
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 99

Trp Gly Gln Gly Thr Ser Val Thr Val
1               5

<210> SEQ ID NO 100
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 100

Val Gln Leu Gln Gln Ser Gly Gly Glu
1               5

<210> SEQ ID NO 101
<211> LENGTH: 9
<212> TYPE: PRT
<213> ORGANISM: Mus musculus
<220> FEATURE:
<221> NAME/KEY: PEPTIDE
<222> LOCATION: (1)..(9)
```

```
<400> SEQUENCE: 101

Val Lys Val Ser Cys Lys Ala Ser Gly
1               5

<210> SEQ ID NO 102
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 102

Tyr Thr Phe Ser Ser Phe Trp Met His
1               5

<210> SEQ ID NO 103
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 103

Phe Ser Ser Phe Trp Met His Trp Val
1               5

<210> SEQ ID NO 104
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 104

Phe Trp Met His Trp Val Arg Gln Ala
1               5

<210> SEQ ID NO 105
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 105

Trp Met His Trp Val Arg Gln Ala Pro
1               5

<210> SEQ ID NO 106
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 106

Trp Val Arg Gln Ala Pro Gly Gln Gly
1               5

<210> SEQ ID NO 107
<211> LENGTH: 9
<212> TYPE: PRT
```

```
<213> ORGANISM: Mus musculus
<220> FEATURE:
<221> NAME/KEY: PEPTIDE
<222> LOCATION: (1)..(9)

<400> SEQUENCE: 107

Val Arg Gln Ala Pro Gly Gln Gly Leu
1               5

<210> SEQ ID NO 108
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 108

Trp Ile Gly Tyr Ile Asn Pro Arg Ser
1               5

<210> SEQ ID NO 109
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 109

Ile Gly Tyr Ile Asn Pro Arg Ser Gly
1               5

<210> SEQ ID NO 110
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 110

Ile Asn Pro Arg Ser Gly Tyr Thr Glu
1               5

<210> SEQ ID NO 111
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 111

Ile Phe Arg Asp Lys Ala Thr Met Thr
1               5

<210> SEQ ID NO 112
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 112

Phe Arg Asp Lys Ala Thr Met Thr Thr
1               5
```

<210> SEQ ID NO 113
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 113

Tyr Met Glu Leu Ser Ser Leu Arg Ser
1               5

<210> SEQ ID NO 114
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 114

Met Glu Leu Ser Ser Leu Arg Ser Glu
1               5

<210> SEQ ID NO 115
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 115

Leu Arg Ser Glu Asp Thr Ala Val Tyr
1               5

<210> SEQ ID NO 116
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 116

Val Tyr Tyr Cys Ala Ser Phe Leu Gly
1               5

<210> SEQ ID NO 117
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 117

Tyr Tyr Cys Ala Ser Phe Leu Gly Arg
1               5

<210> SEQ ID NO 118
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 118

```
Phe Leu Gly Arg Gly Ala Met Asp Tyr
1               5

<210> SEQ ID NO 119
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 119

Tyr Trp Gly Gln Gly Thr Ser Val Thr
1               5

<210> SEQ ID NO 120
<211> LENGTH: 9
<212> TYPE: PRT
<213> ORGANISM: Mus musculus
<220> FEATURE:
<221> NAME/KEY: PEPTIDE
<222> LOCATION: (1)..(9)

<400> SEQUENCE: 120

Trp Gly Gln Gly Thr Ser Val Thr Val
1               5
```

ENGINEERED ANTI-ALPHA V-INTEGRIN HYBRID ANTIBODIES

FIELD OF THE INVENTION

The invention relates to engineered antibodies which specifically bind to integrin receptors, especially the alpha V integrin receptor subunit. The antibodies comprise the antigen binding sites (CDRs) of a known mouse anti-integrin antibody, as well as hybrid light chain variable sequences, mutated heavy chain variable sequences (Frs) and modified heavy chain constant sequences. The novel antibodies have improved immunogenic and expression properties and elicit excellent anti-angiogenic as well as anti-tumor activities in humans in monotherapy but also and above all in combination with other angiogenesis and tumor inhibiting agents, such as cilengitide, cetuximab and chemotherapeutic agents.

BACKGROUND OF THE INVENTION

Treatment of cancer remains a major problem in health care. One proposed strategy for treatment of cancer is inhibition of angiogenesis and thus inhibiting the generation and development of blood vessels, which supply the tumor with growth relevant means. A second strategy is direct inhibition of specific receptors on tumor cell surfaces, such as the inhibition of Her2 by Herceptin® or inhibition of EGFR by cetuximab (Erbitux®).

Inhibitors of integrins are considered to be potentially useful anti-tumor agents, because integrins are expressed on tumor neovasculature and mediate angiogenesis. In addition, integrins are expressed on certain tumor cells and may directly promote tumor growth and survival.

Integrins have no enzymatic activity, but integrins capable of binding their ligands (ligand-competent integrins) are activated by binding to proteins of the ECM. Integrins on one hand trigger intracellular kinase cascades to modulate cell growth and survival, and on the other associate with the cytoskeleton to drive cell attachment and locomotion. αvβ5 integrin specifically binds vitronectin, while αvβ3 also binds other macromolecules of the provisional ECM. αvβ3 was first noted in cancer as a progression-dependent marker on malignant melanoma. It enhanced melanoma growth in vivo and survival in vitro. αvβ3 blockers reversed these effects. Subsequently, αvβ3 was found in other tumors including glioblastoma, renal carcinomas, ovarian carcinomas and others. αvβ3 was also widely over-expressed in the ECs in many malignancies. In vitro, angiogenic models activated by tumor-derived growth factors over-expressed and required αvβ3 on the sprouting vasculature, while αvβ3 and αvβ5 blockade could suppress the angiogenic phenotype. αvβ5 was also shown to support the neo-vasculature induced by some tumor-derived growth factors. Inhibiting αvβ5 can trigger apoptosis of tumor cells.

The integrin receptors are over-expressed on tumor invasive blood vessels, on melanomas and some other malignancies, and modulate cellular response to growth factors. The vascular compartment is a promising therapeutic target because solid tumors depends on blood vessels for oxygen, nutrition, detoxification and the dispersion of blood borne metastases; the switch to the angiogenic phenotype marks a discrete step in the induction of malignancy, which is amenable to therapeutic intervention; and the vasculature undergoes continuous change, yet endothelial cells have genomic stability relative to the tumor, and are less likely to become drug-resistant through mutation.

A first anti-integrin drug is cilengitide and is considered to be a useful antitumor agent (Eskens F A, et al. (2003) Eur J Cancer 39:917-26). However, cilengitide is a small molecule that must be dosed frequently. The structure of cilengitide; selected salt form e.g. are disclosed in EP0770622, WO 0015244 and PCT/us07/01446 and are disclosed herein by reference.

A second anti-integrin drug is mouse mAb 17E6 (EMD 73034), that inhibits specifically the αv integrin subunit of human integrin receptor bearing cells. The mouse IgG1 antibody is described, for example by Mitjans et al. (1995; J. Cell Sci. 108, 2825) and U.S. Pat. No. 5,985,278 and EP 719 859. The complete variable heavy and light chain sequences are depicted in SEQ ID Nos. 27 and 28 (FIGS. 20 A, B). Murine 17E6 was generated from mice immunized with purified and Sepharose-immobilized human αvβ3. Spleen lymphocytes from immunized mice were fused with murine myeloma cells and one of the resulting hybridoma clones produced monoclonal antibody 17E6 (EMD 73034). Mouse mAb 17E6 is produced by hybridoma cell line 272-17E6 and deposited under accession number DSM ACC2160.

Mouse 17E6 antagonizes integrin interaction with the extracellular matrix (ECM), and perturbs the function of endothelial and tumor cells. Primary effects of the antibody include disrupting endothelial cell (EC) adhesion and movement, inducing their apoptosis, and suppressing the activation of growth factor pathways. Blockade by said antibody directly suppresses survival of both the activated endothelial cells and some tumor cells.

Monoclonal antibodies such as 17E6 are generally useful for the inhibition of extracellular protein-protein interactions, such as the inhibition of ligand-receptor interactions. However, monoclonal antibodies are often difficult to express and often provoke an immune response, such as an anti-idiotypic response, which limits their effectiveness.

These data and principal knowledge gathered so far supported the need of development of a modified mouse 17E6 antibody with improved properties that binds specifically to integrins, can be efficiently expressed, and is relatively non-immunogenic in humans as a therapeutic agent in cancer. Such an engineered antibody should have the potential to suppress the development of the tumor both indirectly, via the tumor vasculature, and directly on the tumor cells themselves.

SUMMARY OF THE INVENTION

The invention relates to new antibodies having the biological characteristics of monoclonal mouse antibody 17E6 (EMD 73034) but with improved properties above all with respect to immunogenicity in humans and satisfying expression in mammalian expression systems in an industrial production and manufacturing scale.

The invention provides a few engineered antibodies having modified sequences, which recognize the same receptor epitope as mouse antibody 17E6 but show reduced immunogenicity in humans and can be better expressed as the comparable non-modified antibody.

It should be noted that modifying or engineering a mouse derived antibody in order to obtain reduced immunogenicity in humans is, as a rule, accompanied by a distinct loss of expression and/or binding affinity. Thus, chimerization or humanization according to well known standard techniques usually leads to a decrease of expression, binding affinity etc., which can only partially resolved by specific back mutations or other measures. Modifications within a respective protein molecule that are simultaneously successful with respect to reduced immunogenicity, high expression and satisfying binding affinity cannot be predicted. Thus, decreasing the number of T-cell epitopes in order to eliminate or reduce an immune response against the drug in a human as primary problem to be solved, may lead to non-tolerable loss of expression or binding affinity or both that would lead to further problems to be solved.

It is therefore object of the current invention to provide engineered antibodies with a defined target specificity that elicit reduced immunogenicity, satisfying expression and good binding affinity. These properties can be obtained by surprising modifications within the original source molecule mouse mAb 17E6. In many of the experiments it makes sense to compare the results not directly with the mouse 17E6 antibody but with a chimeric 17E6 version (containing human constant regions). Successful chimeric antibodies of the art, as a rule, show sufficient binding affinity and sufficient expression, but elicit often an immunogenic response in a human individual.

In principal, the invention provides engineered recombinant anti-αv-integrin hybrid antibodies with reduced or eliminated immunogenicity in humans comprising (i) a CDR light and a heavy chain region deriving from mouse monoclonal anti-αv integrin antibody 17E6

(ii) a light chain framework region which is taken from humanized monoclonal anti-EGFR antibody 425, (iii) a heavy chain framework region deriving from mouse monoclonal anti-αv integrin antibody 17E6, and (iv) a heavy chain constant region deriving from human IgG and a human constant light chain region.

Humanized monoclonal antibody 425 (matuzumab) is known, for example from EP 531 472, and derives from its murine counterpart 425 (mouse MAb 425, ATCC HB9629). The antibody was raised against the human A431 carcinoma cell line and found to bind to a polypeptide epitope on the external domain of the human epidermal growth factor receptor (EGFR). It was found to inhibit the binding of epidermal growth factor (EGF) at both low and high affinity EGFR sites. Matuzumab has shown in clinical trials high efficacy. The FR sequences of the light chain of matuzumab are depicted in SEQ ID Nos. 14-17 as specified below and in the claims.

Combining modified heavy chain framework (FRs) regions from anti-integrin mouse antibody 17E6 with light chain frame work regions of a differently specific humanized anti-EGFR antibody h425 (matuzumab) has generated—apart from other modification—some antibodies with superior immunogenic properties, which are furthermore sufficiently expressed in standard mammalian expression systems. Using the VL region (FRs) from mAb h425 surprisingly the expression level is distinctly increased, but, as shown later, further mutations had to be done in order to improve other properties, above all, binding affinity.

A further important modification is the replacement of an amino acid residue within the CDR2 region of the heavy chain of mouse 17E6. By replacing a cysteine residue by a tyrosine residue surprisingly protein stability and expression level can be distinctly improved at least compared to a chimeric 17E6 version.

Further improvements in expression and stability can be obtained by replacing the original mouse IgG1 heavy chain constant region by a human IgG2 with a modified human IgG1 hinge region. In a preferred embodiment said IgG2 can be further modified by replacing an arginine residue at position 297 by an glutamine (N297Q). This modification eliminates an N-glycosylation site and thus abolishes or reduces ADCC and CDC activity of the antibodies to be engineered. Unfortunately, by this measure, the immunogenicity increases, apparently by generation a new T-cell epitope. Surprisingly, by replacing a phenylalanine by alanine at position 296, less immunogenicity can be restored.

In order to reduce the number of T-cell epitopes in the original heavy chain framework region of mouse mAb17E6 numerous mutations have been carried out. In detail, mutations at one, more or all of the following positions of the mouse antibody: A9, E13, M20, K38, R40, A72, S76, Q82, G85, T87, S91 and S113 are necessary to reduce immunogenicity.

One preferred engineered antibody according to the invention, which shows best values of improved properties is designated in the following as "DI-17E6" or synonymously "DI-17E6γ2h(N297Q)" or "EMD 525797" and has the following sequence:

(i) variable and constant light chain sequences (SEQ ID No. 5, FIG. 1 C):

DIQMTQSPSSLSASVGDRVTITCRASQDISNYLAWYQQKPGKAPKLLIYY

TSKIHSGVPSRFSGSGSGTDYTFTISSLQPEDIATYYCQQGNTFPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC and (ii) variable and constant heavy chain sequences (SEQ ID No. 6, FIG. 1 D):

QVQLQQSGGELAKPGASVKVSCKASGYTFSSFWMHWVRQAPGQGLEWIGY

INPRSGYTEYNEIFRDKATMTTDTSTSTAYMELSSLRSEDTAVYYCASFL

GRGAMDYWGQGTTVTVSSASTKGPSVFPLAPCSRSTSESTAALGCLVKDY

FPEPVTVSWNSGALTSGVHTFPAVLQSSGLYSLSSVVTVPSSNFGTQTYT

CNVDHKPSNTKVDKTVEPKSSDKTHTCPPCPAPPVAGPSVFLFPPKPKDT

LMISRTPEVTCVVVDVSHEDPEVQFNWYVDGVEVHNAKTKPREEQAQSTF

RVVSVLTVVHQDWLNGKEYKCKVSNKGLPAPIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK, wherein the underlined sequences represent the variable regions with the CDRs (in bold). The light chain constant region is human kappa. The heavy chain constant region is human IgG2 with the modified IgG1 hinge region

EPKSSDKTHTCPPCP. (SEQ ID No. 40)

The corresponding DNA sequences of DI-17E6 are shown in FIGS. 17-19.

The invention is also directed to engineered antibodies as described above and below which are fused directly or via a linker molecule to cytokines, such as IL-2, IL-12, TNFa, IFNa, IFNb, or growth factors. Antibody fusion cytokines may be also used in tumor therapy and/or angiogenesis related diseases because the cytokine portion may contribute to an increased cytotoxicity. Antibody fusion proteins, especially immunocytokines are well known in the art. A preferred fusion protein according to the invention is DI-17E6-IL2, or DI-17E6-(L)-IL2, wherein L is a linker peptide.

According to the present invention it was shown that the engineered antibodies as described can be used in pharmaceutical compositions for the treatment of angiogenesis related diseases and/or tumor related disease. Surprisingly, the antibodies according to the invention elicit a direct effect on tumor growth which seems to be independent on the indirect anti-tumor effect caused by blocking angiogenesis.

It is also object of the invention to provide pharmaceutical compositions and their use to comprising a second therapeutic agent, which is preferably a chemotherapeutic agent, such as cisplatin, doxorubicin, etc., an av-integrin inhibitor, such as RGD-peptides, for example, cilengitide, or tyrosine kinase inhibitors, especially anti-erbB1 or erbB2 antibodies. Preferred examples are here cetuximab (monoclonal antibody c225, Erbitux®), matuzumab (humanized monoclonal antibody 425), or Herceptin® (humanized antibody 4D5).

According to the invention the engineered antibodies in said pharmaceutical compositions as discloses herein can strengthen the effect of the second therapeutic agent, in many cases by synergistic interaction.

According to the invention the combination of the preferred engineered antibody DI-17E6 or similar variants with anti-EGFR antibodies, preferably cetuximab causes a surprising effect, namely the delay or prevention of re-growth of tumor tissue after stopping administration with the engineered antibody, preferably DI-17E6.

The pharmaceutical composition comprising a second therapeutic agent may be also used as a kit of parts comprising in a first package the engineered antibody, preferably DI-17E6, and in a second package a second therapeutic agent, for example, an angiogenesis inhibitor, a chemotherapeutic agent or a tyrosine kinase inhibitor, such as an anti-EGFR or anti-Her2 antibody. A preferred second therapeutic agent of said kit is the angiogenesis inhibitor cilengitide or the anti-EGFR antibody cetuximab or matuzumab or a chemotherapeutic agent.

In summary the invention is related to the following:

An engineered recombinant anti-αv-integrin hybrid antibody comprising
(i) a CDR light and a heavy chain region deriving from mouse monoclonal anti-αv integrin antibody 17E6
(ii) a light chain framework region which is taken from humanized monoclonal anti-EGFR antibody 425,
(iii) a heavy chain framework region deriving from mouse monoclonal anti-αv integrin antibody 17E6, and
(iv) a heavy chain constant region deriving from human IgG and a human constant light chain region.

An engineered antibody as described, wherein the CDR light chain regions, which derive from mouse monoclonal anti-αv integrin antibody 17E6 are:

```
CDR1:    RASQDISNYLA     (SEQ ID No. 7)
CDR2:    YTSKIHS;        (SEQ ID No. 8)
CDR3:    QQGNTFPYT,      (SEQ ID No. 9)
``` and the CDR heavy chain regions are:

```
                                          (SEQ ID No. 8)
CDR1:    SFWMH, (SEQ ID No. 11)
CDR2:    YINPRSGYTE (X) NEIFRD, wherein X = C or Y, (SEQ ID No. 10)
CDR3:    FLGRGAMDY.
```

An engineered antibody as described, wherein the CDR2 region of the heavy chain has the sequence

```
         YINPRSGYTEYNEIFRD.    (SEQ ID No. 9)
```

An engineered antibody as described, wherein the light chain framework region which derives from humanized monoclonal anti-EGFR antibody 425, comprises the sequence

```
FR-1:
DIQMTQSPSSLSASVGDRVTITC,            (SEQ ID No. 12)

FR-2:
WYQQKPGKAPKLLIY                     (SEQ ID No. 13)

FR-3:
GVPSRFSGSGSGTDYTFTISSLQPEDIATYYC    (SEQ ID No. 14)

FR-4:
FGQGTKVEIK.                         (SEQ ID No. 15)
```

An engineered antibody as described, wherein said heavy chain framework region (FR1-FR4) deriving from mouse antibody 17E6 is mutated at 1-15 amino acid residue positions to reduce or eliminate number of T-cell epitopes and, thus, immunogenicity in humans.

An engineered antibody as described, wherein said heavy chain framework region is mutated at one, more or all of the following positions of the mouse antibody: A9, E13, M20, K38, R40, A72, S76, Q82, G85, T87, S91 and S113.

An engineered antibody as described, wherein said amino acid residue positions mutated in the engineered antibody are: A9G, E13K, M20V, K38R, R40A, A72T, S76T, Q82E, G85S, T87R, S91T, S113T.

An engineered antibody as described, wherein said heavy chain framework region comprises the following mutations:

A9G, E13K, M20V, K38R, R40A, A72T, S76T, Q82E, G85S, T87R, S91T and S113T.

An engineered recombinant anti-αv-integrin hybrid antibody comprising
(i) the light chain CDR regions:

```
CDR1:    RASQDISNYLA;    (SEQ ID No. 7)
CDR2:    YTSKIHS;        (SEQ ID No. 8)
CDR3:    QQGNTFPYT,      (SEQ ID No. 9)
```

(ii) the heavy chain CDR regions:

```
CDR1:    SFWMH,              (SEQ ID No. 10)
CDR2:    YINPRSGYTEYNEIFRD,  (SEQ ID No. 11)
and
CDR3:    FLGRGAMDY;          (SEQ ID No. 12)
```

(iii) the light chain framework regions:

```
FR-1:
DIQMTQSPSSLSASVGDRVTITC,            (SEQ ID No. 14)

FR-2:
WYQQKPGKAPKLLIY                     (SEQ ID No. 15)

FR-3:
GVPSRFSGSGSGTDYTFTISSLQPEDIATYYC    (SEQ ID No. 16)

FR-4:
FGQGTKVEIK                          (SEQ ID No. 17)
```

(iv) the heavy chain framework regions

```
FR1:
QVQLQQSGAELAEPGASVKMSCKASGYTFS    (SEQ ID No. 18)

FR2:
WVKQRPGQGLEWIG                    (SEQ ID No. 19)

FR3:
KATMTADTSSSTAYMQLSGLTSEDSAVYYCAS  (SEQ ID No. 20)

FR4:
WGQGTSVTVSS,                      (SEQ ID No. 21)
``` wherein one, more or all of the bold and underlined positions are mutated in order to reduce or eliminate T-cell epitopes and thus immunogenicity in a human, and (v) a heavy chain constant region deriving from human IgG and a human constant light chain region.

An engineered antibody as described, wherein said heavy chain framework regions are:

```
FR1:
QVQLQQSGGELAKPGASVKVSCKASGYTFS    (SEQ ID No. 22)

FR2:
WVRQAPGQGLEWIG                    (SEQ ID No. 23)

FR3:
KATMTTDTSTSTAYMELSSLRSEDTAVYYCAS  (SEQ ID No. 24)

FR4:
WGQGTTVTVSS.                      (SEQ ID No. 25)
```

An engineered antibody as described, wherein the heavy chain constant region derives from IgG2, wherein in a preferred embodiment said IgG2 constant region comprises a modified IgG1 hinge region.

An engineered antibody as described, wherein said modified IgG1 hinge region comprises the sequence

```
    EPKSSDKTHTCPPCP.              (SEQ ID No. 24)
```

An engineered antibody as described, wherein said IgG2 constant region is modified by replacing amino acid N to Q at position 297 (N297Q).

An engineered antibody as described, wherein amino acid residue F at position 296 is replaced by A (F296A) in order to eliminate a T-cell epitope generated by the modification at position 297.

An engineered antibody as described, wherein and the light chain constant region is human kappa.

A recombinant anti-αv-integrin hybrid antibody designated as "DI-17E6" essentially consisting of (i) variable and constant light chain sequences (SEQ ID No. 3):

DIQMTQSPSSLSASVGDRVTITCRASQDISNYLAWYQQKPGKAPKLLIYY

TSKIHSGVPSRFSGSGSGTDYTFTISSLQPEDIATYYCQQGNTFPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
and (ii) variable and constant heavy chain sequences (SEQ ID No. 4):

QVQLQQSGGELAKPGASVKVSCKASGYTFSSFWMHWVRQAPGQGLEWIGY

INPRSGYTEYNEIFRDKATMTTDTSTSTAYMELSSLRSEDTAVYYCASFL

GRGAMDYWGQGTTVTVSSASTKGPSVFPLAPCSRSTSESTAALGCLVKDY

FPEPVTVSWNSGALTSGVHTFPAVLQSSGLYSLSSVVTVPSSNFGTQTYT

CNVDHKPSNTKVDKTVEPKSSDKTHTCPPCPAPPVAGPSVFLFPPKPKDT

LMISRTPEVTCVVVDVSHEDPEVQFNWYVDGVEVHNAKTKPREEQAQSTF

RVVSVLTVVHQDWLNGKEYKCKVSNKGLPAPIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK, wherein the underlined sequence tracks represent the variable regions in including the CDRs (in bold). The sequences in bold in the constant regions represent the modified hinge region (EPKSSDKTHTCPPCP) (SEQ ID No. 26) and the mutations at positions 296 and 297.

A fusion protein comprising an antibody as described, which fused preferably via its C-terminal to a cytokine or growth factor, preferably a cytokine.

A DNA molecule coding for an antibody or antibody fusion protein as described.

An expression vector comprising said DNA molecule.

An expression plasmid comprising the DNA segments as specified in Figure ???, and designated as pdHL10-DI-17E6g2h(N297Q).

A protein expression system comprising a mammalian host cell transformed with said expression plasmid.

A pharmaceutical composition comprising an antibody or antibody fusion protein as specified above and below in a pharmaceutically effective amount optionally together with a pharmaceutically acceptable carrier, diluent or excipient.

A pharmaceutical composition comprising a first and second pharmaceutically effective therapeutic agent, wherein the first agent is an antibody or antibody fusion protein as specified, and the second agent is selected from the group consisting of: a chemotherapeutic agent, an angiogenesis inhibitor and an anti-tumor agent optionally together with a pharmaceutically acceptable carrier, diluent or excipient.

A corresponding pharmaceutical composition, wherein the second therapeutic agent is an anti-tumor antibody, especially an anti-EGFR (erbB1) or an anti-Her2 (erbB2) antibody.

A corresponding pharmaceutical composition, wherein said second agent is integrin inhibitor cilengitide, anti-EGFR anti EGFR inhibitors mAb c225 (cetuximab, Erbitux®) and mAb h425 (matuzumab), and chemotherapeutic agents cisplatin or DTIC.

The use of an engineered antibody or antibody fusion protein as specified for the manufacture of a medicament for the treatment of an angiogenesis related disease and/or solid tumors or tumor metastases.

The use of a pharmaceutical composition as specified for the manufacture of a medicament for the treatment of tumors, wherein said engineered antibody increases the efficacy of the second agent.

The use of a pharmaceutical composition as specified for the manufacture of a medicament for the treatment of tumors, wherein the second agent is an anti-EGFR antibody, and said engineered antibody prevents or delays re-growth of tumor after stop administering the engineered antibody.

The use of claim 29, wherein the first therapeutic agent is the engineered antibody of claim 17 (DI-17E6) and the second therapeutic agent is mAb c225 (cetuximab).

DETAILED DESCRIPTION OF THE INVENTION

In order to reduce the potential for immunogenicity in man, DI-17E6 (EMD 525797) was made by de-immunization and genetic engineering of the murine 17E6 (EMD 73034).

De-immunization of an antibody according to the invention means detection and removal of human T-cell epitopes from the original mouse antibody. This technology is different from the "humanization" approach which replaces mouse sequences with human consensus to sequences. The De-immunization technology used, is described, for example, in WO 98/52976, WO 00/34317 and WO 02/69232.

The variable regions of the light (VL) and heavy (VH) chains of murine 17E6 are analyzed in silico to remove potential T-helper cell epitopes. De-immunized VH and VL sequences are designed to retain those amino acids from the murine sequence critical for binding, such as the CDRs.

To optimize expression, the framework regions of the light chain were replaced by those of a humanized 425 antibody. Furthermore, the unpaired cysteine-60 in the VH, which was rare among VH sequences, was converted to tyrosine (C60Y) to improve protein stability.

One of the features of EMD 525797 is not to trigger immune responses. To accomplish this, the constant regions of the immunoglobulin were also modified as follows. For the light chain, the genomic human kappa constant region was used. For the heavy chain, the genomic human gamma-2 (γ2) constant regions were used, but the hinge region with the four cysteine disulfide bonds was replaced by a modified γ1 hinge region to minimize disulphide bond scrambling and to improve expression. A mutation of Asn-297 in the CH2 domain to Gln (N297Q), was introduced to remove the N-glycosylation signal: the resultant de-glycosylation abrogates effector functions and prolongs serum half-life of the antibody.

Finally, Phe-296 was mutated to Ala, which removed potential T cell epitopes created by the N297Q mutation.

The preferred antibody DI-17E6 obtained by the method shortly described above (schematic structure is depicted in FIG. 16, has the following properties:

DI-17E6 shows potency and selectivity at the isolated receptor and cellular level (e.g. receptor binding, cell adhesion and cell migration studies).

DI-17E6 shows tumor-growth inhibiting activity in vitro and in animal models (e.g. experimental tumor nude mouse, SCID mouse/human skin chimera).

DI-17E6 shows anti-angiogenic activity in animal models (e.g. SCID mouse/human skin chimera, Matrigel plug in monkeys).

DI-17E6 selectively inhibits the binding of extracellular matrix (ECM) proteins to αv-integrin receptors and blocks av-integrin-mediated cell adhesion, attachment and migration. Once cell detachment is induced, two additional events happen: cellular activation pathways are blocked, and av-integrin is internalized in tissue culture. Fibrinogen binding to platelet receptor GPIIbIIIa and platelet aggregation are not affected and EMD trigger neither antibody dependent cell cytotoxicity (ADCC) nor complement dependent cytotoxicity (CDC).

DI-17E6 (EMD 525797) exhibits a narrow species specificity and only human and monkey αv-integrins are recognized. Growth of a human av-integrin deficient melanoma and a vascular growth response were inhibited by EMD 525797 in human skin grafted onto SCID mice. Systemic administration of EMD 525797 in healthy monkeys blocked angiogenesis provoked by subcutaneous implantation of plugs containing angiogenic growth factors like basic Fibroblast Growth Factor (bFGF). EMD 525797 has also demonstrated direct anti-tumor activity in xenograft models of αvβ3-integrin expressing human tumors, including some melanomas. In combination therapy studies EMD 525797 activity synergizes well with chemotherapeutic drugs allowing to use lower, less toxic concentrations of standard chemotherapeutics and still remaining effective in a clinic-like setting. These experiments were only able to demonstrate the potential anti-tumor activity of EMD 525797, because murine vascular endothelia do not express the target ocv integrin and are, therefore, not recognized by the antibody.

The data of a 4-weeks toxicology study did not reveal any treatment-related effects of DI-17E6 on clinical observations, body weight and food consumption, ECG, body temperature, respiratory rate, clinical pathology (hematology, serum chemistry), urinalysis, organ weight, macroscopic and histopathology.

Based on these data the doses of 10, 33 and 100 mg EMD 525797/kg body weight/day, administered once weekly for 4 weeks by intravenous infusion (1 h), were considered to be well tolerated and under the study conditions. The antibody is not orally active, but has been successfully administered by i.v., and i.p. routes in animal studies in which it has been shown to inhibit the angiogenesis and growth of several different experimental tumors.

A bacterial screening test investigating the mutagenic potential of EMD 525797 showed that EMD 525797 is not mutagenic. No safety pharmacology alerts of EMD 525797 were observed in repeat-dose-toxicity studies in cynomolgus monkey.

EMD 525797 has a theoretical molecular weight of 145, 208 Da, which has been verified experimentally via MALDI-TOF-MS and LC-ESI-Q-TOF MS analysis. The isoelectric point ranges from 7.35 to 8.15 with an average of 7.75. The extinction coefficient is 1.42.

EMD 525797 inhibits human endothelial cell adhesion to vitronectin with an EC50 of approximately 10 nM. EMD 525797 blocks tumor cell adhesions mediated by αv-integrins with an EC50 ranging from 0.1 to 50 nM. VEGF-induced migration of human endothelial cells on vitronectin is also blocked by EMD 525797 with an EC50 around 50 nM. Similarly, proliferation and survival of human endothelial cells plated on αv-integrin ligands is also blocked by EMD 525797.

EMD 525797 targets endothelial αv-integrins and disrupts vessel formation. It inhibits especially integrins αv3 and αv5 and blocks αv-integrin-mediated cell behavior, including attachment, and migration. Alpha-v integrin and growth factor signaling pathways interact, so EMD 525797 binding can also disrupt differentiation, proliferation, and survival. In addition to its anti-angiogenic effect, EMD 525797 evidently promotes apoptosis as a direct anti-tumor effect in target presenting malignant cells. EMD 525797 can block cell attachment, induce cell detachment, block migration, proliferation and survival on αv-integrin ligands.

DI-17E6 is the first deimmunized protein for which immunogenicity data in humans are available: In a respective clinical trial anti-DI-17E6 antibodies were not detected at doses over 500 mg, which is a'common therapeutically effective dose for antibodies. In comparison, anti-drug antibodies could be detected in animal trials at correspondingly calculated doses. In general, immune behavior of DI-17E6 is deemed to more complex: 17E6 binding to αv will promote uptake into dendritic cells. FcR binding by 17E6 seems to be knocked out. 17E6 binding to integrin receptor will probably inhibit a natural immunosuppressive mechanism. Thus the results obtained by the engineered antibodies, preferably, DI-17E6 are not expectable in any case and are surprising.

DI-17E6 has a binding affinity to the αvβ3 integrin receptor which is similar chimeric 17E6 comprising the same constant regions as DI-17E6. Surprisingly, a mutation of the antibody that comprises already the variable framework regions of humanized mAb 425 but still the original VH region of mouse 17E6 antibody does not bind to integrin receptor.

DI-17E6 is well expressed by NS0 cells and other mammalian cell lines. Interestingly the mutation which shows no binding affinity to integrin as described above, shows the same favourable expression rate. These and similar results show that prediction of the three desired properties: reduced immunogenicity, high expression levels and satisfying binding affinity is not possible.

In vitro and in vivo angiogenesis steps are perturbed by DI-17E6, as is melanoma tumor growth. DI-17E6 can enhance the activity of cytotoxic drug based therapies, leading to more anti-tumor activity in vivo.

DI-17E6 causes the depolymerization of focal adhesions dependent on αvβ3 and αv115. These signalling complexes assemble after integrin ligation. They organize communication with growth, survival and motility pathways, and their destruction can trigger apoptosis.

Thus DI-17E6 uses a combination of mechanochemical and biochemical effects to affect endothelia and to increase stress on tumor cells.

DI-17E6 exerts its biological activities in vivo via the effects on at least two different cell compartments within the tumor: to the tumor cells themselves, and to the angiogenically activated tumor endothelial cells. Tumor and endothelial cell attachment mediated by αvβ3 or αvβ5 is disrupted by DI-17E6. ECs in culture migrate over provisional ECM, and this migration is disrupted by DI-17E6. The morphogenetic changes involved in forming blood vessels are complex, but can be modeled in vitro in human endothelial cell migration assays where DI-17E6 can block this process. It also blocks angiogenesis when administered systemically in vivo in the human skin-SCID mice chimera model, and in the matrigel plug model in monkeys. This suggests that DI-17E6 affects angiogenic endothelia. Indirect evidence for anti-angiogenesis is presented below. Depending on whether VEGFA or FGF2 is the inducer, the angiogenesis triggered is dependent on αvβ5 or on αvβ3. Since DI-17E6 blocks both αv-integrins, it may block both pathways.

Although DI-17E6 is thought of as primarily targeting ECs, it can also inhibit growth and survival of tumor cells themselves. So far, this has only been demonstrated for tumors expressing αvβ3.

Tumor cell lines from different tumor indications (melanoma, ovarian, renal, colon, breast, and lung) have their growth affected when treated with DI-17E6 in vitro. The activity of DI-17E6 to induce anti-proliferation varies on the different cell lines and this may be due to both the genetic background of each cell line and the level of αv-integrin expression by these cell lines.

DI-17E6 can inhibit the growth of xenograft tumors in mice. It also shows synergistic effects in combination with chemotherapeutic reagents. These effects are dependent on tumor context, and other conditions (e.g. in vitro/in vivo) but efficacy has been observed in subcutaneous and orthotopic locations like pancreas (see Examples)).

In solid tumors ligand-competent αvβ3 is frequently overexpressed on the tumor-invasive vasculature and also on some human tumors, including melanomas, renal carcinomas, brain tumors. This expression is accompanied by the deposition of ligands of ocvβ3, like vitronectin, von Willebrand factor and fibrinogen, and by the anomalous synthesis of such proteins. For example, vitronectin, mainly produced in the liver, is expressed in some tumors. In healthy adults vitronectin and fibrinogen are in a blood-borne inactive form, but on activation (e.g. in tumor patients) they undergo conformational change and deposit into the subendothelial ECM. Thus, DI-17E6 targets are expressed both by tumor-invasive vessels and by some tumors, which also express vitronectin receptor.

Subcutaneous growth of αvβ3-expressing melanoma cells is suppressed by EMD 525797 at different doses. In a human skin-SCID mouse chimeric model, where human melanomas lacking alpha-v integrins were vascularized by human ECs, EMD 525797 also inhibits tumor growth, indicating its antiangiogenic effect.

Furthermore, in a tumor-free model in monkeys, where angiogenesis is induced by the angiogenic growth factor bFGF, DI-17E6 also blocked the growth factor induced angiogenesis. Based on the in vivo investigations and according to the experimental plasma trough concentrations identified in several PK/PD in vivo studies, EMD 525797 administrations in clinical trials includes dosing to reach plasma trough concentrations ranging from 10 to 500 μg/ml.

If applied to melanoma xenograft mice models (M21, MeWo or CAKI-1) DI-17E6 causes in lower doses (ca. 30 mg/Kg) a slight tumor regression effect, whereas the effect is considerably enhance if higher doses (500 ul/ml) are administered.

It should be noted that the basic biological and therapeutic properties as specified above for DI-17E6 are also applicable for other variants of DI-17E6 as specified in this application.

Combination Therapy

Endothelial cells proliferate and invade the tumor environment in response to soluble cytokines and to growth factors secreted by the tumor. Such endothelial cells are a suitable target for therapy, as has been recently validated in human cancer patients. The alpha-v integrins expressed de novo by such tumor invasive endothelium support their survival in the foreign environment of the transitional extracellular matrix, and the inhibition of these integrins can have an antiangiogenic effect.

Thus alpha v beta 3 or αv integrin target therapy present an ideal setting to combine the antibody of the current invention with chemotherapeutics, other integrin inhibitors or tumor receptor blocking agents in pharmaceutical compositions and kit-of-parts for use in combination therapy of cancer.

Surprisingly it was found, that the direct anti-tumor effect can be enhanced by combining an engineered antibody according to the invention, preferably DI-17E6, with additional anti-tumor agents, especially tyrosine kinase inhibitors, preferably anti-erbB1(EGFR) and anti-erbB2(Her2) antibodies. Anti-tumor therapy targets the tumor tissue itself by blocking tumor-specific receptors, and thus prevents tumor growth, or promotes tumor shrinking.

According to the invention it could be demonstrated that some chemotherapeutics cause in combination with an engineered antibody according to the invention, preferably DI-17E6, an additive effect only, whereas in other experiments using other chemotherapeutics (e.g. Dacarbazine, DTIC) synergy effects can be observed. Moreover, the results depend on the system used, e.g. whether an in vivo or an in vitro system was taken.

One important result from the combination experiments is that the combined use of preferably DI-17E6 and cilengitide, a cyclic RGD peptide and integrin inhibitor (cyclo-(Arg-Gly-Asp-DPhe-NMeVal) shows synergistic effects in tumor growth regression in vitro as well as in vivo.

Similar synergistic effects on reduction of tumor growth can be obtained if DI-17E6 is combined with cetuximab (Erbitux®). Erbitux (cetuximab) is a chimeric mouse/human monoclonal antibody (MAb) of IgG1 subclass that targets the human epidermal growth factor receptor (EGFR). Different renal cell carcinoma (RCC) cell lines express the EGFR. Erbitux is marketed product and approved for several tumor indications.

In all cases of synergy it can be concluded from the results that the engineered DI-17E6 antibody strengthens the anti-tumor effect of the second agent used in the combination.

According to the invention, DI-17E6 causes, when combined with cetuximab, a steady decrease in tumor size/growth can be observed for a longer period (ca. 40 days) even if administration of drugs is stopped. This is not the case if cetuximab is administered in mono therapy.

The engineered antibodies according to the invention may be administered to a patient in need thereof before, after or simultaneous with the second therapeutic agent.

The chemotherapeutic agent used in combination with any engineered antibody according to the invention may be e.g. methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, vairubicin, carmustaine, UFT (Tegafur/Uracil), ZD 9331, Taxotere/Decetaxel, Fluorouracil (5-FU), vinblastine, and other well compounds from this class.

The therapeutic compositions or DI17E6 compositions of the invention with or without a second therapeutic agent can also be used in combination with other anti-cancer strategies, and such combination therapies are effective in inhibiting and/or eliminating tumor growth and metastasis. The methods of the present invention can advantageously be used with other treatment modalities, including, without limitation, radiation therapy, surgery, gene therapy and chemotherapy.

Surprisingly it was found, that the anti-angiogenic effect can be enhanced by combining an antibody according to the invention with treatment with additional angiogenesis inhibitors. Antiangiogenic therapy targets the tumor vasculature and prevents tumor growth beyond a certain size, thus in second preferred embodiment the secondary medicament is an inhibitor of angiogenesis preferably selected from the following list:

The inhibitor of angiogenesis may be, but are not limited to, e.g. cilengitde (EMD 121974), anti-VEGF antibody LM609, BMS-275291, Dalteparin (Fragmin®), Suramin, 2-methoxyestradiol (2-ME), Thalidomide, CC-5013 (Thalidomide Analog), Combretastatin A4 Phosphate, LY317615 (Protein Kinase C Beta Inhibitor), AE-941 (Neovastat™; GW786034), Anti-VEGF Antibody (Bevacizumab; Avastin™), ZD6474, Carboxyamidotriazole (CAI), Celecoxib (Celebrex®).

The antibodies of the invention can be incorporated into a pharmaceutical composition suitable for administration. Such compositions typically comprise the antibody variable regions and a pharmaceutically-acceptable carrier. As used herein the language "pharmaceutically-acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Medicaments that contain the antibody variable regions of the invention can have a concentration of 0.01 to 100% (w/w), though the amount varies according to the dosage form of the medicaments.

Administration is preferably once per two weeks or once per month, but may be more or less frequent depending on the pharmacokinetic behavior of the 17E6/425-101 protein in a given individual. Dosing of DI-17E6 or other antibodies as specified in this application (e.g. cetuximab) for an adult of about 70 kilograms is in the range of about 50 to 1000 milligrams per dose, with a preferred range of about 100 to 500 milligrams per dose. The most preferred dose is about 400 milligrams for a 70 kg adult treated once per month.

Chemotherapeutic agents as mentioned herein are administered as a rule at doses between 10 mg/Kg and 100 mg/Kg.

In combination therapy with a second therapeutic agent as specified the engineered antibody according to the invention can be given simultaneously with the second agent at the starting point of the therapy or after or before the administration of the second agent.

SHORT DESCRIPTION OF THE FIGURES

FIG. 1A: variable light chain sequences of DI-17E6 (SEQ ID No. 1)

FIG. 1B: variable heavy chain sequences of DI-17E6 (SEQ ID No. 3)

FIG. 1C: complete light chain protein sequence of DI-17E6 (SEQ ID No. 5):
Variable regions are underlined, with CDRs in bold.

FIG. 1D: complete heavy chain protein sequence of DI-17E6 (SEQ ID No. 6):
Variable regions are underlined, with CDRs in bold. Bold sequences in constant regions indicate modified IgG1 hinge region and modifications at positions 296 and 297.

FIG. 2: anti-agiogeneic activity of DI-17E6 in a monkey Matrigel plug experiment: anti-antibody detection in monkey sera dependent on drug concentration on different days (single dose).

Figure 3:
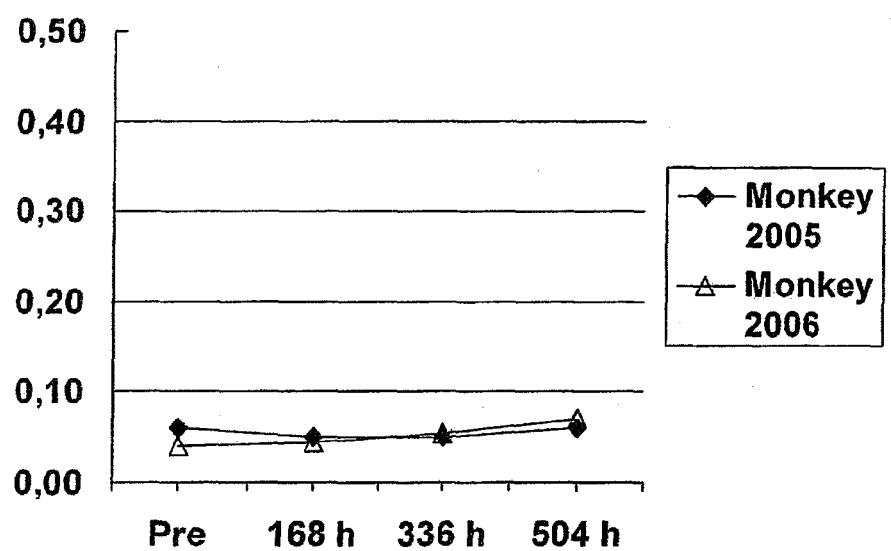

FIG. 3: anti-agiogeneic activity of DI-17E6 (EMD 525797) in a monkey Matrigel plug experiment: anti-antibody detection in monkey sera for dosing of DI-17E6 (30 mg/Kg) dependent on time (long term).

Figure 4:
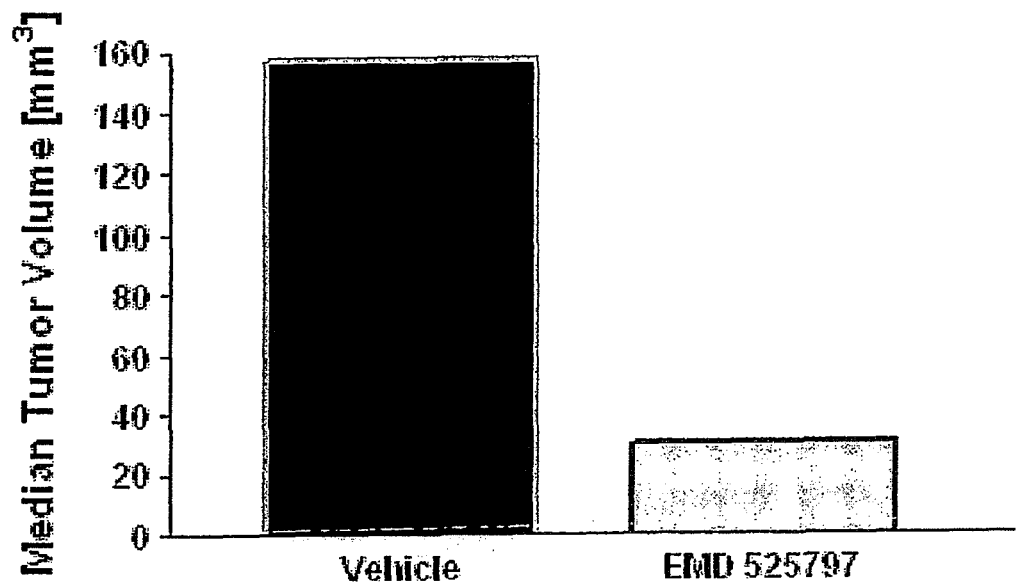

FIG. 4: Effects of DI-17E6 on tumor growth in the SCID mouse-human skin chimera model with intradermal M21-L melanoma (administered 3 times per week at 1 mg/dose i.p. for 4 weeks, starting treatment one day after tumor cell inoculation.

Figure 5:
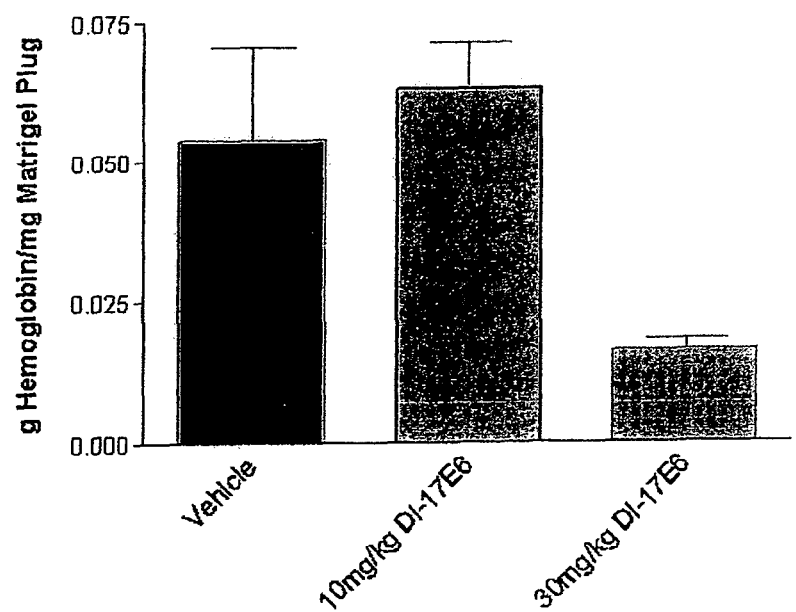

FIG. 5: Effects of DI-17E6 on growth factor induced angiogenesis in the Matrigel plug model in monkeys Growth factor induced angiogenesis inhibition by EMD 525797 in monkeys receiving one single therapeutic i.v. administration (10 or 30 mg/Kg). Treatment was at the same day of Matrigel implantation. One animal containing up to 6 Matrigel plugs was used per group. Analysis of hemoglobin content (g of hemoglobin/mg Matrigel plug) was performed after 6 days; given are means±SE.

Figure 6:
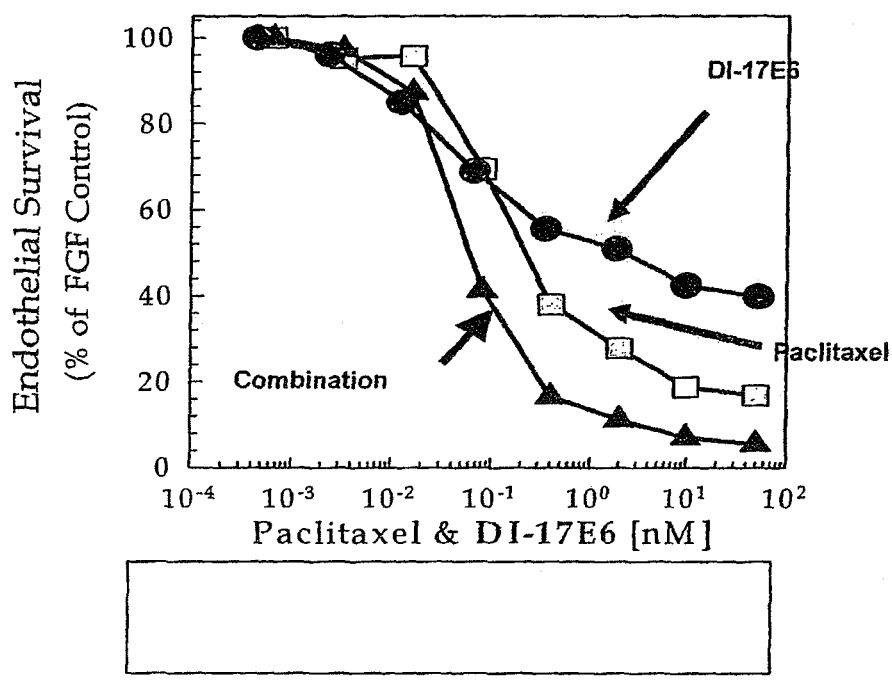

FIG. 6: Anti-proliferative effect of DI-17E6 combined with Paclitaxel in vitro shown in HUVE cells.

Figure 7:
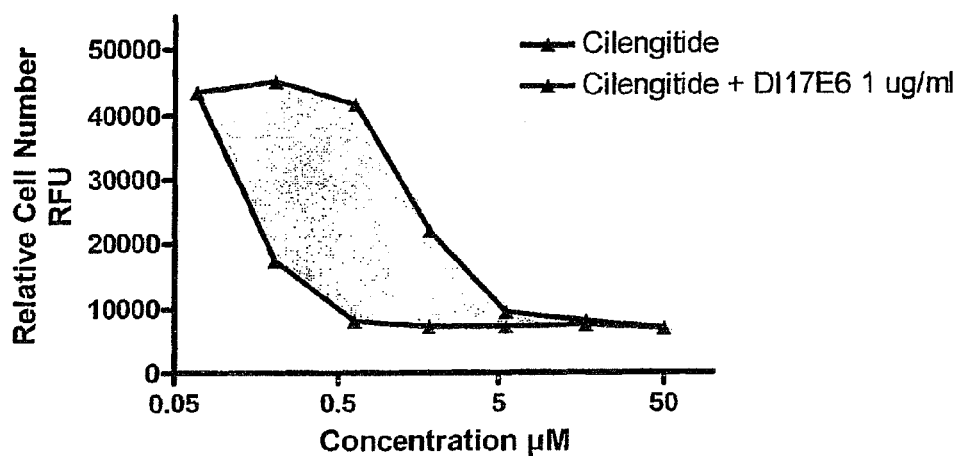

FIG. 7: Anti-proliferative synergistic effect of DI-17E6 combined with cilengitide in vitro shown in M21 human melanoma cell line. Upper curve: cilengitide alone, lower curve: DI-17E6+cilengitide.

Figure 8:
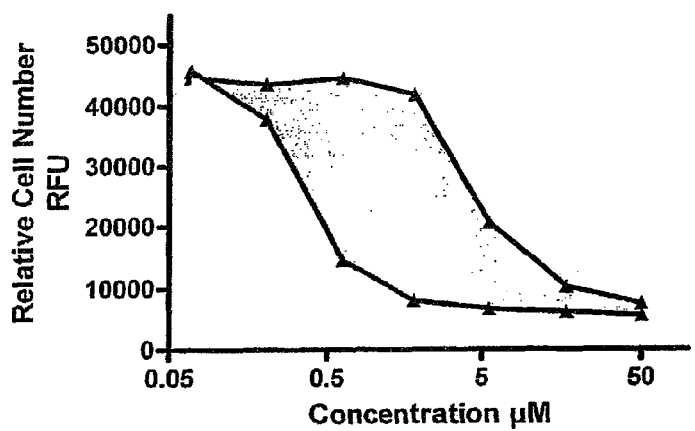

FIG. 8: Anti-proliferative synergistic effect of DI-17E6 combined with cilengitide in vitro shown in CAKI-2 human renal cell line. Upper curve: cilengitide alone, lower curve: DI-17E6+cilengitide.

Figure 9:
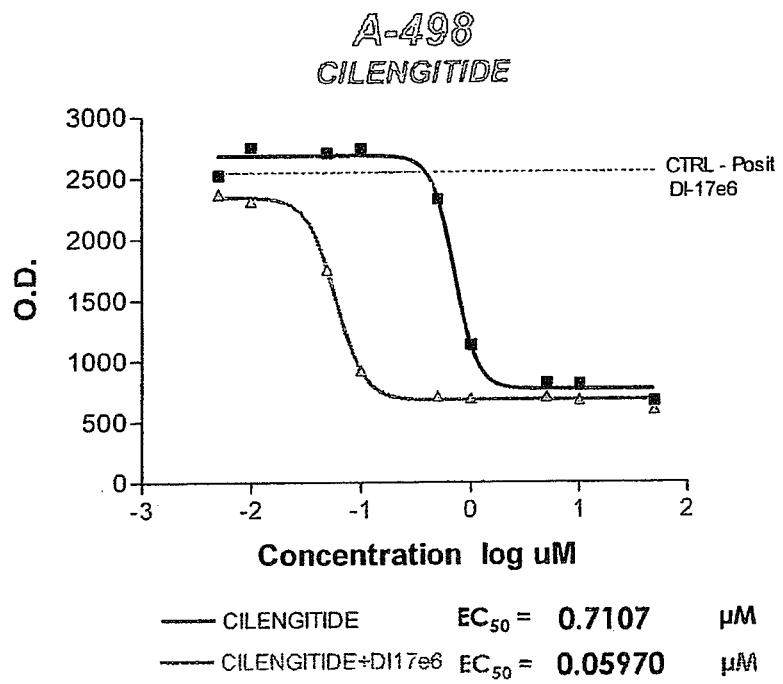

FIG. 9: Anti-proliferative synergistic effect of DI-17E6 combined with cilengitide in vitro shown in A498 human cell line. Curve with triangles DI-17E6+cilengitide, curve with squares: cilengitide alone.

Figure 10:
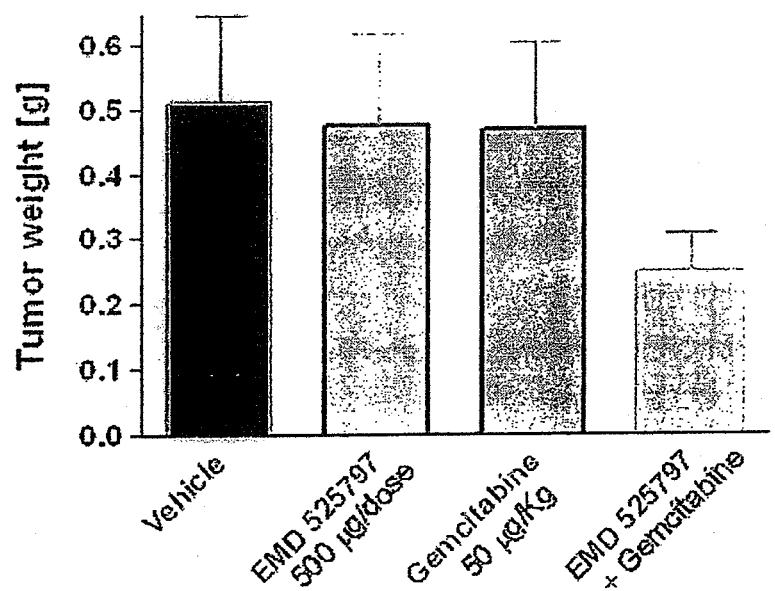

FIG. 10: In vivo—effect of DI-17E6 (EMD 525797) on chemotherapeutic treatment in an orthotopic pancreatic cancer xenograft tumor model: Inhibition of NP18-b3 pancreatic tumor (10 mg tumor fragments orthotopically stitched into the pancreas of nude mice) by combination of suboptimal doses of EMD525797 and gemcitabine at different doses. Treatment started 6 days after tumor fragment surgery. EMD 525797 was administered three times per week i.p. at 500 µg/dose. Gemcitabine was administered three times per week i.p. at 50 µg/Kg. Tumor weight is depicted after 42 days.

Figure 11:
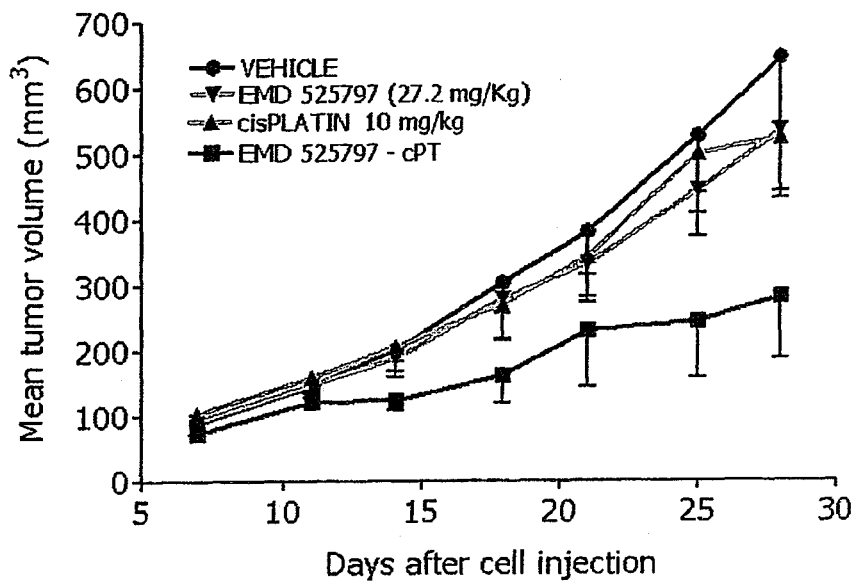

FIG. 11: In vivo—effect of DI-17E6 (EMD 525797) in combined treatment with cisplatin (cPT) xenografts tumor models using human M21 tumor cells transplanted into mice using suboptimal doses of DI-17E6. Treatment for EMD 525797 started at the same day than tumor cell injection. Treatment of cPT started at day 11 after tumor cell injection. EMD 525797 was administered once per week i.p. at 500 µg/dose. cPT was administered once per week i.p. at 10 mg/Kg.

Figure 12:
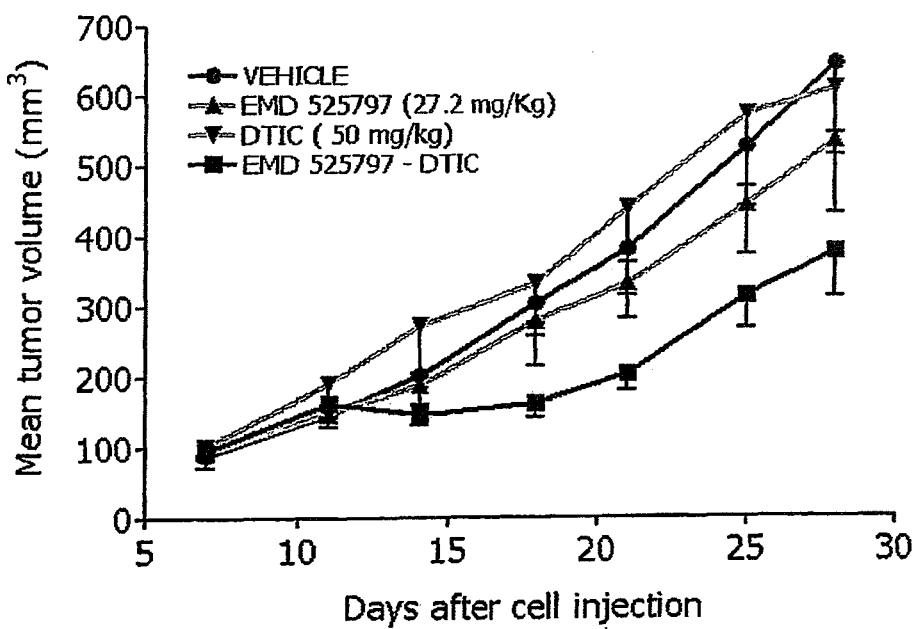

FIG. 12: In vivo—effect of DI-17E6 (EMD 525797) in combined treatment with darcabazine (DTIC) xenografts tumor models using human MeWo tumor cells transplanted into mice using suboptimal doses of DI-17E6. Treatment for EMD 525797 started at the same day than tumor cell injection. Treatment of DTIC started at day 11 after tumor cell injection. EMD 525797 was administered once per week i.p. at 500 µg/dose. DTIC was administered once per week i.p. at 50 mg/Kg.

Figure 13:
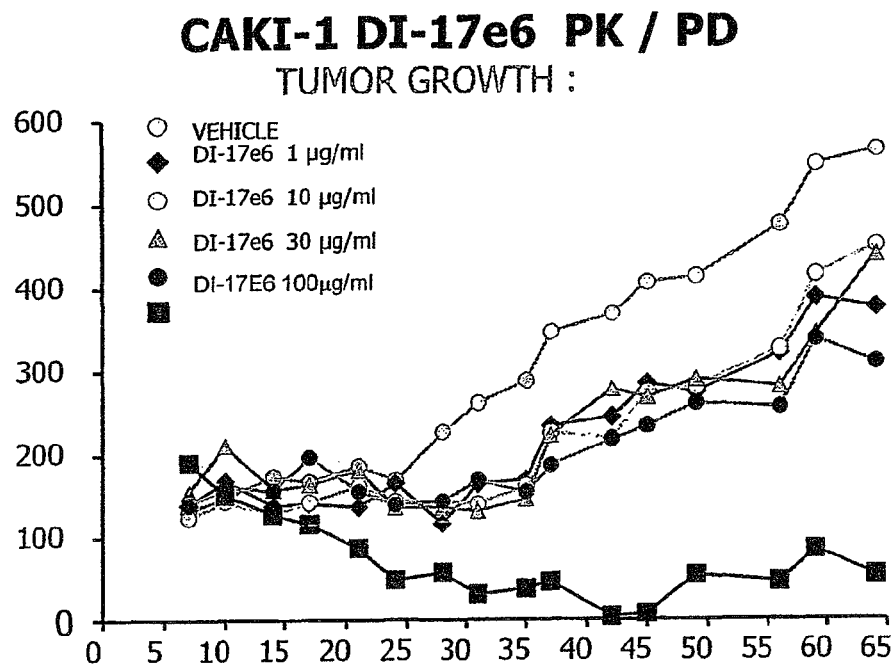

FIG. 13: In vivo—effect of DI-17E6 (EMD 525797) alone in xenografts tumor models using human CAKI-1 renal carcinoma tumor cells transplanted into mice using different doses (ug/ml serum) DI-17E6. y-axis: tumor volume (mm3), x-axis: days FIG. 14: In vivo—effect of DI-17E6 (EMD 525797) in combined treatment with cetuximab (Erbitux) in CAKI-1 renal carcinoma tumor cells transplanted into mice using DI-17E6 at a constant serum concentration of 100 ug/ml and Erbitux at a dose of 4 mg/Kg and 12 mg/Kg body weight. The dose regimen is depicted in Example 13. y-axis: tumor volume (mm3), x-axis: days.

Figure 15:
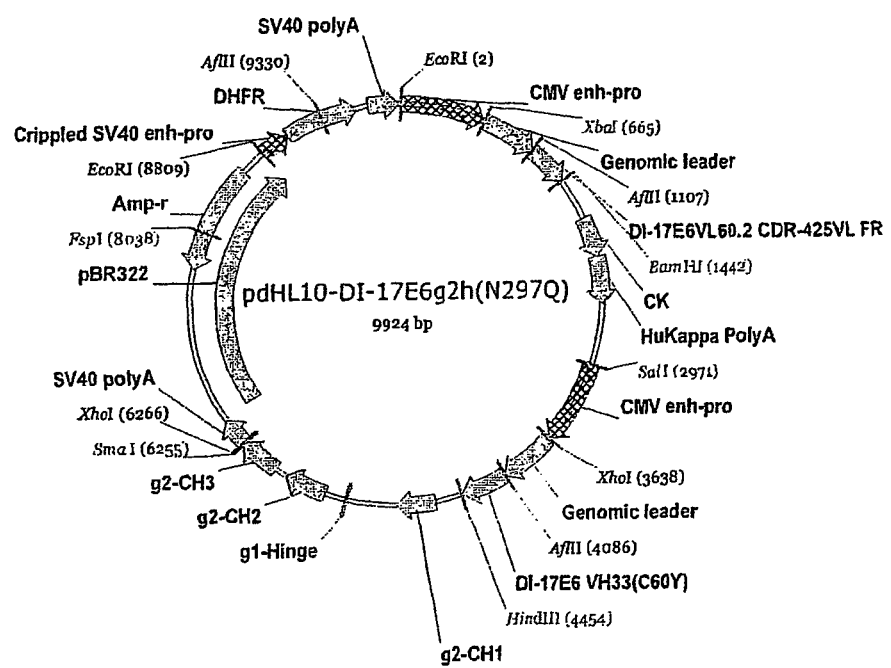

FIG. 15: Plasmid map of DI-17E6 expression plasmid pdHL10-DI-17E6γ2h(N297Q).

Figure 16:
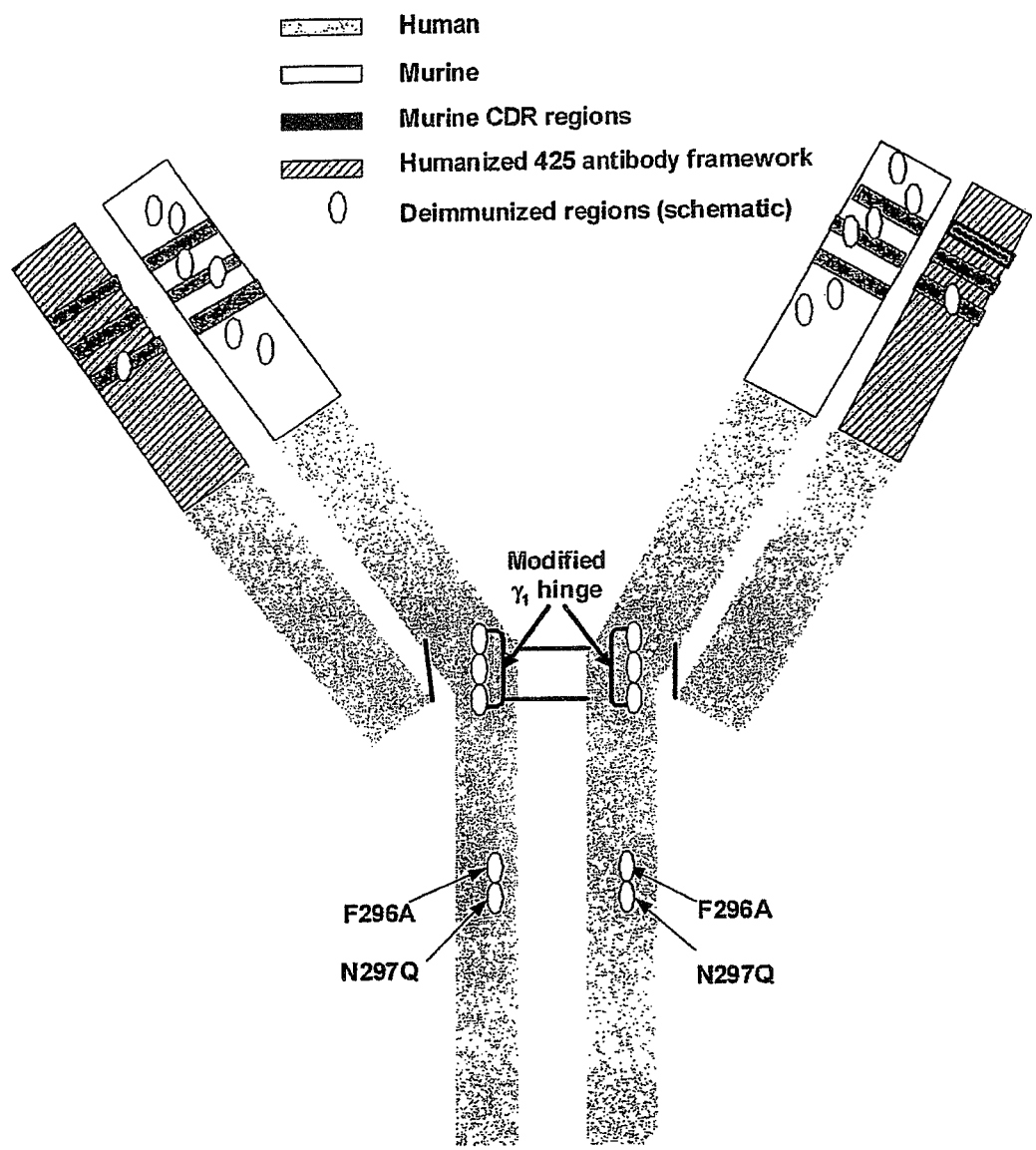

FIG. 16: Schematic structure of mAb DI-17E6 (EMD 525797).

FIG. 17 A: Complete DNA sequence of DI-17E6 from the translation initiation codon to the translation stop codon of the complete light chain (human kappa) as used in the expression plasmid pdHL10-DI-17E6 (coding sequence in upper case and non-coding sequence in lower case, variable and constant sequence in grey colored, variable sequence in italics) (SEQ ID No. 29)

FIG. 17 B: DNA sequence of variable light chain of DI-17E6 (SEQ ID No. 30)

FIG. 17 C: DNA sequence of constant light chain of DI-17E6 (SEQ ID No. 32)

FIG. 18 A: Complete DNA sequence of DI-17E6 from the translation initiation codon to the translation stop codon of the complete heavy chain as used in the expression plasmid pdHL10-DI-17E6 (coding sequence in upper case and non-coding sequence in lower case, variable and constant sequence in grey colored, variable sequence in italics; modified IgG1 hinge in bold) (SEQ ID No. 34).

FIG. 18 B: DNA sequence of variable heavy chain of DI-17E6 (SEQ ID No. 35)

FIG. 18 C: DNA sequence of constant heavy chain of DI-17E6 (SEQ ID No. 37)

FIG. 18 D: DNA sequence of modified IgG1 hinge of the heavy chain of DI-17E6 (SEQ ID No. 39)

FIG. 19 A: Complete heavy chain DNA sequence of DI-17E6 (SEQ ID No. 42)

FIG. 19 B: Complete light chain DNA sequence of DI-17E6 (SEQ ID No. 44)

FIG. 20A: Protein sequence of variable light chain of mouse antibody 17E6. Bold sequences represent the CDRs. (SEQ ID No. 27).

FIG. 20B: Protein sequence of variable heavy chain of mouse antibody 17E6. Bold sequences represent the CDRs. (SEQ ID No. 28).

Figure 21A:
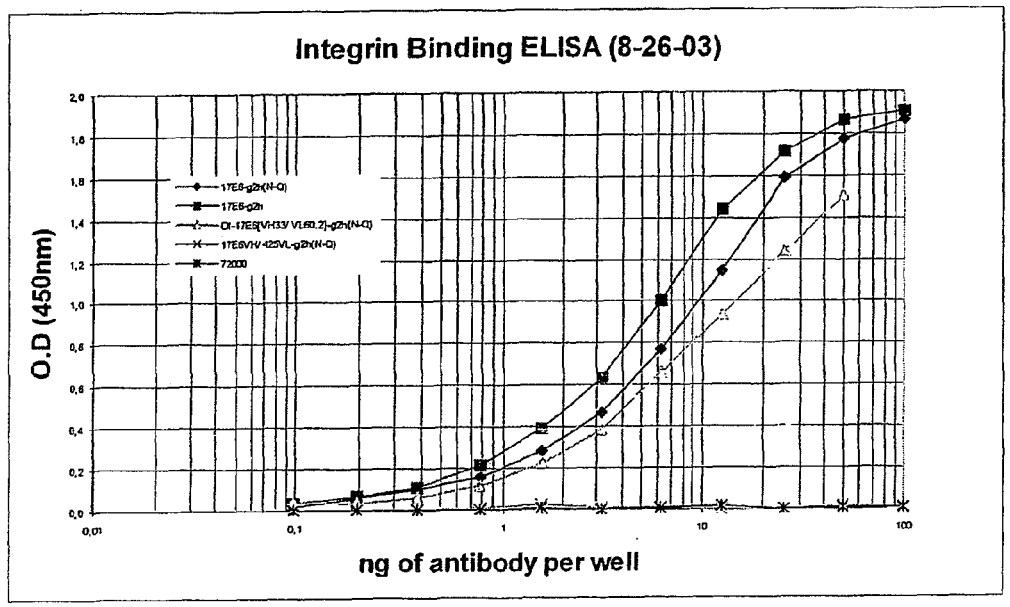

FIG. 21A: Integrin Binding ELISA of different versions of engineered antibodies.
cross (x)=17E6 VH/425VL-g2h(N-Q)
double cross (✳)=mAb 425
triangle=DI 17E6 VH33/VL60.2-g2h(N-Q)
diamond=17E6-g2h(N-Q)

Figure 21B:
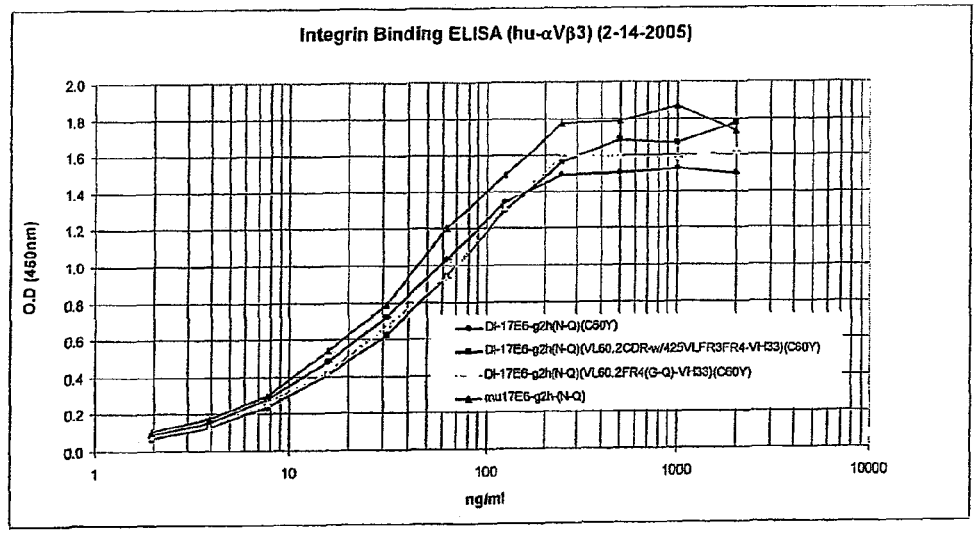

FIG. 21B: Integrin Binding ELISA of different versions of engineered antibodies.
filled triangle: murine 17E6-g2h(N-Q)
triangle: DI-17E6VL60.2CDR-425VLFR4/VH33(C60Y)-g2h(FN→AQ)
filled square: DI-17E6VL60.2CDR-425VLFR3FR4/VH33(C60Y)-g2h(FN→AQ)
filled circle: DI-17E6-g2h (N-Q)(C60Y)

The following examples describe the invention in further details. However, although using specific parameters, molecules, method steps etc. the invention is not limited thereon, if a skilled person can easily conclude from these data that the invention can be carried out with analogous means and methods.

Example 1

Construction and Expression of the Engineered Antibodies According to the Invention In order to reduce immunogenicity in man, DI-17E6 (EMD 525797) was made by de-immunization and genetic engineering of murine 17E6.

Source antibody was monoclonal mouse antibody 17E6 as described earlier. This antibody was generated from mice immunized with purified human αvβ3. Spleen lymphocytes from immunized mice were fused with murine myeloma cells and one of the resulting hybridoma clones produced monoclonal antibody 17E6 (see for example EP0719859). The hybridmoa cell line producing said andibody was deposited under DSM ACC2160.

In principal the variable regions of the light (VL) and heavy (VH) chains of murine 17E6 were analyzed in silico with the so-called de-immunization methodology (WO 98/52976, WO 00/34317 and WO 02/069232) to remove potential T-cell epitopes. De-immunized VH and VL sequences were designed to retain those amino acids from the murine sequence critical for binding, such as the CDRs.

Using this technology alone led to an antibody, which shows reduced or eliminated immunogenicity in a human individual, but did no show sufficient binding affinity and satisfying expression rates an a mammalian expression system. Thus, the antibody has be redesigned by modifying the amino acid sequence at several positions to reinstall binding affinity and expression. However, it became obvious that while improving expression pattern binding affinity decreased and vice versa. Thus, a lot of antibody versions had to be constructed, which were investigated for expression and binding affinity. The new version often show surprising results, which were not expected when molecule design was planned. Combining sequences from antibody version showing good expression with sequences of antibody versions showing good binding affinity often results in new antibody versions having bad binding affinity and expression. Therefore, as already pointed out, a prediction which specific antibody mutations elicit good expression and binding affinity was not possible.

Variable Regions of De-Immunized 17E6 (DI-17E6):

The variable regions of the light (VL) and heavy (VH) chains of the mouse monoclonal antibody 17E6 (SEQ. ID Nos. 25 and 26) were de-immunized in silico by the de-immunization technology as specified above, which removed potential T helper cell epitopes. This resulted in a de-immunized version of the VL called VL60.2 and a de-immunized version of the VH called VH33.

De-immunized 17E6 antibody consisting of the VL60.2 and VH33 produced by transfection of mammalian cells retained binding affinity to the αvβ3 integrin but was expressed poorly.

To optimize expression, the framework regions of the light chain were replaced by those of a humanized 425 antibody (Kettleborough et al., Protein Engineering 4:773, 1991). Furthermore, the unpaired cysteine-60 in the VH33, which was rare among VH sequences, was converted to tyrosine (C60Y) to provide protein stability.

The DNA encoding the final de-immunized VL (DI-17E6 VL, FIG. 1A) and VH (DI-17E6VH, FIG. 1A) were chemically synthesized, using codons optimized for mammalian expression.

Origin and Source of the NS0-LD Cell Line:

The mouse myeloma NS0 was obtained from the European Collection of Cell Cultures (ECACC #85110503). The NS0-LD cell line was obtained by selecting NS0 cells for growth in a lipid-free and serum-free medium, which consists of SM1F6 medium (Invitrogen) supplemented with 1 mM sodium pyruvate (Invitrogen), 1 g/L glucose (Merck KGaA), 1% non-essential amino acids (Invitrogen), 0.1 µM Tropolone (Sigma), 10 µM ethanolamine (Sigma), and 2 mM glutamine (Invitrogen). Frozen stocks of NS0-LD were prepared in a freezing medium consisting of 10% (v/v) filtered DMSO (Merck KGaA), 10% (v/v) of a 1% methylcellulose suspension in water (Sigma), 40% of fresh growth medium and 40% of conditioned medium of the NS0-LD cells.

Construction of The Expression Vector for DI-17E6v2h (N297Q)

A genomic signal peptide sequence (438-bp) from a mouse immunoglobulin light chain gene was used for the secretion of both the heavy and light chains. The gene sequence encoding the −2 amino acid residue (the −1 amino acid being the C-terminal residue of the signal peptide) of the signal peptide was mutagenized from a serine residue to a leucine residue (AGC to TTA) so that the DNA encoding the end of the signal peptide is CTTAAGC, where CTTAAG is a created AflII site (Lo et al., Protein Engineering 11:495, 1998). In addition, the Kozak consensus sequence CCACCATGG was introduced for optimal ribosome binding for translation initiation at ATG (Kozak, Cell 44:283, 1986). This was achieved by mutating the first amino acid residue after the initiation codon from AAG to GAG to give the sequence TCTAGA CCACCATGGAG, where the Kozak consensus sequence is underlined and TCTAGA is an XbaI site. Therefore, the signal peptide contains a substitution at the first amino acid residue after the initiation codon and another substitution at the amino acid residue at the −2 position. Since the signal peptide is cleaved off by signal peptidase inside the cell and does not appear in the secreted protein, these mutations do not affect the amino acid composition of the antibody product.

The de-immunized VL DNA was synthesized as an AflII-BamHI fragment, and the de-immunized VH DNA was synthesized as an AflII-HindIII fragment. For the VL, ligation to the genomic leader via the AflII site resulted in an XbaI-BamHI fragment encoding the signal peptide-VL. Similarly, ligation of the VH DNA to the genomic leader via the AflII site resulted in an XhoI-HindIII fragment encoding the signal peptide-VH, where XhoI replaced XbaI by linker ligation. The resultant XbaI-BamHI and XhoI-HindIII fragments were then inserted into the pdHL10 expression vector (FIG. 15), which already contains transcription regulatory elements and immunoglobulin constant region sequences (see below).

DNA Constructs Encoding the Human Constant Regions

For the light chain, the genomic human kappa constant region was used. For the heavy chain, the genomic human gamma-2 (γ2) constant regions were used, with the following modifications:

First, since the immunoglobulin γ2 hinge region contains four cysteine disulfide bonds, which lead to increased disulfide scrambling and protein aggregation during purification, it was replaced by genetic engineering using a modified γ1 hinge region as follows. The construction of the Fcγ2h DNA encoding the modified γ1 hinge followed by the CH2 and CH3 regions of γ2 has already been described (Lo et al. Protein Engineering, Design & Selection, 18:1, 2005).

In order to replace the γ2 hinge region exon in the human Igγ2 gene with the modified γ1 hinge region exon, we used polymerase chain reaction (PCR) to reintroduce the PstI restriction site immediately upstream of the hinge exon using the Fcγ2h DNA as template. The forward primer has the sequence 5'-ctgcagAGCCCAAATCTTC, where ctgcag is the PstI site originally present at the end of the intron (lower case), with ag being the splice acceptor site, and AGC-CCAAATCTTC is the 5' end of the modified γ1 hinge region exon (upper case). The reverse primer has the sequence 5'-cagctggggcctgtccctg, which hybridize to a sequence in the intron between the hinge region and CH2 exons. The resultant 130-bp PstI-PvuII PCR product containing the modified γ1 hinge region exon, after cloning and sequence verification, was used to replace the corresponding fragment in the Igγ2 gene in the pdHL10 expression vector (see below).

Second, a mutation of Asn-297 in the CH2 domain to Gln (N297Q), was introduced by overlapping PCR to remove the N-glycosylation signal, which abrogates effector functions and prolong serum half-life of antibody. In addition, Phe-296 was mutated to Ala, which removes any potential T helper cell epitopes created by the N297Q mutation. Third, there is a SmaI restriction site located about 280 bp upstream of the translation stop codon in the wild-type DNA sequence encoding the CH3 domain. This SmaI site was destroyed by the introduction of a silent mutation (TCC to TCA). Another silent mutation was introduced to create a new, unique SmaI site 4 bp upstream of the stop codon (Lo et al. Protein Engineering 11:495, 1998) to facilitate genetic manipulation.

Construction of Plasmid pdHL10 (FIG. 15)

The expression vector pdHL10 is derived from pdHL7, which had been described previously (Gillies et al. J. Immunol. 160:6195, 1998). As in pdHL7, the two transcriptional units for the L and H chains in pdHL10 contain the CMV enhancer-promoter (Boshart et al., Cell 41:521-530, 1985). The DNA for the CMV enhancer-promoter was obtained from an AflIII-HindIII fragment of the commercially available pcDNAI (Invitrogen Corp., San Diego, Calif.).

The major difference between pdHL7 and pdHL10 is in the transcription unit for the dihydrofolate reductase (DHFR) selection marker. The SV40 enhancer for this transcription unit was destroyed in pdHL10 as follows. There are two 72-bp repeats in the SV40 enhancer/promoter, and within each 72 bp is a SphI restriction site. Ligation of the SalI site 5' of the enhancer to the distal SphI site through an oligonucleotide linker-adaptor resulted in the deletion of 120 bp from the two 72-bp repeats. Such enhancerless promoter should give a much lower expression level of the DHFR selection marker. This, in theory, should result in fewer stably transfected cell clones, which, in order to survive the drug selection, might have the plasmid integrated into an active transcription region of a chromosome so that sufficient DHFR was expressed from the enhancerless promoter. The genes of interest, driven by fully functional enhancers and promoters, should be expressed at even higher levels in this active transcription region. In addition, the orientation of this attenuated transcription unit was reversed in pdHL10, so that the CMV enhancer for the L chain cannot exert a direct effect on the distal SV40 promoter.

The construct pdHL10-DI-17E6γ2h(N297Q) was extensively mapped by restriction endonuclease digestions (FIG. 15). The coding regions of the entire L and H chains were completely sequenced. Its prominent features are described in the following Table:

| Base pair (Bp) # | Description | Literature | Source of Sequence Information |
|---|---|---|---|
| 0002 (EcoRI)-0665 (XbaI) | CMV enhancer and promoter | Boshart M et al. (1985), Cell 41, 521-530 | Locus HS5IEE, Accession K03104; Sequence confirmed at EMD Lexigen |
| 0665 (XbaI)-1112 | genomic leader of a mouse immunoglobulin L chain | Schaeble KF et al. (1999), Eur. J. Immunol. 29, 2082-2086 | Locus MMU231201, Accession AJ231201; Coding sequence confirmed at EMD Lexigen, but 6 nt variations in intron[1] |
| 1113-1434 | De-immunized 17E6 VL | Provided in FIG. 1A | Sequence confirmed at EMD Lexigen |
| 1435 (BamHI at 1442)-1784 | Intron between VL and CL | Kawasaki K (2001), Eur. J. Immunol. 31, 1017-1028 | NG_000834 in Genbank; Sequence confirmed at EMD Lexigen |
| 1785-2107 | CL coding region and translation stop codon | Kawasaki K (2001), Eur. J. Immunol. 31, 1017-1028 | NG_000834 in Genbank; Sequence confirmed at EMD Lexigen |
| 2108-2971 (SalI) | 3' untranslated region and polyadenylation signal of the human immunoglobulin kappa chain gene | Kawasaki K (2001), Eur. J. Immunol. 31, 1017-1028 | NG_000834 in Genbank; Sequence confirmed at EMD Lexigen |
| 2971 (SalI)-3638 (XhoI) | CMV enhancer and promoter | Boshart M et al. (1985), Cell 41, 521-530 | Locus HS5IEE, Accession K03104; Sequence confirmed at EMD Lexigen |
| 3638 (XhoI)-4091 | Genomic leader of a mouse immunoglobulin L chain | Schaeble KF et al. (1999), Eur. J. Immunol. 29, 2082-2086 | Locus MMU231201, Accession AJ231201; Coding sequence confirmed at EMD Lexigen, but 6 nt variations in intron[2] |
| 4092-4446 | De-immunized 17-E6 VH | Provided in FIG. 2 | Sequence confirmed at EMD Lexigen |
| 4447 (HindIII at 4454)-6264 | immunoglobulin □2 gene constant regions with modified □1 Hinge | Krawinkel U. et al. (1982), EMBO J. 1 (4), 403-407 | Locus HUMIGCD1, Accession J00230 V00554; Coding sequence confirmed at EMD Lexigen, but 4 nt variations in intron[3-5] |
| 6265 (XhoI at 6266)-6515 | 3' untranslated region and polyadenylation signal of SV40 late region | Forsman ZH et al. (2004), J. Virol. 78, 9306-9316 | Accession AF316141; Sequence confirmed at EMD Lexigen |
| 6516-8809 (EcoRI) | Origin of replication and P-lactamase gene from pBR322 | Sutcliffe JG (1978), Proc. Natl. Acad. Sci. U.S.A. 75, 3737-3741 | Accession J01749; Sequence partially confirmed (6516 to 7192) at EMD Lexigen |

| Base pair (Bp) # | Description | Literature | Source of Sequence Information |
|---|---|---|---|
| 8809(EcoRI)-9038 | SV40 promoter | Ilyinskii PO et al, (1992) J. Virology 66, 6353-6360. | M99359.1 GI:310698 in Genbank; Sequence confirmed at EMD Lexigen |
| 9039-9602 | DHFR cDNA | Simonsen CC and Levinson A D (1983), Proc. Natl. Acad. Sci. U.S.A. 80, 2495-2499 | Sequence confirmed at EMD Lexigen |
| 9603-9687 | 3'-untranslated region of DHFR fused to polyadenylation signal of SV40 early region via ligation of Bgl II sticky end to Bcl I sticky end | Strausberg R L (2002), Proc. Natl. Acad. Sci. U.S.A. 99, 16899-16903 | Accession BC005796; Sequence confirmed at EMD Lexigen |
| 9688-9924 | Polyadenylation signal of SV40 early region | Forsman ZH et al. (2004), J. Virol. 78, 9306-9316 | Accession AF316141; Sequence confirmed at EMD Lexigen |

[1] Six nucleotide (nt) variations in the intron of the leader were found between the pdHL10-DI-17E6γ2h(N297Q) vector and the published sequences. The pdHL10-DI-17E6(C60Y)γ2h(N297Q) vector contains G at 801, T at 985, C at 993, T at 1006, T at 1045 and A at 1071. The published sequence contains C, A, A, G, AC (an additional nt), and G at these respective positions.
[2] Six nucleotide (nt) variations in the intron of the leader were found between the pdHL10-DI-17E6γ2h(N297Q) vector and the published sequence. The pdHL10-DI-17E6(C60Y)γ2h(N297Q) vector contains G at 3780, T at 3964, C at 3972, T at 3985, T at 4024 and A at 4050. The published sequence contains C, A, A, G, AC (an additional nt), and G at these respective positions.
[3] Two nucleotide (nt) variants in the intron between CH2 and CH3 were found between the pdHL10-DI-17E6γ2h(N297Q) vector and the published sequence. The pdHL10-DI-17E6(C60Y)γ2h(N297Q) vector contains A at 5908 and A at 5922. The published sequence contains G at both respective positions.
[4] One nucleotide (nt) variant in the CH1 was found between the pdHL10-DI-17E6γ2h(N297Q) vector and the published sequence. The pdHL10-DI-17E6(C60Y)γ2h(N297Q) vector contains G at 4736. The published sequence contains C at this position.

Generation of Production Cell Clones and Research Cell Banks

Transfection and Selection of High-Producing Clones

The expression plasmid pdHL10-DI-17E6γ2h(N297Q) linearized by the restriction endonuclease FspI, which cut once in the sequence encoding the β-lactamase, was used to transfect NS0-LD cells by electroporation. Electroporation was performed using a Gene Pulser Xcell™ System (BioRad, Hercules, Calif.) with settings at 250 volts and 15 ms pulse length. Stably transfected clones were selected by growth in Super CD medium supplemented to contain 200 nM methotrexate (Sigma, Cat. No. M-8407). The Super CD medium contains 9.69 g/L AGT CD Hybridoma medium (Invitrogen, P/N RM-00-136), 2.52 g/L sodium bicarbonate (EMD, P/N SX0320-3), 30 ml/L CD Acid Soluble Concentrate (Invitrogen, P/N 00-0336DK), 1.46 g/L L-glutamine (Sigma, P/N G8540), 3 g/L glucose (Sigma, P/N G-5400), 2 g/L BD Select Soytone (Becton Dickenson, P/N 212488), and 2 g/L BD Ultrafiltered Select Phytone (Becton Dickenson, P/N 210931). Supernatants of about 474 stable clones from twelve 96-well plates were assayed by anti-human Fc ELISA to identify high producers. The expression levels of selected clones were further confirmed by recombinant Protein A affinity (rPA) chromatography. Clone #395, which produced 607 μg/ml of DI-17E6γ2h(N297Q) (by rPA) in terminal stationary culture in a 25 cm² T flask, was chosen for subcloning by limiting dilutions.

Attempts to subclone in Super CD medium were not successful. Therefore, clone #395 was adapted to growth in DMEM/F12 medium (Invitrogen, cat. #21041-025) supplemented to contain 5 μM Tropolone (Sigma, cat. # T7387), 10 μL ethanolamine (Sigma, cat. # E0135), 10 μg/mL insulin (bovine, lyophilized, Invitrogen, Cat. No. 13007-018), 2 g/L Hypep 4601 (Quest International, cat. #5Z10419) and 2 g/L Hypep 1510 (Quest International, cat. #5X59053), 3.5 mM L-glutamine (Invitrogen, Cat. No. 25030-081), and 200 nM methotrexate (Sigma, Cat. No. M-8407) for one passage and subcloned in a 1:1 mixture of the complete DMEM/F12 medium with 200 nM methotrexate and conditioned complete DMEM/F12 medium (conditioned from a culture of the untransfected host NS0-LD cells, spun down and then filtered). For subcloning, cells were plated 1, 5, 10 cells/well in 96-well plates. In about two weeks, subclones appeared in the plates containing 10 and 5 cells/well. The subclones in the wells were inspected under the microscope to ensure that there was only one visible clone in the well. Supernatants of 16 subclones from two 96-well plates (10 cells/well) and 1 subclone from two 96-well plates (5 cells/well) were assayed by anti-human Fc ELISA and the high-producing clones were chosen for rPA analysis. The best subclones were #395-2 and #395-6, producing 669 μg/ml and 735 μg/ml DI-17E6γ2h (N297Q) (by rPA) in terminal stationary culture in 75 cm² T flasks.

Expression of the Antibody

Mammalian expression plasmids were constructed, transfected into NS/0 cells, and stable transfectants were isolated. Typically, NS/0 cells were stably transfected with an expression vector and introduced into a 75 milliliter culture in a T-flask and grown for three days, such that the cell density was about 400,000 cells per milliliter. Under these conditions, the concentration of secreted DI-17E6 was about 50-100 micrograms/ml.

Purification of Antibody

The antibody can be purified using, in sequence, some or all of the following steps: Abx Mixed Resin column chromatography, recombinant Protein A chromatography, and Q Sepharose column chromatography, followed by Pellicon 2 tangential flow diafiltration for buffer exchange into formulation buffer. Virus inactivation and removal steps are interdigitated into these steps. The virus inactivation and removal steps are not necessary for purification per se, but are used to satisfy regulatory considerations.

Assay to determine binding of DI17E6 antibody to alpha V integrin receptor subunit The ability of the DI17E6 antibody to bind alpha V integrin was assayed using an ELISA. Briefly, various amounts of antibody were added to wells containing alpha V integrin, wells were then washed, and the bound antibody was assayed according to standard procedures.

Example 2

Generation of a Diversity of Antibody Mutations to Find Out Optimum Expression and Binding Affinity Patterns Summary of data on increasing expression level of DI-17E6 by reengineering Problem in expression: The expression levels of the deimmunized versions were even lower than that of the chimeric:

|  | Transient in PER.C6 | NS0 from ECACC | NS0-LD |
|---|---|---|---|
| ch17E6-g2h, g4h and g4h(NtoQ) | ~3-4 ug/ml | ~15 ug/ml | ND |
| deImm17E6 VH33-VL60.2-g2h(FNtoAQ) | 0.3 ug/ml | ~1 mcg/ml (96-well) | ~1.6 ug/ml |
| deImm17E6 VH33-VL49-g2h(FNtoAQ) | 0.7 ug/ml | ~3 ug/ml | ~10 ug/ml |

To increase the expression level of delmm17E6 VH33-VL49/VL60.2-g2h(FN to AQ), we mutated:
a.) C60 to S and Y in CDR2 of VH.
b.) GEM back to DGTV in VL to restore a H-bond network but a potential weak T cell epitope.
c.) V20M reversion in VH The results of two sets of transient transfection were summarized below:

Delmm 17E6 Mutant (C60S) Expression Level Vs Other 17E6 (Transient Transfection in Per.C6, 24 ug in 10 cm plate):

|  | Day 1 | Day 4 |
|---|---|---|
| DeImm 17E6[VL49/VH33(C60S)]-g2h(FN->AQ) #15 | 15.7 ng/ml | 956 ng/ml |
| DeImm 17E6[VL49/VH33(C60S)]-g2h(FN->AQ) #16 | 13.1 ng/ml | 734 ng/ml |
| DeImm 17E6[VL49/VH33]-g2h(FN->AQ) #44 (DI control) | 12.4 ng/ml | 631 ng/ml |
| DeImm 17E6[VL60.2/VH33]-g2h(FN->AQ) #1 (DI control) | 8.3 ng/ml | 589 ng/ml |
| 17E6-g4h(FN->AQ) #1 (chimeric control) | 174 ng/ml | 2716 ng/ml |
| 17E6-g2h #6 (chimeric control) | 149 ng/ml | 3582 ng/ml |

Delmm 17E6 Mutants Expression Level (Transient Transfection in PER.C6, 24 □g in 10 cm Plate):

|  | Day 2 | Day 4 |
|---|---|---|
| DeImm 17E6[VL49(GEAA->DGTV)/VH33]-g2h(FN->AQ) #1 | 192 ng/ml | 1187 ng/ml |
| DeImm 17E6[VL60.2(GEAA->DGTV)/VH33]-g2h(FN->AQ) #20 | 120 ng/ml | 949 ng/ml |
| 17E6-g2h #66 (chimeric control) | 271 ng/ml | 1442 ng/ml |
| DeImm 17E6[VL60.2/VH33]-g2h(FN->AQ). #1 (DI control) | 65 ng/ml | 883 ng/ml |

Transfections with Miniprep DNA:

|  |  |  |
|---|---|---|
| DeImm 17E6[VL49/VH33(V20M)]-g2h(FN->AQ) #5(mini, 40 ul) | 5 ng/ml | 0.77 ng/ml |
| DeImm 17E6[VL49/VH33(C60Y)]-g2h(FN->AQ) #10(mini, 40 ul) | 119 ng/ml | 745 ng/ml |

C60S has only marginal improvement, whereas C60Y result is promising. If the C60Y result holds with maxiprep DNA, the transfections of which have been done, we will have to make sure that there is no loss in binding affinity. The GEAA to DGTV reversion improved expression by around 0.5-fold to 2-fold. The V20M result with miniprep DNA is not reliable, but transfection has been repeated with maxiprep DNA.

Improving expression of delmm17E6: The following new constructs were used to transfect NS0 cells:
pdHL10-DI-17E6[VH33(C60Y)/VL49(DGTV)]-g2h (FN→AQ)
pdHL10-DI-17E6[VH33(C60Y)/VL60.2(DGTV)]-g2h (FN→AQ)
pdHL10-DI-17E6[VH33(C60S)/VL49(DGTV)]-g2h (FN→AQ)
pdHL10-DI-17E6[VH33(C60S)/VL60.2(DGTV)]-g2h (FN→AQ)
pdHL10-17E6-g2h(FN-AQ) (This was made to compare expression level with 17E6g2h.)

Test for transient expression in PER.C6 by HuFc-ELISA:

|  | Day 2 | Day 7 |
|---|---|---|
| DI-17E6[VH33(C60Y)/VL49(DGTV)]-g2h(FN->AQ) | 304 | 2518 ng/ml |
| DI-17E6[VH33(C60Y)/VL60.2(DGTV)]-g2h(FN->AQ) | 233 | 1674 ng/ml |
| DI-17E6[VH33(C60S)/VL49(DGTV)]-g2h(FN->AQ) | 433 | 2734 ng/ml |
| DI-17E6[VH33(C60S)/VL60.2 (DGTV)]-g2h(FN->AQ) | 467 | 3138 ng/ml |
| 17E6-g2h(FN-AQ) (chimeric control) | 587 | 5425 ng/ml |
| 17E6-g2h (chimeric control) | 537 | 3683 ng/ml |
| DI-17E6[VH33/VL60.2]- g2h(FN->AQ) (DI control) | 48 | 669 ng/ml |
| DI-17E6[VH33/VL60.2(DGTV)]- g2h(FN->AQ) | 142 | 1302 ng/ml |
| DI-17E6[VH33(C60Y)/VL49]- g2h(FN->AQ) | 371 | 1535 ng/ml |

The ELISA data showed that expression levels of 17E6-g2h(FN-AQ) and 17E6-g2h were comparable. Surprisingly the expression levels of (C60S)/(DGTV) combinations were higher than those of (C60Y)/(DGTV), whereas earlier results showed that C60Y and DGTV separately increased the expression level of Delmm17E6 from 1× to 2-3×, whereas C60S has minimal benefit.

17E6VH/425VL-g2h(FN to AQ) and the following transient transfections were done:

|  | Fc ELISA |
|---|---|
| 17E6VH/425VL-g2h(FN to AQ) in triplicates: | 28.5, 26.7, 18.7 ug/ml |
| DI-17E6[VH33(C60Y)/VL49(DGTV)]-g2h(FN->AQ) in duplicates | 2.1, 1.7 |
| DI-17E6[VH33(C60S)/VL49(DGTV)]-g2h(FN->AQ) in duplicates | 2.7, 1.7 |
| 17E6-g2h(FN->AQ) in duplicates (chimeric control) | 4.9, 4.0 |
| 425EU Ab in duplicates (425 control) | 27.4, 20.0 |

Clearly, changing the VL increased the expression level to that of the 425 Ab!

Unfortunately, 17E6VH/425VL-g2h(FN to AQ) did not bind avb3 in the binding ELISA (see FIG. 21).

In order to solve the expression/binding problem the following molecules were constructed:

T8P and A44P substitutions in delmm17E6 VL:
DI-17E6 VL60.2(DGTV) with T8P/DI-17E6 VH33(C60Y)-g2h(FN to AQ)
DI-17E6 VL60.2(DGTV) with A44P/DI-17E6 VH33(C60Y)-g2h(FN to AQ)
DI-17E6 VL60.2(DGTV) with T8P/DI-17E6 VH33(C60S)-g2h(FN to AQ)
DI-17E6 VL60.2(DGTV) with A44P/DI-17E6 VH33(C60S)-g2h(FN to AQ)

Cells were transfected, although the final constructs are being confirmed by sequencing (since restriction digestion cannot distinguish recombinant from parental). Combining the T8P and A44P may be necessary. Grafting the 17E6 delmmVL CDRs into the delmm425VL FRs. The expression levels of delmm425VL/delmm17E6 VH were tested, because delmm425 VL may not be expressed to the same high level as hu425 VL. The DI-425VL1, was used, but with a P to L reversion (VL1 did not bind). Consequently, the P to L reversion in CDR3 was made to restore the binding. It was paired up with delmm17E6 VH33 (construct a below) and ch17E6 VH (construct b below). Transient transfections were done using controls Hu425VL/ch17E6 VH (construct c below), and ch17E6.

| Constructs | Transient expression by Fc ELISA |
|---|---|
| a.) DI-425VL1(P to L)/deImm17E6 VH33-g2h(FN to AQ) | 25 |
| b.) DI-425VL1(P to L)/ch17E6 VH-g2h(FN to AQ) | 69 |
| c.) Hu425VL/ch17E6 VH-g2h(FN to AQ) | 8394 |
| d.) 17E6-g2h(FN to AQ) | 643 |

The transient results showed that while (c) gave very high expression level, constructs a and b with DI-425VL gave levels even lower than that of the ch17E6.

NS0-LD production clones with
pdHL10-425VLFRs/DI17E6VL60.2CDRs/17E6VH33(C60S)-g2h(FN→AQ)-Ab and
pdHL10-425VLFRs/DI-17E6VL60.2CDRs/17E6VH33(C60Y)-g2h(FN→AQ)-Ab.

Grafts with (FR1+FR2 only) are not expressed well and bind poorly, whereas grafts with (FR3+FR4) only are expressed quite well and bind well. FR4 only did not work. The table below shows that FR3 only did not increase expression.

| Stable clones in NS0-LD in DMEM/F12 in T25 flasks | |
|---|---|
| Protein Name/clone# | rPA (ug/ml) |
| DI-17E6VL60.2CDR-425VLFRs/VH33(C60Y)-g2h(FN−>AQ) | |
| #423 | 38 |
| #433 | 135 |
| #434 | 62.5 |
| #10 | 381 |
| DI-17E6VL60.2CDR-425VLFR3FR4/VH33(C60Y)g2h(FN−>AQ) | |
| #1 | 29.5 |
| #2 | 31.3 |

DI-17E6-g2h(NtoQ)(C60Y) was chosen as the final molecule because of the high expression level of the stable NS0-LD clones and because it retains binding affinity.

Example 3

To characterize integrin specificity of DI-17E6, ELISA, cellular ELISA and flow cytometry analysis were used, and these allowed us to identify the $\alpha v$ chain of integrins as the specific ligand for EMD 525797.

EMD 525797 recognizes purified $\alpha v$-integrins but, as expected, had no reactivity against purified $\alpha IIb\beta 3$. EMD 525797 also interacts with human cell lines with $\alpha v$-integrins on their cell surface, independently of the associated $\beta$-chain subunit. EMD 525797 and LM609 immuno-reactivities are depicted in the following tables:

Immune-Reactivity on Purified Integrins

| | $\alpha v\beta 3$ | $\alpha v\beta 5$ | $\alpha IIb\beta 3$ |
|---|---|---|---|
| EMD 525797 | + | + | − |
| LM609 | + | − | − |

Reactivity of LM609 (murine monoclonal antibody anti-$\alpha v\beta 3$) is shown for comparison.

| Transient transfection in PER.C6 | | | | | |
|---|---|---|---|---|---|
| Protein Name | huFc-ELISA (ug/ml) | huFc-ELISA (ug/ml) | huFc-ELISA (ug/ml) | huFc-ELISA (ug/ml) | huFc-ELISA (ug/ml) |
| DI-17E6VL60.2CDR-425VLFR3/VH33(C60Y)-g2h(FN−>AQ) | 0.79 | 2.72 | | | |
| DI-17E6VL60.2CDR-425VLFR3FR4A/VH33(C60Y)-g2h(FN−>AQ) | 14.17 | 25.36 | 19.6 | | 17 |
| DI-17E6VL60.2CDR-425VLFRs/VH33(C60Y)-g2h(FN−>AQ) | 20.78 | 31.76 | 24.3 | | 28.5 |
| DI-17E6VL60.2CDR-425VLFR1FR2/VH33(C60Y)-g2h(FN−>AQ) | | | 4.5 | | 6.2 |
| DI-17E6VL60.2CDR-425VLFR4/VH33(C60Y)-g2h(FN−>AQ) | | | | 1.9 | |
| DI-17E6VL60.2CDR-425VLFR1/VH33(C60Y)-g2h(FN−>AQ) | | | | 3 | |
| DI-17E6VL60.2CDR-425VLFRs/17E6VH-g2h(FN−>AQ) | 21.65 | 33.7 | 35.1 | 19 | 25.9 |
| 425VL/17E6VH-g2h(FN−>AQ) | 35.14 | 53.66 | 47.3 | 40 | 51.9 |
| 17E6-g2h(FN−>AQ) | 3.74 | 8.86 | 9.8 | 4 | 8.7 |

Immune-Reactivity on Tumor Cell Lines

| | Test cell | | | | | | | | |
|---|---|---|---|---|---|---|---|---|---|
| | M21 | M21-L | MeWo | HT29 | Colo205 | SKBR-3 | A498 | V+B2 | CV-1 |
| | | | | | αv-integrin pattern | | | | |
| | αvβ3 αvβ5 | No αv-integrins | αvβ3 αvβ5 | αvβ6 αvβ5 | αvβ6 αvβ5 | αvβ5 | αvβ3 | αvβ1 | αvβ3 |
| EMD 525797 | + | − | + | + | + | + | + | + | + |
| LM609 | + | − | + | − | − | − | + | − | nd |

Reactivity of LM609 (murine monoclonal antibody anti-αvβ3) is shown for comparison. Human tumor cell lines: M21, M21-L, and MeWo melanomas; HT29 and Colo205 colon carcinomas; SKBR-3 breast carcinoma; A498 renal carcinoma; and V+B2 ocular melanoma. CV-1 is a green monkey cell line.

EMD 525797 recognizes human and monkey αv-integrins only, and no other species. The molecular basis for this unusual profile has been unequivocally established by epitope mapping, sequence comparison, and x-ray co-crystallography. The epitope recognized by DI-17E6 is confirmed as unique to human and monkey by immuno precipitation and western blotting analysis performed with several species.

Example 4

Immunogenicity

The data show that DI-17E6 is much less immunogenic than the original murine 17E6 version. FIG. 2 shows that murine 17E6 serum levels given to an experimental animal decrease considerable along with the experiment time.

On the other hand, serum levels of monkey antibodies with specificity against murine 17E6 increased along with the experiment time and inversely correlate with the falling murine 17E6 serum levels.

This inverse correlation suggests that murine 17E6 is highly immunogenic in monkeys and men, and therefore monkeys or humans develop a MAMA respectively HAMA response, which adversely affects the pharmacokinetics of murine 17E6.

Another aim of the study was furthermore to assess anti-angiogenic activity of DI-17E6 in a monkey Matrigel plug experiment. For comparison, murine 17E6 was used as reference compound.

Four different groups containing one single animal each were used: vehicle, murine 17E6 at 30 mg/Kg, DI-17E6 at 30 mg/Kg, and DI-17E6 at 10 mg/Kg. Monkeys received one i.v. injection (in the arm) of murine 17E6 or DI-17E6 at the beginning of the experiment which continued for 6 days. (FIG. 2)

Serums were collected at three different points (from the legs): immediately before antibody injection, immediately (1-2 minutes) after antibody injection, and at the end of the study before animal sacrifice. Levels of both murine 17E6, and DI-17E6 were analyzed. To detect given serum dilution) were found at the two different time points in serum: immediately after antibody administration and at the end of the study. This was observed in both DI-17E6 treated groups: 10 and 30 mg/Kg.

However, serum levels of murine 17E6 were only detectable immediately after antibody injection. They were almost null by the end of the study. Experiment revealed huge neutralizing monkey anti-murine antibody (MAMA) response against 17E6, which clearly points to the high immunogenicity of murine 17E6 in monkeys and other primates such as humans. This response led to rapid and complete clearing of 17E6 from the monkey serum.

Therefore, this suggests that murine 17E6 is cleared more rapidly in humans, by a huge HAMA response.

In another study the pharmacy kinetic parameters of a single dose of DI-17E6 in monkeys was assessed and in addition, this study was planned to investigate the immunogenicity of DI-17E6. DI-17E6 was given at 1 mg/Kg as a single i.v. injection at the beginning of the experiment. Length of the assay was 6 weeks. Serums were drawn pre-dose, and 1, 3, and 6 weeks after administration. Levels of monkey antibodies against DI-17E6 were analyzed. In this study, immunogenicity was directly addressed using a specific sandwich ELISA method designated for this type of studies (method not validated yet).

FIG. 3 shows that no monkey antibodies against DI-17E6 could be detected in any time point of the assay, therefore clearly indicating that low monkey anti-human (MAHA) response was generated.

In additional experiments, immunogenicity of both antibodies was addressed indirectly, by studying the sustained serum levels of the two variant 17E6 antibodies, murine 17E6 and DI-17E6. DI-17E6 had high serum levels at each time-point of the assay, suggesting that DI-17E6 triggered no antibody response, and so was not immunogenic in monkeys. By contrast, murine 17E6 could not be detected (very low to null levels) in serum by the last time point. This indicates again that monkeys mounted a clearing MAMA response against murine 17E6 due to its immunogenicity.

Because 17E6 was de-immunized based on eliminating human T-cell recognition epitopes, the DI-17E6 immunogenic is expected to be low in humans, allowing repeated therapeutic dosing without the complication of raising an immune response that might counteract therapeutic efficacy. This is a unique finding which due to the high degree of homology between monkey and human genome, including the 17E6 antigen alpha-v integrin, can be readily extended to the human situation.

This was meanwhile confirmed by a first clinical study carried out in the US in 2006/2007. DI-17E6 was administered to 5 groups of healthy volunteers (each group contains 6 volunteers) in different doses: 200 mg/Kg; 120 mg/Kg; 70 mg/Kg, 35 mg/Kg corresponding to 250 mg, 500 mg, 1000 mg and 1500 mg/dose. Only in the group of 250 mg one volunteer developed anti-drug antibodies, whereas in the higher dose groups (these doses are in the range of o standard therapeutic administration) no volunteer developed any immune response against DI-17E6. In contrast to that, mouse 17E6 develops in animal models a strong immune response.

According to the T-cell epitope mapping and eliminating method used herein, wherein the sequence of the mouse antibody is split in overlapping peptides the loss of immunogenicity after de-immunization was confirmed by a distinct decrease of scoring in an in vitro T-cell assay indicating that potential human T-cell epitopes had been deleted. Accordingly, the score decreases from 147 (mouse 17E6) to 92 (DI-17E6) in the light chains, and from 181 (mouse 17E6) to 85 (DI-17E6) in the heavy chains.

Mouse 12E6 light chain

| Posn | Sequence | | nBind | Score | Mean |
|---|---|---|---|---|---|
| 15 | LGDRVIISC | (SEQ ID No. 46) | 4 | 100.16 | 25.04 |
| 19 | VIISCRASQ | (SEQ ID No. 47) | 31 | 1177.12 | 37.97 |
| 20 | IISCRASQD | (SEQ ID No. 48) | 1 | 22.34 | 22.34 |
| 21 | ISCRASQDI | (SEQ ID No. 49) | 3 | 78.13 | 26.04 |
| 29 | ISNYLSWYQ | (SEQ ID No. 50) | 7 | 169.20 | 24.17 |
| 33 | LSWYQQKPD | (SEQ ID No. 51) | 1 | 20.93 | 20.93 |
| 44 | VKLLIFYTS | (SEQ ID No. 52) | 12 | 303.43 | 25.29 |
| 46 | LLIFYTSKL | (SEQ ID No. 53) | 24 | 940.44 | 39.18 |
| 47 | LIFYTSKLH | (SEQ ID No. 54) | 15 | 497.37 | 33.16 |
| 48 | IFYTSKLHS | (SEQ ID No. 55) | 34 | 1151.58 | 33.87 |
| 50 | YTSKLHSGV | (SEQ ID No. 56) | 1 | 25.29 | 25.29 |
| 54 | LHSGVPSRF | (SEQ ID No. 57) | 2 | 52.00 | 26.00 |
| 71 | YSLTISNLD | (SEQ ID No. 58) | 3 | 76.60 | 25.53 |
| 83 | IATYFCQQG | (SEQ ID No. 59) | 2 | 40.82 | 20.41 |
| 86 | YFCQQGNTF | (SEQ ID No. 60) | 4 | 84.56 | 21.14 |
| 98 | FGGGTKVEM | (SEQ ID No. 61) | 3 | 94.75 | 31.58 |

Total score: 147

Del 17E6 final light chain

| Posn | Sequence | | nBind | Score | Mean |
|---|---|---|---|---|---|
| 2 | *IQMTQSPSS | (Residues 2-10 of SEQ ID No. 2) | 22 | 615.49 | 27.98 |
| 15 | *VGDRVTITC | (SEQ ID No. 62) | 5 | 139.09 | 27.82 |
| 19 | *VTITCRASQ | (SEQ ID No. 63) | 17 | 421.29 | 24.78 |
| 21 | ITCRASQDI | (SEQ ID No. 64) | 3 | 86.42 | 28.81 |
| 29 | *ISNYLAWYQ | (SEQ ID No. 65) | 4 | 98.65 | 24.66 |
| 46 | LLIYYTSKI | (SEQ ID No. 66) | 33 | 1195.64 | 36.23 |
| 47 | LIYYTSKIH | (SEQ ID No. 67) | 15 | 497.37 | 33.16 |
| 48 | IYYTSKIHS | (SEQ ID No. 68) | 30 | 906.02 | 30.20 |
| 49 | YYTSKIHSG | (SEQ ID No. 69) | 1 | 20.00 | 20.00 |
| 50 | YTSKIHSGV | (SEQ ID No. 70) | 1 | 25.29 | 25.29 |
| 54 | IHSGVPSRF | (SEQ ID No. 71) | 2 | 52.00 | 26.00 |
| 71 | YTFTISSLQ | (SEQ ID No. 72) | 4 | 115.43 | 28.86 |
| 73 | *FTISSLQPE | (SEQ ID No. 73) | 3 | 71.05 | 23.68 |
| 83 | IATYYCQQG | (SEQ ID No. 74) | 2 | 40.82 | 20.41 |
| 86 | YYCQQGNTF | (SEQ ID No. 75) | 4 | 88.56 | 22.14 |
| 94 | *FPYTFGQGT | (SEQ ID No. 76) | 2 | 44.83 | 22.41 |
| 98 | *FGQGTKVEI | (SEQ ID No. 77) | 5 | 135.81 | 27.16 |

Total score: 92

17E6 mouse heavy chain

| Posn | Sequence | | nBind | Score | Mean |
|---|---|---|---|---|---|
| 2 | VQLQQSGAE | (SEQ ID No. 78) | 5 | 129.45 | 25.89 |
| 4 | LQQSGAELA | (SEQ ID No. 79) | 6 | 140.28 | 23.38 |
| 18 | VKMSCKASG | (SEQ ID No. 80) | 27 | 881.03 | 32.63 |
| 27 | YTFSSFWMH | (SEQ ID No. 81) | 2 | 46.55 | 23.28 |
| 29 | FSSFWMHWV | (SEQ ID No. 82) | 3 | 80.61 | 26.87 |
| 32 | FWMHWVKQR | (SEQ ID No. 83) | 18 | 546.68 | 30.37 |
| 33 | WMHWVKQRP | (SEQ ID No. 84) | 2 | 59.09 | 29.55 |
| 36 | WVKQRPGQG | (SEQ ID No. 85) | 9 | 229.70 | 25.52 |
| 37 | VKQRPGQGL | (SEQ ID No. 86) | 4 | 90.82 | 22.70 |
| 47 | WIGYINPRS | (SEQ ID No. 87) | 9 | 282.09 | 31.34 |
| 48 | IGYINPRSG | (SEQ ID No. 88) | 10 | 280.39 | 28.04 |
| 51 | INPRSGYTE | (SEQ ID No. 89) | 3 | 81.56 | 27.19 |
| 63 | IFRDKATMT | (SEQ ID No. 90) | 7 | 197.95 | 28.28 |
| 64 | FRDKATMTA | (SEQ ID No. 91) | 19 | 609.26 | 32.07 |
| 80 | YMQLSGLTS | (SEQ ID No. 92) | 22 | 678.41 | 30.84 |
| 81 | MQLSGLTSE | (SEQ ID No. 93) | 5 | 116.59 | 23.32 |
| 83 | LSGLTSEDS | (SEQ ID No. 94) | 3 | 63.39 | 21.13 |
| 93 | VYYCASFLG | (SEQ ID No. 95) | 11 | 297.27 | 27.02 |
| 94 | YYCASFLGR | (SEQ ID No. 96) | 2 | 51.02 | 25.51 |
| 99 | FLGRGAMDY | (SEQ ID No. 97) | 11 | 321.71 | 29.25 |
| 107 | YWGQGTSVT | (SEQ ID No. 98) | 1 | 23.40 | 23.40 |
| 108 | WGQGTSVTV | (SEQ ID No. 99) | 2 | 62.07 | 31.03 |

Total score: 181

Del 17E6 final heavy chain

| Posn | Sequence | | nBind | Score | Mean |
|---|---|---|---|---|---|
| 2 | VQLQQSGGE | (SEQ ID No. 100) | 5 | 129.45 | 25.89 |
| 18 | *VKVSCKASG | (SEQ ID No. 101) | 12 | 366.95 | 30.58 |
| 27 | YTFSSFWMH | (SEQ ID No. 102) | 2 | 46.55 | 23.28 |
| 29 | FSSFWMHWV | (SEQ ID No. 103) | 3 | 80.61 | 26.87 |
| 32 | FWMHWVRQA | (SEQ ID No. 104) | 14 | 673.39 | 48.10 |
| 33 | *WMHWVRQAP | (SEQ ID No. 105) | 2 | 52.27 | 26.14 |
| 36 | *WVRQAPGQG | (SEQ ID No. 106) | 17 | 473.32 | 27.84 |
| 37 | *VRQAPGQGL | (SEQ ID No. 107) | 8 | 276.30 | 34.54 |
| 47 | WIGYINPRS | (SEQ ID No. 108) | 9 | 282.09 | 31.34 |
| 48 | IGYINPRSG | (SEQ ID No. 109) | 10 | 280.39 | 28.04 |
| 51 | INPRSGYTE | (SEQ ID No. 110) | 3 | 81.56 | 27.19 |
| 63 | IFRDKATMT | (SEQ ID No. 111) | 7 | 197.95 | 28.28 |
| 64 | FRDKATMTT | (SEQ ID No. 112) | 10 | 304.58 | 30.46 |
| 80 | *YMELSSLRS | (SEQ ID No. 113) | 16 | 481.10 | 30.07 |
| 81 | *MELSSLRSE | (SEQ ID No. 114) | 1 | 35.56 | 35.56 |
| 86 | *LRSEDTAVY | (SEQ ID No. 115) | 12 | 357.27 | 29.77 |
| 93 | VYYCASFLG | (SEQ ID No. 116) | 11 | 297.27 | 27.02 |
| 94 | YYCASFLGR | (SEQ ID No. 117) | 2 | 51.02 | 25.51 |
| 99 | FLGRGAMDY | (SEQ ID No. 118) | 11 | 321.71 | 29.25 |
| 107 | YWGQGTSVT | (SEQ ID No. 119) | 1 | 23.40 | 23.40 |
| 108 | WGQGTSVTV | (SEQ ID No. 120) | 2 | 62.07 | 31.03 |

Total score: 85

Example 5

Although DI-17E6 does not cross-react with platelet fibrinogen receptor αIIbβ3, platelets also express some αv-integrins. To exclude possible side effects of the antibody on platelets, EMD 525797 was evaluated for inhibition of platelet aggregation in vitro with human platelet rich plasma/collagen. No anti-aggregation activity was detected neither at 160 nM or 1600 nM. Aggregation and activation studies were carried out using Platelet Rich Plasma (PRP). Thrombus formation by perfusion chamber with exposed subendothelial matrix.

The experimental outcome can be summarized (as follows: DI-17E6 does not induce any platelet activation nor platelet aggregation at any concentration (from very low to very high: 0.1 to 1000 μg/ml).

Surprisingly, DI-17E6 blocks platelet aggregation induced by a weak aggregation inducer like ADP, in a dose-dependent manner. DI-17E6 does not affect platelet aggregation induced by a strong aggregation inducer like collagen. DI-17E6 affects as well (blocks) platelet thrombus formation in the perfusion chamber, in a dose-dependent manner and reveals an anti-thrombotic activity.

The weak interference with platelet aggregation is an unexpected finding for DI-17E6 as potential which may turn out therapeutically useful as the vicinity of a tumor is characterized by many thrombogenic vascular sites.

Example 6

In Vivo Anti-Angiogenic Activity in Mouse Xenograft Tumor Models

Human skin containing human M21 melanoma cells were grafted by implantation/transplantation onto SCID or nude mice. Experimental tumors grew in this tissue after intradermal inoculation of tumor cells and the initial angiogenic vasculature was derived from vessels in the human skin. In the next experiment, the use of M21-L cells that have no av-integrins means that only those integrins expressed on the endothelial cells within the grafted human skin were targeted.

DI-17E6 inhibited growth of M21-L tumors in the SCID mouse-human skin chimera model and was active at a dose of 1 mg/dose administered i.p. 3 times per week starting treatment one day after tumor cell inoculation (FIG. 4). This finding demonstrates that EMD 525797 elicits an anti-angiogenic effect on tumor growth.

Example 7

Inhibition of Growth Factor Induced Angiogenesis in the Matrigel Plug Model in Monkeys by i.v. Injection of EMD 525797

To extend the assessment of the anti-angiogenic activity of EMD 525797, it was tested in a tumor-free model in monkeys, where angiogenesis is induced by the angiogenic factor bFGF.

Matrigel plugs containing bFGF were implanted s.c. into the abdomen of healthy Cynomologus monkeys. The animals were injected once with EMD 525797 i.v. at either 10 mg/Kg or 30 mg/Kg. Evaluation of angiogenesis was carried out 6 days after by quantification of the hemoglobin content in the Matrigel plugs. Treatment of monkeys with EMD 525797 blocked new blood vessel formation in a dose-dependent manner, being highly efficacious at 30 mg/Kg, but inactive at 10 mg/Kg (FIG. 5).

Example 8

In Vitro Testing of DI17E6 in Combination with Chemotherapeutic Agents in HUVE Cells In the current study, representative chemotherapeutic agents from different classes of inhibitors in combination with the alpha-v integrin inhibitor cilengitide and Di-17E6 were investigated. The experimental design gives answer to the question whether blockade of the one lowered the IC50 of the other for blockade endothelial cell growth in the presence of tumor growth factors VEGFA and FGF2. The tests were performed with HUVEC and microvessel endothelial cells, which were supplemented by VEGFA and FGF2 which stimulates the growth of such cells by a factor of up to 500%.

Plates were coated with 100 μl VN at 1 μg/ml in PBS per 96-well at 4° C. overnight. Cells were plated at 5×10e3 cells/well in 100 ul Medium 199 containing 2% FCS. After 60 minutes at 37° C. alpha V integrin blockers and chemotherapeutic agents were added alone or in combination at two-fold concentration in 100 μl/well in Medium 199 plus 2% FCS and 20 ng/ml FGF-2, for the HUVE cells, or with 20 ng/ml VEGF for the HDMVEC cells (final concentration of growth factors was 10 ng/ml). When added in combination the two test substances were mixed at the starting concentrations and the mixture was serially diluted as for the single agents alone. In some assays the chemotherapeutics were serially diluted in the presence of a constant amount of the alpha V blockers at the $IC_{50}$ or $IC_{70}$ concentrations. Plates were incubated for 72 hours, then relative cell number was determined by the addition of 20 ul/well Alamar Blue (Resazurin). After 4 hours of incubation at 37° C. the fluorescence was read in a Genios plate reader (SLT) at 535/590 nm (excitation/emission).

Points were run in duplicate or in triplicate. Reagent blanks, containing media plus Alamar Blue without cells, were run on each plate. Blank values were subtracted from test values and were routinely 5-10% of uninhibited control values.

Cilengitide was tested in the range of 50 μM to 0.1 nM. Antibodies 17E6 and DI-17E6 were tested at 50 μg/ml to 0.1 ng/ml. Starting concentrations of chemotherapeutic agents that have been tested are given in the table below:

| Chemotherapeutic Agent | Mechanism of Action | Starting Concentration |
| --- | --- | --- |
| Taxol | Taxane/microtubules | 50 ng/ml |
| Etoposide | Topoisomerase II inhibitor | 100 uM |
| Vincristine | Vinca alkaloid/microtubules | 10 nM |
| Cis-platinin | Platinum analog | 200 uM |
| Camptothecin | topoisomerase 1 inhibitor | 10 uM |
| Doxorubicin | anthracycline | 1 uM |
| Melphalan | Alkylating agent | 100 uM |
| Temazolomide | Alkylating agent | 50 uM |
| Estramustine | Alkylating agent | 100 uM |
| 5-FU | antimetabolite | 100 uM |
| Gemcitabine | antimetabolite | 50 nM |

The alpha V integrin blocking substance Cilengitide (EMD 121974) and two alpha V integrin function-blocking antibodies, 17E6 (EMD 73034) and its de-immunized form DI-17E6 (EMD 525979), were tested alone and in combination with common chemotherapeutic agents in an FGF stimulation growth assay using conventional human endothelial cells (HUVEC) or in a VEGF stimulation assay using human dermal micro vascular endothelial cells. In this assay system the cells are cultured in a reduced serum (2% FCS in Medium 199) medium with FGF-2 or VEGF as the only growth stimulus. The growth factors FGF-2 turned out to be the best growth stimulant for HUVEC and VEGF was the best stimulant for HDMVEC measured using the Alamar Blue assay. HUVEC receiving 12.5 ng/ml FGF-2 showed a 406% and with VEGF a 238% increase over control cells receiving no added growth factors after 72 hours of growth on VN. n contrast, the HDM-VEC were preferentially stimulated by VEGF than FGF-2, (484%). Tests were routinely run using HUVEC in media containing 10 ng/ml FGF-2 or HDMVEC in media containing 10 ng/ml VEGF. The alpha V integrin blockers and Paclitaxel inhibited cell growth when added as single agents. In a typical test using HUVEC the $IC_{50}$ for Cilengitide was 700 nM, for 17E6 was 5 ng/ml and for DI-17E6 4 ng/ml. For Paclitaxel the $IC_{50}$ was 0.27 ng/ml when added alone but the $IC_{50}$ was reduced to 0.13 ng/ml when used in combination with Cilengitide. The antibodies 17E6 and DI-17E6 caused a reduction in $IC_{50}$ of Paclitaxel to 0.18 ng/ml and 0.1 mg/ml respectively. A typical result for DI17E6 when used in combination with Paclitaxal is shown in FIG. 6.

The additive effect of Paclitaxel with alpha V integrin blockers was obtained with HDMVEC as well. The complete list of chemotherapeutic agents tested is shown in the following Table.

| Chemotherapeutic | Cilengitide | Mab 17E6 | DI-17E6 | IC50 |
|---|---|---|---|---|
| Taxol | yes | yes | yes | 0.3 ng/ml |
| Etoposide | yes | yes | yes | 0.7 uM |
| 5FU | yes | yes | yes | 14.5 uM |
| Cisplatinin | yes | yes | yes | 13.2 uM |
| Melphalan | yes | yes | yes | 11.4 uM |
| Doxorubicin | yes | yes | yes | 0.2 uM |
| Camptothecin | yes | yes | yes | 0.08 uM |
| Vincrisitin | yes | yes | yes | 0.7 nM |
| Gemcitabine | yes | yes | yes | 4 nM |
| Estramustine | no | no | no | 182 uM |
| Temozolmide | no | no | no | inactive |
| 121974 | | | | 296 nM |
| Mab 17E6 | | | | 5 ng/ml |
| DI-17E6 | | | | 4 ng/ml |

The results show that in HUVEC DI-17E6 causes a distinct additive effect when combined with a second therapeutic agent like Paclitaxel, whereas other chemotherapeutics show, when combined with an engineered antibody according to the invention, no effect or only a slight additive effect.

Example 9

In Vitro Testing of DI17E6 in Combination with Chemotherapeutic Agents in Different Human Melanoma Cells In an in vitro proliferation assay the effect of a diversity of chemotherapeutics well known and applied in tumor therapy was investigated when combined with DI-17E6 in different human melanoma cell lines: m21, SKMEL-23, SKMEI; MeWo, WM-793.

The results show that there are only slight differences with respect to the chemotherapeutic agent used (in this case: cisplatin, paclitaxel, vinblastin, vincristin and temoyolomide.

Differences are recognizable with respect to the tumor cell line used. In all cases, DI-17E6 causes not more than additive affects of the chemotherapeutic agent.

In summary: no effect or only a slight additive effect was observed with the combination DI-17E6 plus chemotherapeutic agent for such tumor cell lines, which are insensitive to DI-17E6. A strong additive effect could be detected with the combination DI-17E6 plus chemotherapeutic agent for such tumor cell lines, which are sensitive to DI-17E6. In these case the proliferation profile corresponds to that as depicted for paclitaxel+DI-17E6 in HUVEC (see FIG. 6).

Example 10

Synergistic Combination of DI-17E6 and Cilengitide In Vitro

Unexpected findings have been achieved when combinations of DI-17E6 and cilengitide have been tested in vitro. NSCLC cell lines H322, A549, H1975 and H460, humans melanoma cell line M21, and renal carcinoma cell lines ACHN, A498, Caki 1 and Caki2 were treated with cilengitide in the presence of DI-17E6. The results showed considerable more cell death after 3 days grown in normal media, than in the presence of cilengitide or Di-17E6 alone.

A typical experimental set-up for testing the synergistic effect of DI-17E6 and cilengitide was performed as proliferation assay with M21, CAKI-2 and A498 cells:

96 well plates have been coated with vitronectin, and after being blocked, cells have been added (3000-5000 cells/well) and after 4 hours (enough time to allow cell attachment and spreading) drugs are added and allowed to grow in the presence of serially diluted Cilengitide alone or together with DI-17E6 at 1 μg/ml. Cells have further been incubated for 3 days, and cell viability was measured following the instructions of the Alamar Blue reagent provider.

FIG. 7 provides the cell death rate for said combination in M21 cells (upper curve: cilengitide alone, lower curve cilengitide+DI-17E6).

FIG. 8 provides the cell death rate for said combination in CAKI-2 cells (upper curve: cilengitide alone, lower curve cilengitide+DI-17E6).

FIG. 9 provides the cell death rate for said combination in A498 cells (upper curve: cilengitide alone, lower curve cilengitide+DI-17E6).

This is an unusual finding with both alphav integrins binders envisages pre-saturating the system with an allosteric inhibitor, before pulsed additions of the competitives inhibitor in the continued presence of the allosteric inhibitor. This gives a synergistic blockade of the integrin, greatly amplifying the effect of the competitive inhibitor alone, or steric/allosteric inhibitor alone. Importantly, the continuous presence of the competitive inhibitors is usually not necessary, its role is to release the primary interaction, allowing the allosteric inhibitor access.

Example 11

In Vivo Testing of DI-17E6 in Combination with Chemotherapeutic Agents

Gemcitabine Plus DI-17E6 in Human NP18-b3 Pancreatic Human Cells

The growth of an orthotopically xenografted pancreatic tumor in nude mice was investigated under systemic EMD 525797 plus gemcitabine co-treatment. Gemcitabine was selected for the combined treatment of an orthotopically xenografted human pancreatic tumor model because this is the best-approved chemotherapeutic agent for this indication.

NP18-b3 pancreatic human cell line, which expresses αvβ3-integrin, was implanted orthotopically into the pancreas of immunosuppressed mice. The animals were randomized to and one week later treatment with drugs and vehicle started.

Tumors were removed and cut into pieces of 10 mg each. These pieces were then sutured to the pancreas of healthy animals (one piece per animal). 4-6 weeks later, tumors were removed, cut into pieces again and stitched into new animals. Those new animals were then randomized and one week later treatment with drugs and vehicle was started. EMD 525797 was dosed i.p. at 500 μg per animal three times a week. Gemcitabine was administered as a suboptimal dose of 50 mg/Kg 3 times a week (suboptimal dose based on previous studies). In a fourth group, EMD 525797 was combined with suboptimal doses of gemcitabine based on previous experiments. Tumor growth measurement (weight of the removed tumors) was made 6 weeks after the tumor grafting.

Orthotopic tumors treated with EMD 525797 had similar size and weight than control vehicle treated animals. Similarly, gemcitabine, at the suboptimal dose was also not active.

However, at the same dosing as the monotherapeutic regimens, gemcitabine plus EMD 525797 had a synergistic activity with a tumor reduction of 52% (FIG. 10).

Cisplatin/Dacarbazine Plus DI-17E6 in Human M21 or MeWO Melanoma Xenograft Models M21 or MeWo human melanoma cells positive for expressing $\alpha v\beta 3$ integrin were subcutaneously inoculated into SCID or nude mice according to well known standard protocols.

DI-17E6 was administered systemically together with either cis-platinum (cPT) or Dacarbazine (DTIC), two chemotherapeutics used in clinical treatment of melanoma.

DI-17E6 was administered i.p. once per week from the same day of s.c. M21 or MeWo cell injection into the animals at a suboptimal weekly maintenance dose of 27.2 mg/Kg (corresponds ca. 500 ul/ml serum). DTIC was administered i.p. once per week at 50 mg/Kg, and cPT was administered i.p. once per week at 10 mg/Kg, each starting 11 days after tumor cell injection.

The results obtained with cisplatin in the M21 xenograft model is shown in FIG. 11. In contrast to in vitro data shown earlier the combination of cisplatin plus DI-17E6 in vivo clearly elicits a statistically significant synergistic increase in response compared to the administration of either drug treatment alone.

The results obtained with DTIC in the MeWo xenograft model is shown in FIG. 12. In contrast to in vitro data shown earlier the combination of cisplatin plus DI-17E6 in vivo clearly elicits a statistically significant synergistic increase in response compared to the administration of either drug treatment alone.

glutamine. 1 mM sodium pyruvate. 100 units/ml penicillin and 100 ug/ml streptomycin. Cells were passaged at confluence by washing once in cation-free PBS followed by a 3 minute incubation in trypsin (0.5 ug/ml)/EDTA (0.2 ug/ml) solution in PBS at 37° C. Cells were recovered in medium, centrifuged and taken up in medium and counted.

Animals used in this study were supplied by HARLAN INTERFAUNA IBERICA S.L. (Sant Feliu de Codines (Barcelona) Spain) and housed during the acclimatization period of a minimum of 5 days in the quarantine rooms on specific pathogen free facilities.

During the acclimatization period all observations were registered. All the animals were inspected by a veterinary to ensure the health of the animals.

The treatment started for all groups at day 0 of experiment (same day of cell injection).

Animals were treated intraperitoneally (i.p.) with product or vehicle at a volume of 10 mg/ml once weekly for EMD 525797 and twice weekly for Erbitux.

Treatment dosings for EMD 525797 were adjusted to the expected serum trough values of 100 µg/ml. To reach this serum trough values, animals were dosed following a single loading dose of 17.1 mg/kg plus multiple (weekly) maintenance dose of 5.1 mg/kg scheduling as described in the next table.

All animals were observed daily, controlling their physical conditions, behavior, presence of injuries, and any clinical sign.

Groups:

| Group | Substance administered | Serum through value (µg/ml) | Single loading dose DI17E6 (mg/kg) | Weekly maintenance doses (mg/kg) | Animal number |
|---|---|---|---|---|---|
| A | Vehicle (PBS) | 0 | 0 | 0 | 10 |
| B | DI17E6 | 100 | 17.1 | 5.1 (weekly) | 10 |
| C | Erbitux | — | 12 | 12 (bi-weekly) | 10 |
| D | Erbitux | — | 4 | 4 (bi-weekly) | 10 |
| E | DI17E6 + Erbitux | 100 | 17.1/12 | 5.1 (weekly)/12 (bi-weekly) | 10 |
| F | DI17E6 + Erbitux | 100 | 17.1/4 | 5.1 (weekly)/4 (bi-weekly) | 10 |

Example 12

In vivo testing of DI-17E6 in human CAKI-1 renal carcinoma xenograft mouse model CAKI-1 were subcutaneously inoculated into SCID or nude mice according to well known standard protocols.

DI-17E6 was administered systemically i.p. once per week from the same day of s.c. M21 or MeWo cell injection into the animals at different doses.

FIG. 13 shows that, surprisingly, DI-17E6 can reduce tumor volume/size from low (1 ug/mil) to medium (100 ug/ml serum) doses to approximately the same degree (no real dose effect), whereas administration of a high dose (500 ug/ml) leads to a complete reduction of tumor volume.

Example 13

Combinatorial Effect of DI-17E6 with Cetuximab (Erbitux®) in a CAKI-1 Human Renal Cell Carcinoma Xenograft Model The renal cell carcinoma cell line CAKI-1 was grown in RPMI containing 10% FCS (heat-inactivated) plus 2 mM Animals bearing human renal CAKI-1 xenograft tumors were treated with DI17E6, Erbitux or the combination of both starting at day 0, when the tumor cells were inoculated. The treatment duration for DI17E6 was 40 days and for Erbitux and the combination groups 29 days. The tumor growth was followed up to 111 days after tumor cell inoculation. Treatment with an initial dose of 17.1 mg/kg followed by a weekly treatment with 5.1 mg/kg DI17E6 resulted in trough values of 100 µg/ml causing a significant tumor growth inhibition at day 40, the end of treatment (T/C: 25%).

After day 40 a growth delay was still observable till the end of the observation period. Treatment twice weekly with either 4 mg/kg or 12 mg/kg Erbitux caused a strong and significant anti-tumor effect. T/Cs at day 29, the end of treatment were 9%. A similar strong anti-tumor effect was observed for both combinations DI17E6 plus 4 mg/kg Erbitux 2/w and DI17E6 plus 12 mg/kg 2/w. T/Cs at day 29, the end of treatment, were 10% and 9% (see table 1) respectively.

It should be noted, that 10 µg/ml serum/plasma corresponds to 0.55 mg/Kg body weight.

Figure 14:
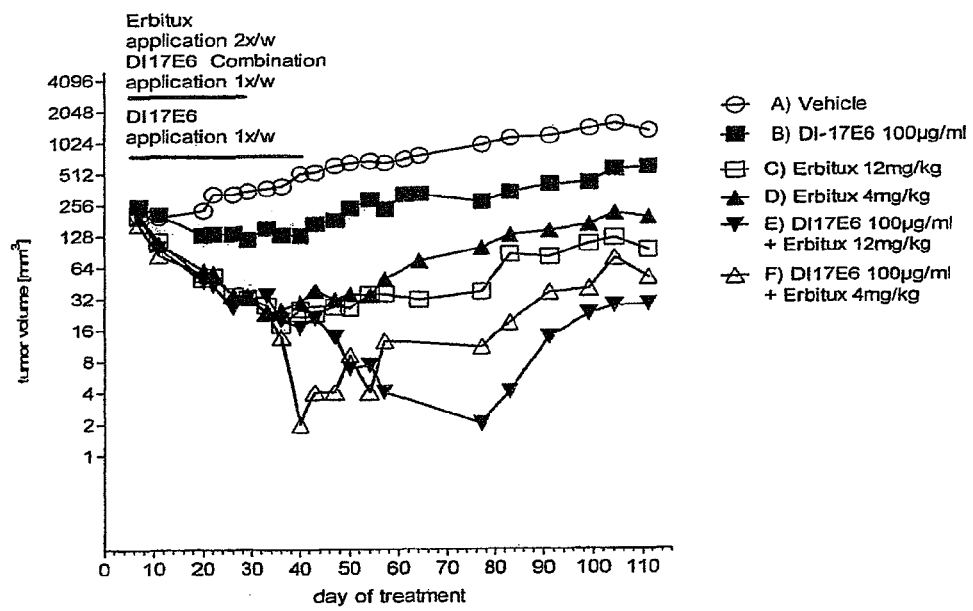

However, tumors in the treatment groups with Erbitux alone started to regrow after treatment stop. In contrast, in both combination groups the inhibition of the tumor growth continued apparent from the decreasing mean and median tumor sizes (FIG. 14).

At the end of the observation period in both combination groups only one of the tumors had reached the volume of day 7, which represents the day of the first tumor size measurement.

In the Erbitux monotherapy groups 3 tumors grew to considerable sizes (>1000 mm$^3$) and most of them grew to sizes above the tumor size at day 7.

In general all treatments were well tolerated as indicated by the weight gain during the experiment. The weight reduction in the vehicle group and in the DI17E6 treated group at one single measurement day was most likely caused by a lack of water supply. In both relevant groups the weight reduction was reversible followed by an ongoing weight gain.

Treatment with an initial dose of 17.1 mg/kg followed by a weekly dose of 5.1 mg/kg DI17E6 which lead to trough values of 100 µg/ml during the treatment period caused a significant growth inhibition of human renal CAKI-1 tumors. Also single treatment with two different doses of Erbitux using a biweekly schedule caused significant tumor growth inhibition. Both doses of Erbitux were approximately equally potent in their anti-tumor activity. The combination of DI17E6 with either 4 mg/kg Erbitux or 12 mg/kg Erbitux caused also a potent anti-tumor effect, which is comparable to the single Erbitux treatments during the treatment period.

However, the striking difference between the Erbitux monotherapies and the combination treatments is the growth behavior after treatment stop at day 29. As long as 82 days after treatment stop only one of the tumors in the combination group grew to the size of day 7, the first day of the tumor size measurements, which means that the tumors treated with DI17E6 and Erbitux either regressed or showed stable disease.

In contrast, in the two groups treated only with Erbitux some tumors grew after treatment stop to considerable sizes (varying from 429 to 3581 mm$^3$) indicating that the combination of DI17E6 and Erbitux could prevent relapse of tumor growth after Erbitux treatment.

The strong synergistic effect of DI-17E6 on the treatment with tyrosine kinase inhibitors, such as cetuximab (Erbitux®) can be regarded as extraordinaire and opens the field for a promising tumor combination therapy.

The invention claimed is:

1. An engineered recombinant anti-αv integrin antibody comprising:
   (i) the light chain CDR regions:
   CDR1: RASQDISNYLA (SEQ ID No. 7),
   CDR2: YTSKIHS (SEQ ID No. 8), and
   CDR3: QQGNTFPYT (SEQ ID No. 9);
   (ii) the heavy chain CDR regions:
   CDR1: SFWMH (SEQ ID No. 10),
   CDR2: YINPRSGYTEYNEIFRD (SEQ ID No. 11), and
   CDR3: FLGRGAMDY (SEQ ID No. 12);
   (iii) the light chain framework regions:
   FR-1: DIQMTQSPSSLSASVGDRVTITC (SEQ ID No. 14),
   FR-2: WYQQKPGKAPKLLIY (SEQ ID No. 15),
   FR-3: GVPSRFSGSGSGTDYTFTISSLQPEDIATYYC (SEQ ID No. 16), and
   FR-4: FGQGTKVEIK (SEQ ID No. 17)
   (iv) the heavy chain framework regions:
   FR1: QVQLQQSGGELAKPGASVKVSCKASGYTFS (SEQ ID No. 22),
   FR2: WVRQAPGQGLEWIG (SEQ ID No. 23),
   FR3: KATMTTDTSTSTAYMELSSLRSEDTAVYYCAS (SEQ ID No. 24), and
   FR4: WGQGTTVTVSS (SEQ ID No. 25); and
   (v) a heavy chain constant region derived from human IgG and a human constant light chain region.

2. The engineered antibody of claim 1, wherein the heavy chain constant region is derived from IgG2.

3. The engineered antibody of claim 2, wherein said IgG2 constant region comprises a modified IgG1 hinge region.

4. The engineered antibody of claim 3, wherein said modified IgG1 hinge region comprises the sequence EPKSSDKTHTCPPCP (SEQ ID No. 26).

5. The engineered antibody of claim 2, wherein said IgG2 constant region is modified by replacing amino acid N with Q at position 297 (N297Q).

6. The engineered antibody of claim 5, wherein amino acid residue F at position 296 is replaced by A (F296A) in order to eliminate a T-cell epitope generated by the modification at position 297.

7. The engineered antibody of claim 1, wherein the light chain constant region is human kappa.

8. The recombinant anti-αv-integrin hybrid antibody of claim 1 comprising:
   (i) variable and constant light chain sequences:
   DIQMTQSPSSLSASVGDRVTITCRASQDISNYLAWYQQKPGKAPKLLIYYTSKIHSGVPS RFSGSGSGTDYTFTISSLQPEDIATYYCQQGNTFPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNR GEC (SEQ ID No. 5) and
   (ii) variable and constant heavy chain sequences:
   QVQLQQSGGELAKPGASVKVSCKASGYTFSSFWMHWVRQAPGQGLEWIGYINPRSGYTEYNEIFRDKATMTTDTSTSTAYMELSSLRSEDTAVYYCASFLGRGAMDYWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVEPKSSDKTHTCPPCPAPPVAGPSVFLFPPKPKDTLMISRTPEVTCVVVDVSHEDPEVQFNWYVDGVEVHNAKTKPREEQAQSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTV DKSRWQQGNVFSCSVMHEALHNHYTQKSLSLSPGK (SEQ ID No. 6).

9. A pharmaceutical composition comprising a pharmaceutically effective amount of the antibody of claim 1 and a pharmaceutically acceptable carrier.

10. A pharmaceutical composition comprising a first and second pharmaceutically effective therapeutic agent, wherein the first agent is the antibody of claim 1, and the second agent is selected from the group consisting of: a chemotherapeutic agent, an angiogenesis inhibitor and an anti-tumor agent.

11. The pharmaceutical composition of claim 10, wherein the anti-tumor agent is an anti-tumor antibody.

12. The antibody of claim 1, wherein the antibody elicits a direct effect on tumor growth, which is independent of the indirect anti-tumor effect of the antibody caused by blocking angiogenesis.

13. The pharmaceutical composition of claim 11, wherein the anti-tumor antibody is an anti-EGFR antibody or an anti-Her2 antibody.

14. The pharmaceutical composition of claim 13, wherein the anti-EGFR antibody is cetuximab or matuzumab.

15. The pharmaceutical composition of claim 10, wherein the anti-angiogenesis inhibitor is the integrin inhibitor cilengitide.

16. The pharmaceutical composition of claim 10, wherein the chemotherapeutic agent is cisplatin or DTIC.

17. An engineered recombinant anti-αv integrin antibody comprising:
(i) the light chain CDR regions:
CDR1: RASQDISNYLA (SEQ ID No. 7),
CDR2: YTSKIHS (SEQ ID No. 8), and
CDR3: QQGNTFPYT (SEQ ID No. 9) and
(ii) the heavy chain CDR regions:
CDR1: SFWMH (SEQ ID No. 10),
CDR2: YINPRSGYTEYNEIFRD (SEQ ID No. 11), and
CDR3: FLGRGAMDY (SEQ ID No. 12).

18. The engineered antibody of claim 17, further comprising:
(iii) the light chain framework regions:
FR-1: DIQMTQSPSSLSASVGDRVTITC (SEQ ID No. 14),
FR-2: WYQQKPGKAPKLLIY (SEQ ID No. 15),
FR-3: GVPSRFSGSGSGTDYTFTISSLQPEDIATYYC (SEQ ID No. 16), and
FR-4: FGQGTKVEIK (SEQ ID No. 17).

19. The engineered antibody of claim 17, further comprising the heavy chain framework regions
FR1: QVQLQQSGAELAEPGASVKMSCKASGYTFS (SEQ ID No. 18)
FR2: WVKQRPGQGLEWIG (SEQ ID No. 19)
FR3: KATMTADTSSSTAYMQLSGLTSEDSAVYYCAS (SEQ ID No. 20)
FR4: WGQGTSVTVSS (SEQ ID No. 21),
wherein one, more or all of the bold and underlined positions are mutated in order to reduce or eliminate T-cell epitopes and thus immunogenicity in a human.

20. The engineered antibody of claim 19, wherein the heavy chain framework regions are:
FR1: QVQLQQSGGELAKPGASVKVSCKASGYTFS (SEQ ID No. 22),
FR2: WVRQAPGQGLEWIG (SEQ ID No. 23),
FR3: KATMTTDTSTSTAYMELSSLRSEDTAVYYCAS (SEQ ID No. 24), and
FR4: WGQGTTVTVSS (SEQ ID No. 25).

21. The engineered antibody of claim 17, further comprising a heavy chain constant region deriving from human IgG and a human constant light chain region.

22. The engineered antibody of claim 21, wherein the heavy chain constant region is derived from IgG2.

23. The engineered antibody of claim 22, wherein said IgG2 constant region comprises a modified IgG1 hinge region.

24. The engineered antibody of claim 23, wherein said modified IgG1 hinge region comprises the sequence EPKSSDKTHTCPPCP (SEQ ID No. 26).

25. The engineered antibody of claim 22, wherein said IgG2 constant region is modified by replacing amino acid N with Q at position 297 (N297Q).

26. The engineered antibody of claim 25, wherein amino acid residue F at position 296 is replaced by A (F296A) in order to eliminate a T-cell epitope generated by the modification at position 297.

27. The engineered antibody of claim 17, wherein the light chain constant region is human kappa.

28. The recombinant anti-αv-integrin hybrid antibody of claim 17 comprising:
(i) variable and constant light chain sequences:
DIQMTQSPSSLSASVGDRVTITCRASQDISNYLAWYQQKPGKAPKLLIYYTSKIHSGVPSRFSGSGSGTDYTFTISSLQPEDIATYYCQQGNTFPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID No. 5) and
(ii) variable and constant heavy chain sequences:
QVQLQQSGGELAKPGASVKVSCKASGYTFSSFWMHWVRQAPGQGLEWIGYINPRSGYTEYNEIFRDKATMTTDTSTSTAYMELSSLRSEDTAVYYCASFLGRGAMDYWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVEPKSSDKTHTCPPCPAPPVAGPSVFLFPPKPKDTLMISRTPEVTCVVVDVSHEDPEVQFNWYVDGVEVHNAKTKPREEQAQSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTV DKSRWQQGNVFSCSVMHEALHNHYTQKSLSLSPGK (SEQ ID No. 6).

29. A pharmaceutical composition comprising a pharmaceutically effective amount of the antibody of claim 17 and a pharmaceutically acceptable carrier.

30. A pharmaceutical composition comprising a first and second pharmaceutically effective therapeutic agent, wherein the first agent is the antibody of claim 17, and the second agent is selected from the group consisting of: a chemotherapeutic agent, an angiogenesis inhibitor and an anti-tumor agent.

31. The pharmaceutical composition of claim 30, wherein the anti-tumor agent is an anti-tumor antibody.

32. The pharmaceutical composition of claim 31, wherein the anti-tumor antibody is an anti-EGFR antibody or an anti-Her2 antibody.

33. The pharmaceutical composition of claim 32, wherein the anti-EGFR antibody is cetuximab or matuzumab.

34. The pharmaceutical composition of claim 30, wherein the anti-angiogenesis inhibitor is the integrin inhibitor cilengitide.

35. The pharmaceutical composition of claim 30, wherein the chemotherapeutic agent is cisplatin or DTIC.

36. The antibody of claim 17, wherein the antibody elicits a direct effect on tumor growth, which is independent of the indirect anti-tumor effect of the antibody caused by blocking angiogenesis.

\* \* \* \* \*

UNITED STATES PATENT AND TRADEMARK OFFICE
CERTIFICATE OF CORRECTION

PATENT NO. : 8,562,986 B2  Page 1 of 1
APPLICATION NO. : 12/669408
DATED : October 22, 2013
INVENTOR(S) : Simon Goodman et al.

It is certified that error appears in the above-identified patent and that said Letters Patent is hereby corrected as shown below:

In the Specification

At column 5, line 55, replace "SEQ ID No. 8" with --SEQ ID No. 10--.

At column 5, line 57, replace "SEQ ID No. 11" with --SEQ ID No. 13--.

At column 5, line 60, replace "SEQ ID No. 10" with --SEQ ID No. 12--.

At column 5, line 66, replace "SEQ ID No. 9" with --SEQ ID No. 11--.

At column 6, line 7, replace "SEQ ID No. 12" with --SEQ ID No. 14--.

At column 6, line 10, replace "SEQ ID No. 13" with --SEQ ID No. 15--.

At column 6, line 13, replace "SEQ ID No. 14" with --SEQ ID No. 16--.

At column 6, line 15, replace "SEQ ID No. 15" with --SEQ ID No. 17--.

At column 7, line 41, replace "SEQ ID No. 24" with --SEQ ID No. 26--.

At column 7, line 55, replace "SEQ ID No. 3" with --SEQ ID No. 5--.

At column 8, line 2, replace "SEQ ID No. 4" with --SEQ ID No. 6--.

Signed and Sealed this
Thirty-first Day of December, 2013

Margaret A. Focarino
*Commissioner for Patents of the United States Patent and Trademark Office*